United States Patent [19]

Levitt

[11] Patent Number: 4,861,366

[45] Date of Patent: Aug. 29, 1989

[54] HERBICIDAL ACETALS AND KETALS

[75] Inventor: George Levitt, Wilmington, Del.

[73] Assignee: E. I. Du Pont de Nemours and Company, Wilmington, Del.

[21] Appl. No.: 176,254

[22] Filed: Mar. 31, 1988

Related U.S. Application Data

[60] Division of Ser. No. 6,434, Jan. 23, 1987, Pat. No. 4,753,672, which is a division of Ser. No. 754,709, Jul. 16, 1985, Pat. No. 4,659,369, which is a continuation-in-part of Ser. No. 644,259, Aug. 27, 1984, abandoned.

[51] Int. Cl.$^4$ .................. C07D 401/12; C07D 405/12; A01N 43/66; A01N 43/68

[52] U.S. Cl. .......................................... 71/90; 71/93; 544/211; 544/212; 544/197; 544/198; 544/206; 544/207; 544/208; 544/209

[58] Field of Search ............. 71/93, 90; 544/219, 544/211, 212, 197, 198, 206, 207, 208, 209

[56] References Cited

U.S. PATENT DOCUMENTS 4,764,203  8/1988  Topfl et al. ........................ 71/93

Primary Examiner—John M. Ford

[57] ABSTRACT

Novel furan- and thiophenesulfonamides such as 3-(1,3-dioxolan-2-yl)-N-[(4-methoxy-6-methyl-1,3-5-triazin-2-yl)aminocarbonyl]-2-thiophenesulfonamide and N-[(4,6-dimethoxypyrimidin-2-yl)aminocarbonyl]-3-(1,3-dioxolan-2-yl)-2-thiophenesulfonamide are highly active pre-emergent and/or post-emergent herbicides.

49 Claims, No Drawings

HERBICIDAL ACETALS AND KETALS

This is a division of application U.S. Ser. No. 006,434 filed Jan. 23, 1987, now U.S. Pat. No. 4,753,672 which in turn is a division of application U.S. Ser. No. 754,709 filed July 16, 1985, now U.S. Pat. No. 4,659,369, which in turn is a continuation-in-part of application U.S. Ser. No. 644,259 filed Aug. 27, 1984, now abandoned.

BACKGROUND OF THE INVENTION

The present invention relates to a novel class of furan- and thiophenesulfonamide compounds and their use as pre-emergent and post-emergent herbicides and as plant growth regulators.

U.S. Pat. Nos. 4,169,719 and 4,127,405 disclose herbicidal benzene-, furan- and thiophenesulfonamides of general formula

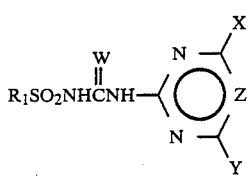

where $R_1$ may be an optionally substituted benzene or a furan or thiophene substituted with H, Cl, Br or $CH_3$.

U.S. Pat. No. 4,398,939 discloses herbicidal thiophenesulfonamides of formula

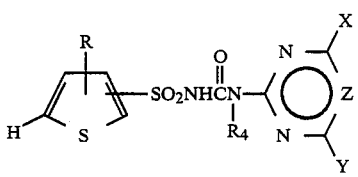

where R is $C_1$–$C_4$ alkyl, $C_3$ alkenyl, $OCH_3$, $NO_2$, Cl, Br, $SO_2NR_1R_2$ or $SO_2N(OCH_3)CH_3$.

European patent application (EP-A) No. 30,142, published 6/10/81 discloses herbicidal furan- and thiophenesulfonamides of formula

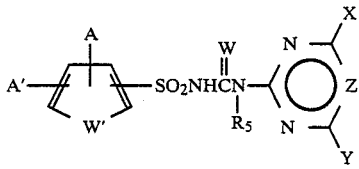

where
W' is O or S;
A is $C(O)QR^I$ or $C(=T)R^{II}$; and
A' is H, Cl, Br, $C_1$–$C_4$ alkyl, $OCH_3$, $NO_2$ or $CF_3$.

U.S. Pat. No. 4,370,480 teaches herbicidal benzenesulfonamides of general formula

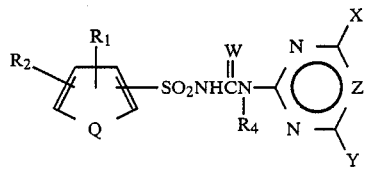

where $R_1$ is

EP-A-64,804, published 11/17/82, teaches herbicidal furan- and thiophenesulfonamides of general formula

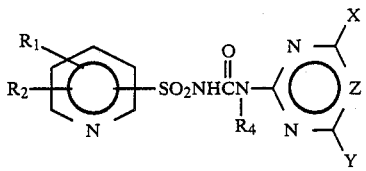

where
$R_1$ is $S(O)_nR_6$; and
$R_2$ is H, Cl, Br or $CH_3$;

EP-A-13,480 discloses herbicidal pyridine-sulfonamides of formula

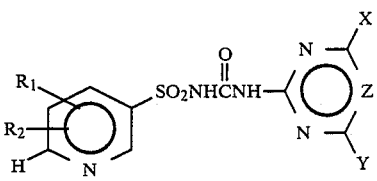

where
$R_1$ is H, Cl, Br, F, $C_1$–$C_4$ alkyl, $C_1$–$C_4$ alkoxy, $C_1$–$C_4$ alkylthio, $NO_2$ or $CO_2R_5$; and
$R_2$ is H, Cl, Br or $CH_3$.

EP-A-35,893 discloses herbicidal pyridine-sulfonamides of formula where
$R_1$ is $S(O)_nR_3$; and
$R_2$ is H, Cl, F, Br, $CH_3$, $OCH_3$, $CF_3$, $NO_2$, CN or $NH_2$.

EP-A-97,122, published Dec. 28, 1983, discloses herbicidal sulfonamides of formula

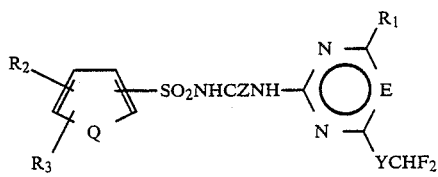

where
X is O, S, NR$_4$ or CR$_5$=N; and
R$_2$ is H, C$_1$-C$_3$ alkyl, haloalkyl, alkoxy, alkylthio, alkylsulfonyl, halogen, NO$_2$, CWR$_8$, SO$_2$NR$_6$R$_7$ or COR$_9$.

EP-A-95,925, published Dec. 7, 1983, and EP-A-87,780, published Sept. 7, 1983, teach herbicidal pyrazole sulfonylureas.

EP-A-95,925 (published Dec. 7, 1983) and EP-A-87,780 (published Sept. 7, 1983) teach herbicidal pyrazole sulfonylureas.

EP-A-126,711 (published 11/28/84; Swiss priority 5/16/83) discloses herbicidal sulfonylureas of the formula

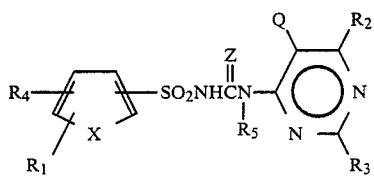

wherein
X is O, S, —NR$_5$,

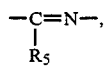

—CH=CH— or an annelated phenyl ring;
Z is O or S;
Q is halogen, C$_1$-C$_4$ alkyl, cyano, etc.;
R$_1$ is H, halogen, NO$_2$ or a group

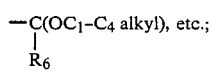

R$_6$ is, inter alia, H or C$_1$-C$_4$ alkyl; and
R$_2$ and R$_3$ can be, among other things, C$_1$-C$_4$ alkyl or C$_1$-C$_4$ alkoxy.

SUMMARY OF THE INVENTION

This invention relates to novel compounds of Formula I, agriculturally suitable compositions containing them and their method-of-use as preemergent and/or postemergent herbicides or plant growth regulators.

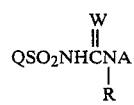

wherein Q is

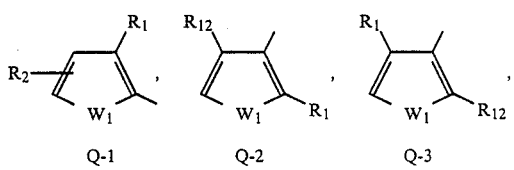

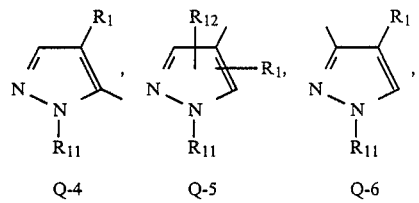

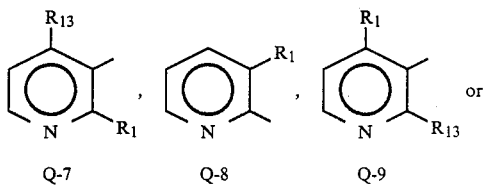

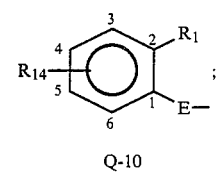

R is H or CH$_3$;
R$_1$ is

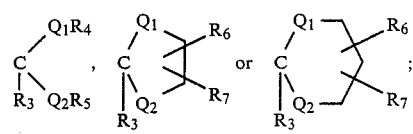

E is CH$_2$ or a single bond;
R$_2$ is H, C$_1$-C$_2$ alkyl or Cl;
R$_3$ is H, C$_1$-C$_3$ alkyl or C$_1$-C$_3$ alkoxy;
R$_4$ and R$_5$ are independently C$_1$-C$_2$ alkyl;
R$_6$ and R$_7$ are independently H or C$_1$-C$_2$ alkyl;
W is O or S;
W$_1$ is O or S;
Q$_1$ and Q$_2$ are independently O, S or NCH$_3$; A is

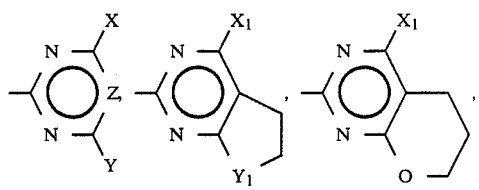

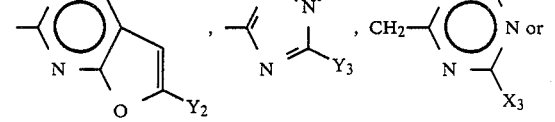

-continued

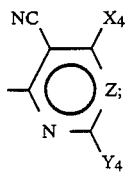

A-7

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkoxy, amino, $C_1$-$C_3$ alkylamino or di($C_1$-$C_3$)alkylamino;

Y is H, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino, di($C_1$-$C_3$)alkylamino, $C_3$-$C_4$ alkenyloxy, $C_3$-$C_4$ alkynyloxy, $C_2$-$C_5$ alkylsulfinylalkyl, $C_1$-$C_4$ haloalkyl, $C_2$-$C_5$ alkylsulfonylalkyl, $C_3$-$C_5$ cycloalkyl, $C_2$-$C_4$ alkynyl, $C_2$-$C_5$ alkylthioalkyl, C(O)$R_8$,

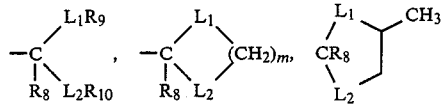

or N(OCH$_3$)CH$_3$;
m is 2 or 3;
$L_1$ and $L_2$ are independently O or S;
$R_8$ is H or CH$_3$;
$R_9$ and $R_{10}$ are independently $C_1$-$C_2$ alkyl;
$R_{11}$ is $C_1$-$C_3$ alkyl;
$R_{12}$ is H, F, Cl, NO$_2$, $C_1$-$C_2$ alkyl, $C_1$-$C_2$ alkoxy, $C_1$-$C_2$ alkylthio, $C_1$-$C_2$ alkylsulfinyl, $C_1$-$C_2$ alkylsulfonyl, di($C_1$-$C_2$)alkylsulfamoyl or CO$_2$($C_1$-$C_2$ alkyl);
$R_{13}$ is H, $C_1$-$C_2$ alkyl, $C_1$-$C_2$ alkoxy, Cl, F or NO$_2$;
$R_{14}$ is H, $C_1$-$C_3$ alkyl, $C_1$-$C_3$ alkoxy, $C_1$-$C_3$ haloalkyl, $C_1$-$C_3$ haloalkoxy, Cl, Br, F, NO$_2$, di($C_1$-$C_3$)alkylsulfamoyl, $C_1$-$C_3$ alkylthio, $C_1$-$C_3$ alkylsulfinyl, $C_1$-$C_3$ alkylsulfonyl, amino, $C_1$-$C_3$ alkylamino, di($C_1$-$C_3$)alkylamino, CH$_2$OCH$_3$, CH$_2$SCH$_3$ or CH$_2$CN.
Z is CH or N;
$Y_1$ is O or CH$_2$;
$X_1$ is CH$_3$, OCH$_3$, OC$_2$H$_5$ or OCF$_2$H; and
$Y_2$ is H or CH$_3$;
$X_2$ is CH$_3$, C$_2$H$_5$ or CH$_2$CF$_3$;
$Y_3$ is OCH$_3$, OC$_2$H$_5$, SCH$_3$, SC$_2$H$_5$, OCF$_2$H, SCF$_2$H, CH$_3$ or C$_2$H$_5$;
$X_3$ is CH$_3$ or OCH$_3$;
$Y_4$ is CH$_3$, OCH$_3$, OC$_2$H$_5$ or Cl; and
$X_4$ is CH$_3$, OCH$_3$, OC$_2$H$_5$, CH$_2$OCH$_3$ or Cl;
and their agriculturally suitable salts; provided that
(a) when X is Cl, F, Br or I, then Z is CH and Y is OCH$_3$, OC$_2$H$_5$, N(OCH$_3$)CH$_3$, NHCH$_3$, N(CH$_3$)$_2$ or OCF$_2$H;
(b) when Y is cyclopropyl, X is other than Cl, F, Br or I;
(c) when $R_3$ is $C_1$-$C_3$ alkoxy, then $Q_1$ and $Q_2$ are oxygen;
(d) when $R_3$ is H or $C_1$-$C_3$ alkyl, then Q is Q-1 through Q-9;
(e) when X or Y is OCF$_2$H, then Z is CH;

(f) when the total number of carbon atoms of X and Y is greater than four, then the combined number of carbons of the substituents on Q is less than or equal to ten;
(g) when W is S, then A is A-1, R is H, and Y is CH$_3$, OCH$_3$, OC$_2$H$_5$, CH$_2$OCH$_3$, C$_2$H$_5$, CF$_3$, SCH$_3$, OCH$_2$CH=CH$_2$, OCH$_2$C≡CH, OCH$_2$CH$_2$OCH$_3$, CH(OCH$_3$)$_2$ or

(h) when A is A-7 and Z is N, then $R_3$ is $C_1$-$C_3$ alkoxy;
(i) when E is CH$_2$, then $R_{14}$ is H, CH$_3$, OCH$_3$, Cl or NO$_2$ and is not in the 4-position.

In the above definitions, the term "alkyl" used either alone or in compound words such as "alkylthio" or "haloalkyl", denotes straight chain or branched alkyl, e.g., methyl, ethyl, n-propyl, isopropyl or the different butyl isomers.

Alkoxy denotes methoxy, ethoxy, n-propoxy, isopropoxy and the different butoxy isomers.

Alkenyl denotes straight chain or branched alkenes, e.g., 1-propenyl, 2-propenyl, 3-propenyl and the different butenyl isomers.

Alkynyl denotes straight chain or branched alkynes, e.g., ethynyl, 1-propynyl, 2-propynyl and the different butynyl isomers.

Cycloalkyl denotes cyclopropyl, cyclobutyl and cyclopentyl.

The term "halogen", either alone or in compound words such as "haloalkyl", denotes fluorine, chlorine, bromine or iodine.

In terms such as $C_2$-$C_5$ alkoxyalkoxy, the specified number of carbon atoms is meant to define the total number of carbon atoms in that substituent group. For example, $C_2$-$C_5$ alkoxyalkoxy would represent OCH$_2$OCH$_3$ through O(CH$_2$)$_4$OCH$_3$ or OCH$_2$O(CH$_2$)$_3$CH$_3$ and the various structural isomers embraced therein.

Alkylsulfonyl denotes methylsulfonyl, ethylsulfonyl and the different propylsulfonyl isomers.

Alkylthio, alkylsulfinyl, alkylamino, alkylsulfamoyl, etc., are defined in an analogous manner.

PREFERRED COMPOUNDS

Preferred for reasons of their higher herbicidal efficacy, greater plant growth regulant activity and/or more favorable ease of synthesis are:
(1) Compounds of Formula I where
  $R_3$ is H or $C_1$-$C_3$ alkyl;
(2) Compounds of Formula I where
  $R_3$ is $C_1$-$C_3$ alkoxy;
(3) Compounds of Preferred 1 where
  W is O;
  R is H;
  X is CH$_3$, OCH$_3$, OC$_2$H$_5$, Cl, F, Br, I, OCF$_2$H, CH$_2$F, OCH$_2$CH$_2$F, OCH$_2$CHF$_2$, OCH$_2$CF$_3$ or CF$_3$; and
  Y is H, $C_1$-$C_3$ alkyl, OCH$_3$, OC$_2$H$_5$, CH$_2$OCH$_3$, NHCH$_3$, N(OCH$_3$)CH$_3$, N(CH$_3$)$_2$, CF$_3$, SCH$_3$, OCH$_2$CH=CH$_2$, OCH$_2$C≡CH, OCH$_2$CH$_2$OCH$_3$, CH$_2$SCH$_3$, CH$_2$OC$_2$H$_5$,

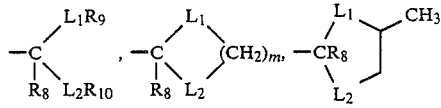

OCF$_2$H, C≡CH, C≡CCH$_3$, SCF$_2$H or cyclopropyl;

(4) Compounds of Preferred 3 where
Q$_1$ and Q$_2$ are identical and are O or S;
R$_{12}$ is H, C$_1$–C$_2$ alkyl or Cl;
R$_{13}$ is H; and (5) Compounds of Preferred 4 where
A is A-1;
Y is CH$_3$, OCH$_3$, OC$_2$H$_5$, CH$_2$OCH$_3$, C$_2$H$_5$, NHCH$_3$, CH$_2$OC$_2$H$_5$, OCF$_2$H, OCH$_2$CH$_2$OCH$_3$, cyclopropyl, C≡CH or CH(OCH$_3$)$_2$; and
X is CH$_3$, OCH$_3$, Cl, OC$_2$H$_5$, OCF$_2$H or OCH$_2$CF$_3$;

(6) Compounds of Preferred 5 where Q$_1$ and Q$_2$ are O;
(7) Compounds of Preferred 5 where Q$_1$ and Q$_2$ are S;
(8) Compounds of Preferred 5 where Q is Q-1;
(9) Compounds of Preferred 5 where Q is Q-2;
(10) Compounds of Preferred 5 where Q is Q-3;
(11) Compounds of Preferred 5 where Q is Q-4;
(12) Compounds of Preferred 5 where Q is Q-5;
(13) Compounds of Preferred 5 where Q is Q-6;
(14) Compounds of Preferred 5 where Q is Q-7;
(15) Compounds of Preferred 5 where Q is Q-8;
(16) Compounds of Preferred 5 where Q is Q-9;
(17) Compounds of Preferred 2 where
W is O;
R is H;
X is CH$_3$, OCH$_3$, OC$_2$H$_5$, Cl, F, Br, I, OCF$_2$H, CH$_2$F, OCH$_2$CH$_2$F, OCH$_2$CHF$_2$, OCH$_2$CF$_3$ or CF$_3$; and
Y is H, C$_1$–C$_3$ alkyl, OCH$_3$, OC$_2$H$_5$, CH$_2$OCH$_3$, NHCH$_3$, N(OCH$_3$)CH$_3$, N(CH$_3$)$_2$, CF$_3$, SCH$_3$, OCH$_2$CH=CH$_2$, OCH$_2$C≡CH, OCH$_2$CH$_2$OCH$_3$, CH$_2$SCH$_3$, CH$_2$OC$_2$H$_5$,

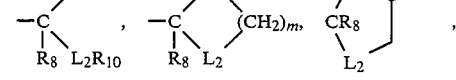

OCF$_2$H, SCF$_2$H, cyclopropyl, C≡CH or C≡CCH$_3$;

(18) Compounds of Preferred 17 where
E is a single bond;
R$_{12}$ is H, C$_1$–C$_2$ alkyl or Cl;
R$_{13}$ is H; and
R$_{14}$ is H, F, Cl, Br, C$_1$–C$_2$ alkyl, C$_1$–C$_2$ alkoxy or C$_1$–C$_2$ alkylthio and is not para to the sulfonylurea bridge;

(19) Compounds of Preferred 18 where
A is A-1;
Y is CH$_3$, OCH$_3$, OC$_2$H$_5$, CH$_2$OCH$_3$, C$_2$H$_5$, NHCH$_3$, CH$_2$OC$_2$H$_5$, OCF$_2$H, OCH$_2$CH$_2$OCH$_3$, cyclopropyl, C≡CH or CH(OCH$_3$)$_2$; and
X is CH$_3$, OCH$_3$, Cl, OC$_2$H$_5$, OCF$_2$H or OCH$_2$CF$_3$;

(20) Compounds of Preferred 19 where Q is Q-1;
(21) Compounds of Preferred 19 where Q is Q-2;
(22) Compounds of Preferred 19 where Q is Q-3;
(23) Compounds of Preferred 19 where Q is Q-4;
(24) Compounds of Preferred 19 where Q is Q-5;
(25) Compounds of Preferred 19 where Q is Q-6;
(26) Compounds of Preferred 19 where Q is Q-7;
(27) Compounds of Preferred 19 where Q is Q-8;
(28) Compounds of Preferred 19 where Q is Q-9;
(29) Compounds of Preferred 19 where Q is Q-10;

Specifically Preferred for reasons of highest herbicidal efficacy and/or most favorable ease of synthesis are:

3-(1,3-dioxolan-2-yl)-N-[(4-methoxy-6-methyl-1,3,5-triazin-2-yl)aminocarbonyl]-2-thiophenesulfonamide, m.p. 164°–166° C.; and N-[(4,6-dimethoxypyrimidin-2-yl)aminocarbonyl]-3-(1,3-dioxolan-2-yl)-2-thiophenesulfonamide, m.p. 137°–150° C.

DETAILED DESCRIPTION OF THE INVENTION

Synthesis

The compounds of Formula I can be prepared by one or more of the methods shown in Equations 1–7.

As shown in Equation 1, compounds of Formula I (where W is O) can be prepared by treating sulfonamides of Formula II with phenyl esters of N-heterocycliccarbamic acids of Formula III in the presence of a strong organic base such as 1,8-diazabicyclo[5.4.0]undec-7-ene (DBU).

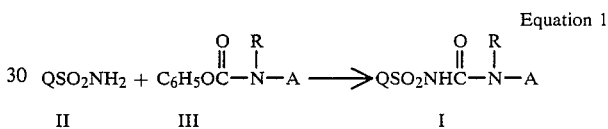

Equation 1 wherein Q, R and A are as previously defined. The reaction of Equation 1 is generally carried out in the range of 0° to 50° C. in an inert solvent such as dioxane or acetonitrile, analogous to methods taught in EP-A 44,807. The required carbamates can be prepared from the corresponding amines, IIIa, and diphenyl carbonate or phenylchloroformate and a base such as sodium hydride as shown in Equation 2.

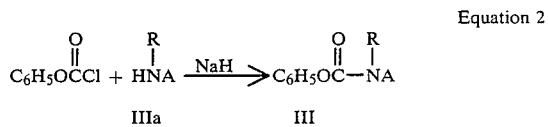

Equation 2

Compounds of Formula I may also be prepared as shown in Equation 3 by treating sulfonamides of Formula II with the methyl ester of an N-heterocycliccarbamic acid of Formula IIIb in the presence of an equimolar quantity of trimethylaluminum.

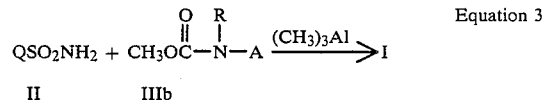

Equation 3

The reaction of Equation 3 is best carried out at temperatures between 25° and 83° C. in a solvent such as methylene chloride or 1,2-dichloroethane for 12 to 95 hours under an inert atmosphere, as taught in EP-A 84,244, published July 27, 1983. The methyl carbamates, IIIb, can be conveniently synthesized by treatment of the corresponding heterocyclic amines of Formula IIIa with dimethyl carbonate or methyl chloroformate in the presence of a base such as sodium hydride.

Alternatively, compounds of Formula I can be prepared by the reaction of a sulfonylcarbamate of Formula IV with an aminoheterocycle of Formula IIIa as shown in Equation 4.

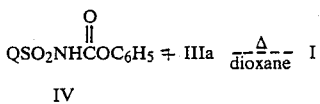

Equation 4

The reaction is carried out at 50° to 100° C. in a solvent such as dioxane for 0.5 to 24 hours as taught in EP-A-44,807. The required carbamates of Formula IV are prepared by the reaction of the corresponding sulfonamides of Formula II with diphenylcarbonate or phenylchloroformate in the presence of a base such as sodium hydride.

Compounds of Formula I, where W is S, can be prepared via addition of an appropriate heterocyclic amine, IIIa, to a sulfonyl isothiocyanate of the formula $QSO_2NCS$. This reaction is best carried out according to methods taught in U.S. Pat. No. 4,127,405.

Sulfonyl isothiocyanates of the formula $QSO_2NCS$ can be prepared according to the procedure of K. Hartke, *Arch. Pharm.*, 299, 174 (1966).

Sulfonamides of Formula II used in the preparation of compounds of Formula I are useful intermediates. They can be prepared by a variety of methods known in the art. For example, contacting an appropriately substituted sulfonyl chloride IIa with ammonium hydroxide or ammonia in an inert solvent such as ether or tetrahydrofuran affords sulfonamides II as shown by Equation 5a and 5b.

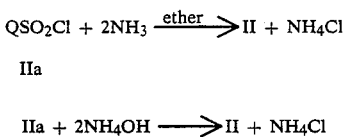

The reaction of sulfonyl chlorides, IIa, with ammonia is best carried out at −33° to 50° C. for 0.1 to 24 hours. After removal of the ammonium chloride by-product by filtration or extraction with water, the desired product can be isolated by the evaporation of the organic solvent.

Ammonium hydroxide can be used in place of ammonia as in Equation 5b. This reaction is widely reported in the literature, c.f., *Methoden Der Organischen Chemie* (Houben-Weyl), Vol. 9, Ch. 19, edited by F. Muth, Stuttgart, 1955.

Alternatively, sulfonamides of Formula II can be prepared by the reaction of a lithium salt of an appropriately substituted sulfinic acid, IIb, with chloramine as shown in Equation 6.

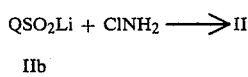

Equation 6

This reaction can be carried out using the conditions referred to in the preceding reference.

Lithium salts of Formula IIb can also be converted to the sulfonamides of Formula IIa by the procedures taught in U.S. Pat. No. 4,441,910.

Sulfonyl chlorides of Formula IIa can be prepared by the reaction of lithium salts of Formula IIc with sulfuryl chloride at −50° to −20° C. in an inert solvent such as tetrahydrofuran or ether as shown in Equation 7.

| Equation 7 | | |
|---|---|---|
| (a) QH + R'Li | → | QLi |
| | | IIc |
| (b) QBr + R'Li | → | IIc |
| (c) IIc + $SO_2Cl_2$ | → | IIa |

Where R' is a group such as butyl, phenyl, diisopropylamino or similar moiety commonly combined with lithium to form a lithiation agent. These agents and their method of use are described in N. S. Narasimhan and R. S. Mali, *Synthesis*, 957–86 (1983) or in *The Chemistry of Organolithium Compounds*, Wakefield, Pergamon Press, Oxford, 1974 or also H. W. Gschwend and H. R. Rodriguez, *Org. React.* 26, 1 (1978).

The sulfonyl chlorides, IIa, can be isolated by extracting the inorganic by-products with water followed by drying the organic layer over a drying agent such as magnesium sulfate, filtering the dried solution and evaporation of the solvent.

Lithium salts of Formula IIb can be prepared by contacting sulfur dioxide with the lithiated intermediate IIc using procedures described in the above references on the lithiated intermediates.

The formation of orthoesters, acetals, cyclic acetals, thioacetals and their amino analogs where $Q_1$ or $Q_2$ are N—$CH_3$ is widely reported in the literature, c.f.: *Synthetic Organic Chemistry*, R. B. Wagner and H. D. Zook, Ch. 8, John Wiley & Sons, New York, 1953; or *Organic Synthesis*, V. Migrdichian, Ch. 5, Reinhold, London, 1957.

The desired aldehyde and acetyl substituted thiophenes can be prepared by a variety of methods as described, for example, in "The Chemistry of Heterocyclic Compounds", vol. 3, edited by H. D. Hartough, F. P. Hochgesang and F. F. Blicke, Interscience, N.Y., 1952. Pyrazole aldehydes and acetylpyrazoles can be prepared according procedures described in "The Chemistry of Heterocyclic Compounds", Vol. 22, edited by R. H. Wiley, Interscience, N.Y., 1967. Aldehydes and acetyl derivatives of furan can be prepared according to methods cited in "Advances in Heterocyclic Chemistry", Vol. 7, edited by A. R. Katritzky and A. J. Boulton, and Vol. 30 edited by A. R. Katritzky, Academic Press, N.Y., 1962 and 1982. Further references to the literature of heterocyclic compounds can be found on pages 225–299 of Vol. 7 cited above.

The heterocyclic amines of Formula IIIa can be prepared by methods known in the literature, or simple modifications thereof, by those skilled in the art. For instance, EP-A No. 84,224 (published July 27, 1983) and W. Braker et al., *J. Am. Chem. Soc.*, 69, 3072 (1947) describes methods for preparing aminopyrimidines and triazines substituted by acetal groups such as dialkoxymethyl or 1,3-dioxolan-2-yl, among other groups. Also, for example, South African patent application Nos. 82/5045 and 82/5671 describe methods for preparing aminopyrimidines and triazines substituted by haloalkyl or haloalkylthio groups such as $OCH_2CH_2F$, $OCH_2CF_3$, $SCF_2H$, or $OCF_2H$, among other groups. South African patent application 83/7434 (published Oct. 5, 1983) describes methods for the synthesis of cyclopropylpyrimidines and triazines substituted by such groups as alkyl, haloalkyl, alkoxy, haloalkoxy, alkylamino, dialkylamino or alkoxyalkyl.

The 5,6-dihydrofuro[2.3-d]pyrimidin-2-amines, the cylcopenta[dπpyrimidin-2-amines (IIIa, A is A-2) and the 6,7-dihydro-5H-pyrano[2.3-d]pyrimidin-2-amines (IIIa, A is A-3) can be prepared as described in EP-A No. 15,683. The furo[2.3-d]pyrimidin-2-amines (III, A is A-4) are described in EP-A No. 46,677.

Compounds of Formula IIIa, where A is A-5, are described in EP-A-73,562. Compounds of Formula IIIa, where A is A-6, are described in EP-A-94,260. Compounds of Formula IIIa, where A is A-7, can be prepared by methods taught in EP-A-125,864.

In addition, general methods for preparing aminopyrimidines and triazines have been reviewed in the following publications:

"The Chemistry of Heterocyclic Compounds," a series published by Interscience Publ., New York and London;
"Pyrimidines", Vol. 16 of the same series by D. J. Brown;
"s-Triazines and Derivatives," Vol. 13 of the same series by E. M. Smolin and L. Rapaport;
F. C. Schaefer, U.S. Pat. No. 3,154,547 and K. R. Huffman and F. C. Schaefer, J. Org. Chem., 28, 1812 (1963), which describes the synthesis of triazines.

Agriculturally suitable salts of compounds of Formula I are also useful herbicides and can be prepared in a number of ways known in the art. For example, metal salts can be made by contacting compounds of Formula I with a solution of an alkali or alkaline earth metal salt having a sufficiently basic anion (e.g., hydroxide, alkoxide or carbonate). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble.

Acid addition salts, useful in this invention, can be obtained by reacting a compound for Formula I with a suitable acid, e.g., p-toluenesulfonic acid, trichloroacetic acid or the like.

The preparation of the compounds of this invention is further illustrated by the following specific examples. Unless otherwise indicated, temperatures are given in degrees centigrade.

EXAMPLE 1

3-(1,3-Dioxolan-2-yl)thiophene-2-sulfonyl chloride

To 23.4 g of 3-(1,3-dioxolan-2-yl)thiophene (S. Gronowitz, et al., Arkiv. Kemi., 20, 407 (1963)) in 100 ml of anhydrous tetrahydrofuran was added 100 ml of 1.6 molar n-butyllithium in hexane, with ice bath cooling. After stirring at room temperature for 20 minutes the mixture was cooled to −78° and sulfuryl chloride (16.2 g) was then added dropwise. This addition caused the suspended solids to form a tarry mass which broke up when the mixture was allowed to warm to room temperasture. After stirring one and one half hours at room temperature the mixture was cooled to −10° and 10 ml of ethyl acetate was added dropwise. The reaction mixture was then poured into ice water and extracted with ethyl ether. The ether portions were combined, dried over magnesium sulfate, filtered and the ether removed in vacuo-to yield 19.6 g of an oil. Infrared absorption spectra of this product showed peaks at 1330 and 1180 cm$^{-1}$, consistent for the desired sulfonyl chloride. Mass spectrum analysis: calc. 254, found 253 (Mass-1H) and the presence of a chlorine atom.

EXAMPLE 2

3-(1,3-Dioxolan-2-yl)thiophene-2-sulfonamide

To 5 ml of liquified ammonia gas dissolved in 50 ml of tetrahydrofuran was added dropwise with stirring and cooling 12.7 g of 3-(1,3-dioxolan-2-yl)thiophene-2-sulfonyl chloride. After stirring overnight at ambient temperature, the tetrahydrofuran was removed in vacuo, water was added to the residue and the mixture was extracted twice with 75 ml of methylene chloride. After washing the combined methylene chloride extracts with water, drying over magnesium sulfate, filtering off the drying agent and evaporation of the methylene chloride, an oily solid residue was obtained. This was chromatographed through silica gel using 1:1 ethyl acetate-hexanes as eluant (Rf 0.35). Evaporation of the solvent mixture yielded 2.2 g of the desired product, as a waxy solid. Infrared absorption spectra showed peaks at 3360, 3260, 1340 and 1140 cm$^{-1}$, consistent for a primary sulfonamide. Mass spectrum analysis: calc. 235, found 234 (Mass-1H).

EXAMPLE 3

3-(1,3-Dioxolan-2-yl)-N-[(4-methoxy-6-methyl-1,3,5-triazin-2-yl)aminocarbonyl]-2-thiophenesulfonamide To 0.47 g of 3-(1,3-dioxolan-2-yl)thiophene-2-sulfonamide in 20 ml of acetonitrile was added 0.52 g of phenyl(4-methoxy-6-methyl-1,3,5-triazin-2-yl)carbamate and 0.3 ml of 1,8-diazabicyclo[5.4.0]undec-7-ene (DBU). After stirring at ambient temperatures for two hours the solution was diluted to 50 ml with water and the pH was adjusted to 3 by the addition of hydrochloride acid. The resultant solution was extracted with methylene chloride and the methylene chloride phase was dried over magnesium sulfate, filtered and evaporated. Trituration of the residue with butyl chloride yielded 0.6 g of the product, m.p. 164°–166°. Infrared absorption spectra showed peaks at 1700, 1600 and 1550 cm$^{-1}$, consistent for the desired structure.

NMR(CDCl₃): δ  2.56 (S, CH₃);
4.04 (s, OCH₃);

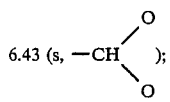

6.43 (s, —CH(O)(O) );

4.95 (t, (CH₂)₂);
7.25 (d, thiophene);
7.58 (d, thiophene).

EXAMPLE 4

N-[4,6-Dimethoxypyrimidin-2-yl)aminocarbonyl]-3-(1,3-dioxolan-2-yl)-2-thiophenesulfonamide To 0.47 g of 3-(1,3-dioxolan-2-yl)thiophene-2-sulfonamide in 20 ml of acetonitrile was added 0.5 g of phenyl (4,6-dimethoxypyrimidin-2-yl)carbamate and 0.3 ml of DBU. After stirring for two hours at ambient temperature, 25 ml of water was added to the mixture and the solution was acidified to pH 3 with 10% hydrochloric acid. The precipitated product was removed by filtration, washed with water and air dried to yield 0.9 g of the subject compound, m.p. 157–168. Infrared absorption peaks at 1700, 1600, 1570 cm$^{-1}$ were consistent for the desired structure.

| NMR(CDCl$_3$): δ | 3.95 (m. CH$_2$O); |
|---|---|
| | 3.95 (s. CH$_3$O); |
| | 5.77 (s. pyrimidine); |
| | 6.44 (s. dioxolane); |
| | 7.25 (d. thiophene); |
| | 7.57 (d. thiophene). |

By using the procedures described in the foregoing equations and examples or modifications thereof, one skilled in the art can prepare the compounds shown in the following tables.

TABLE OF STRUCTURES

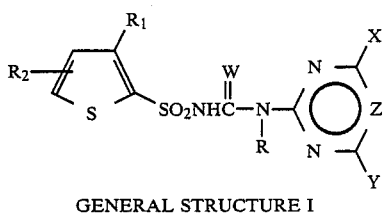

GENERAL STRUCTURE I

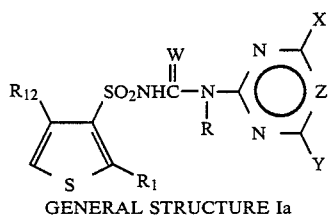

GENERAL STRUCTURE Ia

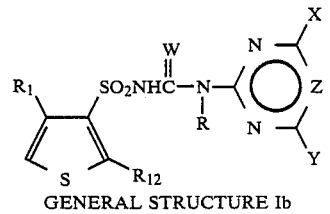

GENERAL STRUCTURE Ib

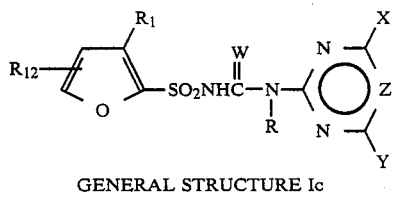

GENERAL STRUCTURE Ic

-continued
TABLE OF STRUCTURES

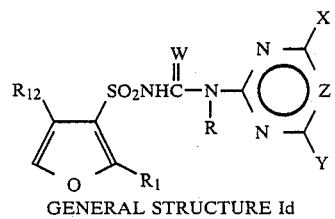

GENERAL STRUCTURE Id

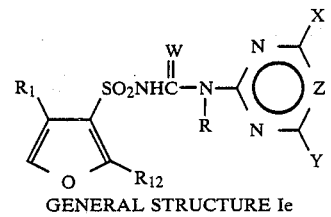

GENERAL STRUCTURE Ie

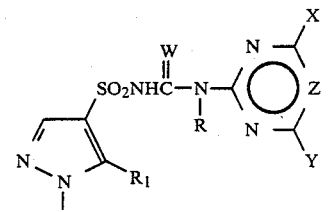

GENERAL STRUCTURE II

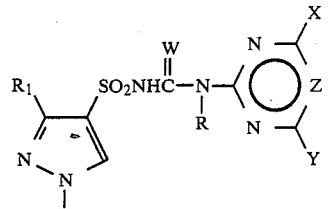

GENERAL STRUCTURE IIa

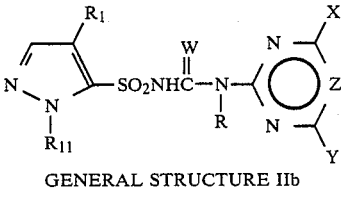

GENERAL STRUCTURE IIb

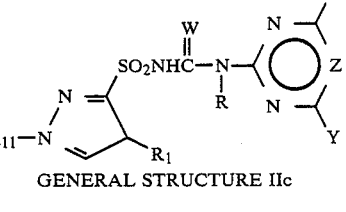

GENERAL STRUCTURE IIc

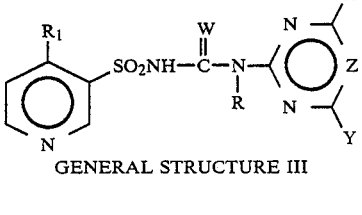

GENERAL STRUCTURE III

-continued
TABLE OF STRUCTURES

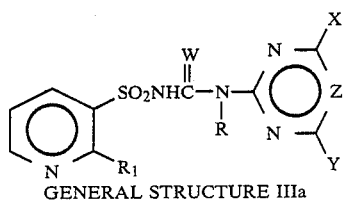
GENERAL STRUCTURE IIIa

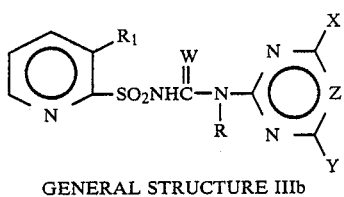
GENERAL STRUCTURE IIIb

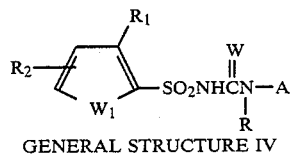
GENERAL STRUCTURE IV

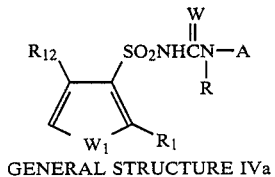
GENERAL STRUCTURE IVa

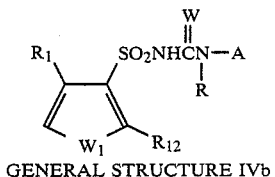
GENERAL STRUCTURE IVb

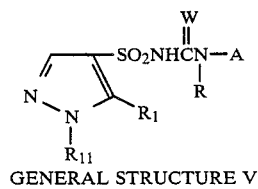
GENERAL STRUCTURE V

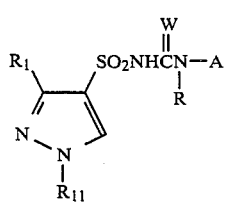

-continued
TABLE OF STRUCTURES

GENERAL STRUCTURE Va

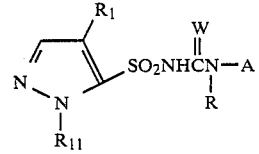
GENERAL STRUCTURE Vb

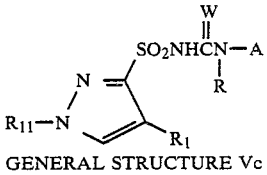
GENERAL STRUCTURE Vc

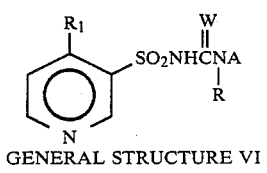
GENERAL STRUCTURE VI

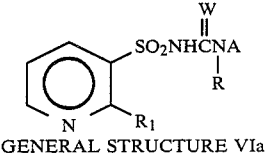
GENERAL STRUCTURE VIa

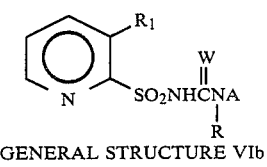
GENERAL STRUCTURE VIb

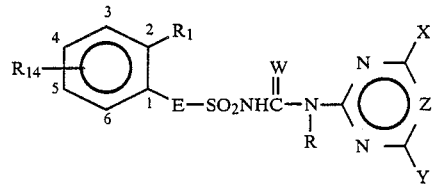
GENERAL STRUCTURE VII

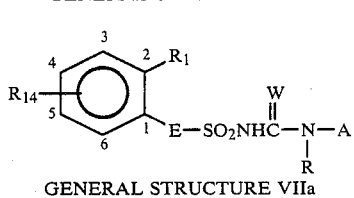
GENERAL STRUCTURE VIIa

TABLE I

| | | | GENERAL STRUCTURE I | | | | |
|---|---|---|---|---|---|---|---|
| $R_1$ | $R_2$ | R | W | X | Y | Z | m.p. °C. |
| 1,3-dixolan-2-yl | H | H | O | $CH_3$ | $CH_3$ | CH | |
| 1,3-dioxolan-2-yl | H | H | O | $CH_3$ | $OCH_3$ | CH | |
| 1,3-dioxolan-2-yl | H | H | O | $OCH_3$ | $OCH_3$ | CH | |
| 1,3-dioxolan-2-yl | H | H | O | $CH_3$ | $CH_3$ | N | |
| 1,3-dioxolan-2-yl | H | H | O | $CH_3$ | $OCH_3$ | N | |
| 1,3-dioxolan-2-yl | H | H | O | $OCH_3$ | $OCH_3$ | N | |
| 1,3-dioxolan-2-yl | H | H | O | Cl | $OCH_3$ | CH | |
| 1,3-dioxolan-2-yl | H | H | O | $OCH_2CH_3$ | $NHCH_3$ | N | |

TABLE I-continued

GENERAL STRUCTURE I

| R₁ | R₂ | R | W | X | Y | Z | m.p. °C. |
|---|---|---|---|---|---|---|---|
| 1,3-dioxolan-2-yl | H | H | O | OCF₂H | CH₃ | CH | |
| 1,3-dioxolan-2-yl | H | H | O | CF₂H | OCH₃ | CH | |
| 1,3-dioxolan-2-yl | H | H | O | CF₂H | OCH₃ | N | |
| 1,3-dioxolan-2-yl | H | H | O | OCH₂CH₂F | CH₃ | N | |
| 1,3-dioxolan-2-yl | H | H | O | OCH₂CHF₂ | CH₃ | N | |
| 1,3-dioxolan-2-yl | H | H | O | OCH₂CF₃ | CH₃ | N | |
| 1,3-dioxolan-2-yl | H | H | O | CF₃ | CH₃ | CH | |
| 1,3-dioxolan-2-yl | H | H | O | CF₃ | OCH₃ | N | |
| 1,3-dioxolan-2-yl | H | H | O | CH₃ | NHCH₃ | N | |
| 1,3-dioxolan-2-yl | H | H | O | OCH₃ | N(CH₃)₂ | N | |
| 1,3-dioxolan-2-yl | H | H | O | OCH₃ | N(CH₃)OCH₃ | N | |
| 1,3-dioxolan-2-yl | H | H | O | OCH₃ | CH₂OCH₃ | N | |
| 1,3-dioxolan-2-yl | H | H | O | CH₃ | CH₂OCH₃ | CH | |
| 1,3-dioxolan-2-yl | H | H | O | CH₃ | SCH₃ | N | |
| 1,3-dioxolan-2-yl | H | H | O | CH₃ | OCH₂CH=CH₂ | N | |
| 1,3-dioxolan-2-yl | H | H | O | CH₃ | OCH₂C≡CH | N | |
| 1,3-dioxolan-2-yl | H | H | O | OCH₃ | CH₂OCH₂CH₃ | N | |
| 1,3-dioxolan-2-yl | H | H | O | CH₃ | CH₂OCH₂CH₃ | N | |
| 1,3-dioxolan-2-yl | H | H | O | CH₃ | OCH₂CH₂OCH₃ | CH | |
| 1,3-dioxolan-2-yl | H | H | O | CH₃ | OCH₂CH₂OCH₃ | N | |
| 1,3-dioxolan-2-yl | H | H | O | CH₃ | CH₂SCH₃ | N | |
| 1,3-dioxolan-2-yl | H | H | O | CH₃ | CH₂SCH₃ | CH | |
| 1,3-dioxolan-2-yl | H | H | O | CH₃ | CH(OCH₃)₂ | CH | |
| 1,3-dioxolan-2-yl | H | H | O | CH₃ | i-C₃H₇ | CH | |
| 1,3-dioxolan-2-yl | H | H | O | CH₃ | CH(OCH₃)₂ | N | |
| 1,3-dioxolan-2-yl | H | H | O | OCH₃ | 1,3-dioxolan-2-yl | CH | |
| 1,3-dioxolan-2-yl | H | H | O | OCH₃ | 1,3-dioxolan-2-2-yl | N | |
| 1,3-dioxolan-2-yl | H | H | O | OCH₃ | 4-methyl-1,3-dioxolan-2-yl | N | |
| 1,3-dioxolan-2-yl | H | H | O | OCH₃ | 4-methyl-1,3-dioxolan-2-yl | CH | |
| 1,3-dioxolan-2-yl | H | H | O | OCH₃ | 4-ethyl-1,3-dioxolan-2-yl | CH | |
| 1,3-dioxolan-2-yl | H | H | O | OCH₃ | 1,3-dioxan-2-yl | N | |
| 1,3-dioxolan-2-yl | H | H | O | OCH₃ | 1,3-dioxan-2-yl | CH | |
| 1,3-dioxolan-2-yl | H | H | O | OCH₃ | cyclopropyl | CH | |
| 1,3-dioxolan-2-yl | H | H | O | OCF₂H | OCF₂H | CH | |
| 1,3-dioxolan-2-yl | H | H | O | Br | OCF₂H | CH | |
| 1,3-dioxolan-2-yl | H | H | O | OCH₃ | cyclopropyl | N | |
| 1,3-dioxolan-2-yl | H | H | O | F | CH₃ | CH | |
| 1,3-dioxolan-2-yl | H | H | O | F | OCH₃ | CH | |
| 1,3-dioxolan-2-yl | H | H | O | Br | OCH₃ | CH | |
| 1,3-dioxolan-2-yl | H | H | O | Br | CH₃ | CH | |
| 1,3-dioxolan-2-yl | H | H | O | I | OCH₃ | CH | |
| 1,3-dioxolan-2-yl | H | H | O | OCH₃ | cyclopropyl | CH | |
| 1,3-dioxolan-2-yl | H | H | O | OCH₂CH₃ | cyclopropyl | N | |
| 1,3-dioxolan-2-yl | H | H | O | OCH₂CH₂F | cyclopropyl | N | |
| 1,3-dioxolan-2-yl | H | H | O | OCH₃ | cyclopropyl | N | |
| 1,3-dioxolan-2-yl | H | H | O | OCH₃ | CH(SCH₃)₂ | N | |
| 1,3-dioxolan-2-yl | H | H | O | OCH₃ | CH(SCH₃)₂ | CH | |
| 1,3-dioxolan-2-yl | H | H | O | OCH₃ | 1,3-dithiolan-2-yl | CH | |
| 1,3-dioxolan-2-yl | H | H | O | OCH₃ | 1,3-dithiolan-2-yl | N | |
| 1,3-dioxolan-2-yl | H | H | O | OCH₃ | 1,3-oxathiolan-2-yl | N | |
| 1,3-dioxolan-2-yl | H | CH₃ | O | OCH₃ | CH₃ | CH | |
| 1,3-dioxolan-2-yl | H | CH₃ | O | OCH₃ | OCH₃ | CH | |
| 1,3-dioxolan-2-yl | H | CH₃ | O | CH₃ | CH₃ | CH | |
| 1,3-dioxolan-2-yl | H | CH₃ | O | CH₃ | CH₃ | N | |
| 1,3-dioxolan-2-yl | H | CH₃ | O | CH₃ | OCH₃ | N | |
| 1,3-dioxolan-2-yl | H | CH₃ | O | OCH₃ | OCH₃ | N | |
| 1,3-dioxolan-2-yl | H | CH₃ | O | Cl | OCH₃ | CH | |
| 1,3-dioxolan-2-yl | H | H | S | CH₃ | OCH₃ | CH | |
| 1,3-dioxolan-2-yl | H | H | S | CH₃ | CH₃ | CH | |
| 1,3-dioxolan-2-yl | H | H | S | OCH₃ | CH₃ | N | |
| 1,3-dioxolan-2-yl | H | H | S | OCH₃ | OCH₃ | N | |
| 1,3-dithiolan-2-yl | H | H | O | OCH₃ | CH₃ | CH | |
| 1,3-dithiolan-2-yl | H | H | O | CH₃ | CH₃ | CH | |
| 1,3-dithiolan-2-yl | H | H | O | Cl | OCH₃ | CH | |
| 1,3-dithiolan-2-yl | H | H | O | OCH₃ | OCH₃ | CH | |
| 1,3-dithiolan-2-yl | H | H | O | OCH₃ | OCH₃ | N | |
| 1,3-dithiolan-2-yl | H | H | O | OCH₃ | CH₃ | N | |
| 1,3-dithiolan-2-yl | H | H | O | OCH₂CF₃ | NHCH₃ | N | |
| 1,3-dithiolan-2-yl | H | H | O | OCH₂CH₂F | NHCH₃ | N | |
| —CH(OCH₃)₂ | H | H | O | CH₃ | CH₃ | CH | |
| —CH(OCH₃)₂ | H | H | O | CH₃ | CH₃ | N | |
| —CH(OCH₃)₂ | H | H | O | CH₃ | OCH₃ | N | 147–165 |

TABLE I-continued

GENERAL STRUCTURE I

| R₁ | R₂ | R | W | X | Y | Z | m.p. °C. |
|---|---|---|---|---|---|---|---|
| —CH(OCH₃)₂ | H | H | O | CH₃ | OCH₃ | CH | |
| —CH(OCH₃)₂ | H | H | O | OCH₃ | OCH₃ | CH | 156–158 |
| —CH(OCH₃)₂ | H | H | O | OCH₃ | OCH₃ | N | 135–139 |
| —CH(OCH₃)₂ | H | H | O | Cl | OCH₃ | CH | 151–154 |
| —C(CH₃)(OCH₃)₂ | H | H | O | CH₃ | CH₃ | CH | |
| —C(CH₃)(OCH₃)₂ | H | H | O | CH₃ | CH₃ | N | |
| —C(CH₃)(OCH₃)₂ | H | H | O | CH₃ | OCH₃ | N | 120–126 |
| —C(CH₃)(OCH₃)₂ | H | H | O | CH₃ | OCH₃ | CH | 141–144 |
| —C(CH₃)(OCH₃)₂ | H | H | O | OCH₃ | OCH₃ | CH | 148–152 |
| —C(CH₃)(OCH₃)₂ | H | H | O | OCH₃ | OCH₃ | N | |
| —C(CH₃)(OCH₃)₂ | H | H | O | Cl | OCH₃ | CH | |
| —CH(OC₂H₅)₂ | H | H | O | CH₃ | CH₃ | CH | |
| —CH(OC₂H₅)₂ | H | H | O | CH₃ | CH₃ | N | |
| —CH(OC₂H₅)₂ | H | H | O | CH₃ | OCH₃ | N | |
| —CH(OC₂H₅)₂ | H | H | O | CH₃ | OCH₃ | CH | |
| —CH(OC₂H₅)₂ | H | H | O | OCH₃ | OCH₃ | CH | |
| —CH(OC₂H₅)₂ | H | H | O | OCH₃ | OCH₃ | N | |
| —CH(SCH₃)₂ | H | H | O | CH₃ | CH₃ | CH | |
| —CH(SCH₃)₂ | H | H | O | CH₃ | CH₃ | N | |
| —CH(SCH₃)₂ | H | H | O | CH₃ | OCH₃ | N | |
| —CH(SCH₃)₂ | H | H | O | OCH₃ | OCH₃ | CH | |
| —CH(SCH₃)₂ | H | H | O | OCH₃ | OCH₃ | N | |
| 2-methyl-1,3-dioxolan-2-yl | H | H | O | CH₃ | CH₃ | CH | |
| 2-methyl-1,3-dioxolan-2-yl | H | H | O | CH₃ | CH₃ | N | |
| 2-methyl-1,3-dioxolan-2-yl | H | H | O | CH₃ | OCH₃ | N | |
| 2-methyl-1,3-dioxolan-2-yl | H | H | O | CH₃ | OCH₃ | CH | |
| 2-methyl-1,3-dioxolan-2-yl | H | H | O | OCH₃ | OCH₃ | CH | |
| 2-methyl-1,3-dioxolan-2-yl | H | H | O | OCH₃ | OCH₃ | N | |
| 2-methyl-1,3-dioxolan-2-yl | H | H | O | Cl | OCH₃ | CH | |
| 2-methyl-1,3-dioxolan-2-yl | H | H | O | Br | OCH₃ | CH | |
| 4-methyl-1,3-dioxolan-2-yl | H | H | O | OC₂H₅ | NHCH₃ | N | |
| 4-methyl-1,3-dioxolan-2-yl | H | H | O | CH₃ | CH₃ | CH | |
| 4-methyl-1,3-dioxolan-2-yl | H | H | O | CH₃ | CH₃ | N | |
| 4-methyl-1,3-dioxolan-2-yl | H | H | O | CH₃ | OCH₃ | N | |
| 4-methyl-1,3-dioxolan-2-yl | H | H | O | CH₃ | OCH₃ | CH | |
| 4-methyl-1,3-dioxolan-2-yl | H | H | O | OCH₃ | OCH₃ | CH | |
| 4-methyl-1,3-dioxolan-2-yl | H | H | O | OCH₃ | OCH₃ | N | |
| 4-methyl-1,3-dioxolan-2-yl | H | H | O | Cl | OCH₃ | CH | |
| 4-methyl-1,3-dioxolan-2-yl | H | H | O | Br | OCH₃ | CH | |
| 1,3-oxathiolan-2-yl | H | H | O | OC₂H₅ | NHCH₃ | N | |
| 1,3-oxathiolan-2-yl | H | H | O | CH₃ | CH₃ | CH | |
| 1,3-oxathiolan-2-yl | H | H | O | CH₃ | CH₃ | N | |
| 1,3-oxathiolan-2-yl | H | H | O | CH₃ | OCH₃ | N | |
| 1,3-oxathiolan-2-yl | H | H | O | CH₃ | OCH₃ | CH | |
| 1,3-oxathiolan-2-yl | H | H | O | OCH₃ | OCH₃ | CH | |
| 1,3-oxathiolan-2-yl | H | H | O | OCH₃ | OCH₃ | N | |
| 1,3-oxathiolan-2-yl | H | H | O | Cl | OCH₃ | CH | |
| 1,3-oxathiolan-2-yl | H | H | O | OC₂H₅ | NHCH₃ | N | |
| 2-methyl-1,3-dithiolan-2-yl | H | H | O | CH₃ | CH₃ | CH | |
| 2-methyl-1,3-dithiolan-2-yl | H | H | O | CH₃ | CH₃ | N | |
| 2-methyl-1,3-dithiolan-2-yl | H | H | O | CH₃ | OCH₃ | N | |
| 2-methyl-1,3-dithiolan-2-yl | H | H | O | CH₃ | OCH₃ | CH | |
| 2-methyl-1,3-dithiolan-2-yl | H | H | O | OCH₃ | OCH₃ | CH | |
| hexahydro-1,3-dimethyl-pyrimidin-2-yl | H | H | O | OCH₃ | OCH₃ | N | |
| hexahydro-1,3-dimethyl-pyrimidin-2-yl | H | H | O | CH₃ | CH₃ | CH | |
| hexahydro-1,3-dimethyl- | H | H | O | CH₃ | CH₃ | N | |

TABLE I-continued

GENERAL STRUCTURE I

| R₁ | R₂ | R | W | X | Y | Z | m.p. °C. |
|---|---|---|---|---|---|---|---|
| pyrimidin-2-yl | | | | | | | |
| hexahydro-1,3-dimethyl-pyrimidin-2-yl | H | H | O | CH₃ | OCH₃ | N | |
| hexahydro-1,3-dimethyl-pyrimidin-2-yl | H | H | O | CH₃ | OCH₃ | CH | |
| hexahydro-1,3-dimethyl-pyrimidin-2-yl | H | H | O | OCH₃ | OCH₃ | CH | |
| hexahydro-1,3-dimethyl-pyrimidin-2-yl | H | H | O | OCH₃ | OCH₃ | N | |
| 4,5-dimethyl-1,3-dioxolan-2-yl | H | H | O | CH₃ | CH₃ | CH | |
| 4,5-dimethyl-1,3-dioxolan-2-yl | H | H | O | CH₃ | CH₃ | N | |
| 4,5-dimethyl-1,3-dioxolan-2-yl | H | H | O | CH₃ | OCH₃ | N | |
| 4,5-dimethyl-1,3-dioxolan-2-yl | H | H | O | CH₃ | OCH₃ | CH | |
| 4,5-dimethyl-1,3-dioxolan-2-yl | H | H | O | OCH₃ | OCH₃ | CH | |
| 4-ethyl-1,3-dioxolan-2-yl | H | H | O | CH₃ | CH₃ | CH | |
| 4-ethyl-1,3-dioxolan-2-yl | H | H | O | CH₃ | CH₃ | N | |
| 4-ethyl-1,3-dioxolan-2-yl | H | H | O | CH₃ | OCH₃ | N | |
| 4-ethyl-1,3-dioxolan-2-yl | H | H | O | CH₃ | OCH₃ | CH | |
| 4-ethyl-1,3-dioxolan-2-yl | H | H | O | OCH₃ | OCH₃ | CH | |
| 1,3-dimethyl-2-imidazolinyl | H | H | O | OCH₃ | OCH₃ | N | |
| 1,3-dimethyl-2-imidazolinyl | H | H | O | CH₃ | CH₃ | CH | |
| 1,3-dimethyl-2-imidazolinyl | H | H | O | CH₃ | CH₃ | N | |
| 1,3-dimethyl-2-imidazolinyl | H | H | O | CH₃ | OCH₃ | N | |
| 1,3-dimethyl-2-imidazolinyl | H | H | O | CH₃ | OCH₃ | CH | |
| 1,3-dimethyl-2-imidazolinyl | H | H | O | OCH₃ | OCH₃ | CH | |
| 1,3-dioxolan-2-yl | 5-CH₃ | H | O | CH₃ | CH₃ | CH | |
| 1,3-dioxolan-2-yl | 5-CH₃ | H | O | OCH₃ | CH₃ | CH | |
| 1,3-dioxolan-2-yl | 5-CH₃ | H | O | OCH₃ | OCH₃ | CH | |
| 1,3-dioxolan-2-yl | 4-CH₃ | H | O | OCH₃ | OCH₃ | N | |
| 1,3-dioxolan-2-yl | 4-CH₃ | H | O | OCH₃ | CH₃ | N | |
| 1,3-dioxolan-2-yl | 4-CH₃ | H | O | CH₃ | CH₃ | N | |
| —C(OCH₃)₃ | H | H | O | OCH₃ | OCH₃ | CH | |
| —C(OCH₃)₃ | H | H | O | CH₃ | OCH₃ | CH | |
| —C(OCH₃)₃ | H | H | O | CH₃ | CH₃ | CH | |
| —C(OCH₃)₃ | H | H | O | Cl | OCH₃ | CH | |
| —C(OCH₃)₃ | H | H | O | Br | OCH₃ | CH | |
| —C(OCH₃)₃ | H | H | O | CH₃ | H | CH | |
| —C(OCH₃)₃ | H | H | O | OCH₃ | H | CH | |
| —C(OCH₃)₃ | H | H | O | OCH₃ | CH₂OC₂H₅ | CH | |
| —C(OCH₃)₃ | H | H | O | OCF₂H | OCH₃ | CH | |
| —C(OCH₃)₃ | H | H | O | OCH₃ | CH(OCH₃)₂ | CH | |
| —C(OCH₃)₃ | H | H | O | CH₃ | OC₂H₅ | CH | |
| —C(OCH₃)₃ | H | H | O | CH₃ | CH₂OCH₃ | CH | |
| —C(OCH₃)₃ | H | H | O | OCH₃ | CH₂OCH₃ | CH | |
| —C(OCH₃)₃ | H | H | O | OCH₃ | C₂H₅ | CH | |
| —C(OCH₃)₃ | H | H | O | Cl | OC₂H₅ | CH | |
| —C(OCH₃)₃ | H | H | O | OCH₂CH₃ | NHCH₃ | N | |
| —C(OCH₃)₃ | H | H | O | OCF₂H | CH₃ | CH | |
| —C(OCH₃)₃ | H | H | O | CF₂H | OCH₃ | CH | |
| —C(OCH₃)₃ | H | H | O | CF₂H | OCH₃ | N | |
| —C(OCH₃)₃ | H | H | O | OCH₃ | cyclopropyl | N | |
| —C(OCH₃)₃ | H | H | O | OCF₂H | OCF₂H | CH | |
| —C(OCH₃)₃ | H | H | O | CH₃ | OCH₃ | N | |
| —C(OCH₃)₃ | H | H | O | CH₃ | CH₃ | N | |
| —C(OC₂H₅)(OCH₃)₂ | H | H | O | OCH₃ | OCH₃ | CH | |
| 2-methoxy-1,3-dioxolan-2-yl | H | H | O | OCH₃ | OCH₃ | CH | |
| —C(OC₂H₅)₃ | H | H | O | OCH₃ | OCH₃ | CH | |
| —C(OC₂H₅)₃ | H | H | O | CH₃ | OCH₃ | CH | |
| —C(OC₂H₅)₃ | H | H | O | CH₃ | CH₃ | CH | |
| —C(OC₂H₅)₃ | H | H | O | Cl | OCH₃ | CH | |
| —C(OC₂H₅)₃ | H | H | O | Br | OCH₃ | CH | |

TABLE I-continued

GENERAL STRUCTURE I

| R₁ | R₂ | R | W | X | Y | Z | m.p. °C. |
|---|---|---|---|---|---|---|---|
| —C(OC₂H₅)₃ | H | H | O | CH₃ | H | CH | |
| —C(OC₂H₅)₃ | H | H | O | OCH₃ | H | CH | |
| —C(OC₂H₅)₃ | H | H | O | OCH₃ | CH₂OC₂H₅ | CH | |
| —C(OC₂H₅)₃ | H | H | O | OCF₂H | OCH₃ | CH | |
| —C(OC₂H₅)₃ | H | H | O | OCH₃ | CH(OCH₃)₂ | CH | |
| —C(OC₂H₅)₃ | H | H | O | CH₃ | OC₂H₅ | CH | |
| —C(OC₂H₅)₃ | H | H | O | CH₃ | CH₂OCH₃ | CH | |
| —C(OC₂H₅)₃ | H | H | O | OCH₃ | CH₂OCH₃ | CH | |
| —C(OC₂H₅)₃ | H | H | O | OCH₃ | C₂H₅ | CH | |
| —C(OC₂H₅)₃ | H | H | O | Cl | OC₂H₅ | CH | |
| —C(OC₂H₅)₃ | H | H | O | OCH₂CH₃ | NHCH₃ | N | |
| —C(OC₂H₅)₃ | H | H | O | OCF₂H | CH₃ | CH | |
| —C(OC₂H₅)₃ | H | H | O | CF₂H | OCH₃ | CH | |
| —C(OC₂H₅)₃ | H | H | O | CF₂H | OCH₃ | N | |
| —C(OC₂H₅)₃ | H | H | O | OCH₃ | cyclo-propyl | N | |
| —C(OC₂H₅)₃ | H | H | O | OCF₂H | OCF₂H | CH | |
| —C(OC₂H₅)₃ | H | H | O | CH₃ | OCH₃ | N | |
| —C(OC₂H₅)₃ | H | H | O | OCH₃ | OCH₃ | N | |
| —C(OC₂H₅)₃ | H | H | O | CH₃ | CH₃ | N | |
| —C(OCH₃)(OCH₂H₅)₂ | H | H | O | OCH₃ | OCH₃ | CH | |
| 2-ethoxy-1,3-dioxolan-2-yl | H | H | O | OCH₃ | OCH₃ | CH | |
| —C(OCH₂CH₂CH₃)₃ | H | H | O | CH₃ | OCH₃ | CH | |
| —C(OCH₂CH₂CH₃)₃ | H | H | O | CH₃ | CH₃ | CH | |
| —C(OCH₂CH₂CH₃)₃ | H | H | O | Cl | OCH₃ | CH | |
| —C(OCH₂CH₂CH₃)₃ | H | H | O | CH₃ | OCH₃ | N | |
| —C(OCH₂CH₂CH₃)₃ | H | H | O | OCH₃ | OCH₃ | N | |
| —C(C₂H₅)(OCH₃)₂ | H | H | O | OCH₃ | OCH₃ | CH | |
| —C(C₂H₅)(OCH₃)₂ | H | H | O | CH₃ | OCH₃ | CH | |
| —C(C₂H₅)(OCH₃)₂ | H | H | O | CH₃ | CH₃ | CH | |
| —C(C₂H₅)(OCH₃)₂ | H | H | O | CH₃ | OCH₃ | N | |
| —C(C₂H₅)(OCH₃)₂ | H | H | O | OCH₃ | OCH₃ | N | |
| —C(n-C₃H₇)(OCH₃)₂ | H | H | O | OCH₃ | OCH₃ | CH | |
| 2-ethyl-1,3-dioxolan-2-yl | H | H | O | OCH₃ | OCH₃ | CH | |
| 2-ethyl-1,3-dioxolan-2-yl | H | H | O | CH₃ | OCH₃ | CH | |
| 2-ethyl-1,3-dioxolan-2-yl | H | H | O | CH₃ | OCH₃ | N | |
| 2-propyl-1,3-dioxolan-2-yl | H | H | O | OCH₃ | OCH₃ | CH | |
| 2-propyl-1,3-dioxolan-2-yl | H | H | O | CH₃ | OCH₃ | CH | |
| 2-propyl-1,3-dioxolan-2-yl | H | H | O | CH₃ | OCH₃ | N | |
| 1,3-dioxolan-2-yl | H | H | O | OCH₃ | C≡CH | CH | |
| 1,3-dioxolan-2-yl | H | H | O | OCH₃ | CF₃ | CH | |
| 1,3-dioxolan-2-yl | H | H | O | OCH₃ | SCF₂H | CH | |
| 1,3-dioxolan-2-yl | H | H | O | CH₂F | OCH₃ | CH | |
| 1,3-dioxolan-2-yl | H | H | O | OCH₃ | H | CH | |
| 1,3-dioxolan-2-yl | H | H | O | CH₃ | OC₂H₅ | CH | |
| C(OCH₃)₃ | H | H | O | F | OCH₃ | CH | |
| C(OCH₃)₃ | H | H | O | I | OCH₃ | CH | |
| C(OCH₃)₃ | H | H | O | OCH₃ | C≡CH | CH | |

TABLE Ia

GENERAL STRUCTURE Ia

| R₁ | R₁₂ | R | W | X | Y | Z | m.p. °C. |
|---|---|---|---|---|---|---|---|
| 1,3-dioxolan-2-yl | H | H | O | CH₃ | CH₃ | CH | |
| 1,3-dioxolan-2-yl | H | H | O | CH₃ | OCH₃ | CH | |
| 1,3-dioxolan-2-yl | H | H | O | OCH₃ | OCH₃ | CH | |
| 1,3-dioxolan-2-yl | H | H | O | CH₃ | CH₃ | N | |
| 1,3-dioxolan-2-yl | H | H | O | CH₃ | OCH₃ | N | |
| 1,3-dioxolan-2-yl | H | H | O | OCH₃ | OCH₃ | N | |
| 1,3-dioxolan-2-yl | H | H | O | Cl | OCH₃ | CH | |
| 1,3-dioxolan-2-yl | H | H | O | OCH₂CH₃ | NHCH₃ | N | |
| 1,3-dioxolan-2-yl | H | H | O | OCF₂H | CH₃ | CH | |
| 1,3-dioxolan-2-yl | H | H | O | CF₂H | OCH₃ | CH | |
| 1,3-dioxolan-2-yl | H | H | O | CF₂H | OCH₃ | N | |
| 1,3-dioxolan-2-yl | H | H | O | OCH₂CH₂F | CH₃ | N | |
| 1,3-dioxolan-2-yl | H | H | O | OCH₂CHF₂ | CH₃ | N | |
| 1,3-dioxolan-2-yl | H | H | O | OCH₂CF₃ | CH₃ | N | |
| 1,3-dioxolan-2-yl | H | H | O | CF₃ | CH₃ | CH | |
| 1,3-dioxolan-2-yl | H | H | O | CF₃ | OCH₃ | N | |
| 1,3-dioxolan-2-yl | H | H | O | CH₃ | NHCH₃ | N | |

TABLE Ia-continued

GENERAL STRUCTURE Ia

| $R_1$ | $R_{12}$ | R | W | X | Y | Z | m.p. °C. |
|---|---|---|---|---|---|---|---|
| 1,3-dioxolan-2-yl | H | H | O | $OCH_3$ | $N(CH_3)_2$ | N | |
| 1,3-dioxolan-2-yl | H | H | O | $OCH_3$ | $N(CH_3)OCH_3$ | N | |
| 1,3-dioxolan-2-yl | H | H | O | $OCH_3$ | $CH_2OCH_3$ | N | |
| 1,3-dioxolan-2-yl | H | H | O | $CH_3$ | $CH_2OCH_3$ | CH | |
| 1,3-dioxolan-2-yl | H | H | O | $CH_3$ | $SCH_3$ | N | |
| 1,3-dioxolan-2-yl | H | H | O | $CH_3$ | $OCH_2CH=CH_2$ | N | |
| 1,3-dioxolan-2-yl | H | H | O | $CH_3$ | $OCH_2C\equiv CH$ | N | |
| 1,3-dioxolan-2-yl | H | H | O | $OCH_3$ | $CH_2OCH_2CH_3$ | N | |
| 1,3-dioxolan-2-yl | H | H | O | $CH_3$ | $CH_2OC_2H_5$ | N | |
| 1,3-dioxolan-2-yl | H | H | O | $CH_3$ | $OCH_2CH_2OCH_3$ | CH | |
| 1,3-dioxolan-2-yl | H | H | O | $CH_3$ | $OCH_2CH_2OCH_3$ | N | |
| 1,3-dioxolan-2-yl | H | H | O | $CH_3$ | $CH_2SCH_3$ | N | |
| 1,3-dioxolan-2-yl | H | H | O | $CH_3$ | $CH_2SCH_3$ | CH | |
| 1,3-dioxolan-2-yl | H | H | O | $CH_3$ | $CH(OCH_3)_2$ | CH | |
| 1,3-dioxolan-2-yl | H | H | O | $CH_3$ | $i\text{-}C_3H_7$ | CH | |
| 1,3-dioxolan-2-yl | H | H | O | $CH_3$ | $CH(OCH_3)_2$ | N | |
| 1,3-dioxolan-2-yl | H | H | O | $OCH_3$ | 1,3-dioxolan-2-yl | CH | |
| 1,3-dioxolan-2-yl | H | H | O | $OCH_3$ | 1,3-dioxolan-2-yl | N | |
| 1,3-dioxolan-2-yl | H | H | O | $OCH_3$ | 4-methyl-1,3-dioxolan-2-yl | N | |
| 1,3-dioxolan-2-yl | H | H | O | $OCH_3$ | 4-methyl-1,3-dioxolan-2-yl | CH | |
| 1,3-dioxolan-2-yl | H | H | O | $OCH_3$ | 4-ethyl-1,3-dioxolan-2-yl | CH | |
| 1,3-dioxolan-2-yl | H | H | O | $OCH_3$ | 1,3-dioxan-2-yl | N | |
| 1,3-dioxolan-2-yl | H | H | O | $OCH_3$ | 1,3-dioxan-2-yl | CH | |
| 1,3-dioxolan-2-yl | H | H | O | $OCH_3$ | cyclopropyl | CH | |
| 1,3-dioxolan-2-yl | H | H | O | $OCF_2H$ | $OCF_2H$ | CH | |
| 1,3-dioxolan-2-yl | H | H | O | Br | $OCF_2H$ | CH | |
| 1,3-dioxolan-2-yl | H | H | O | $OCH_3$ | cyclopropyl | N | |
| 1,3-dioxolan-2-yl | H | H | O | F | $CH_3$ | CH | |
| 1,3-dioxolan-2-yl | H | H | O | F | $OCH_3$ | CH | |
| 1,3-dioxolan-2-yl | H | H | O | Br | $OCH_3$ | CH | |
| 1,3-dioxolan-2-yl | H | H | O | Br | $CH_3$ | CH | |
| 1,3-dioxolan-2-yl | H | H | O | I | $OCH_3$ | CH | |
| 1,3-dioxolan-2-yl | H | H | O | $OCH_3$ | cyclopropyl | CH | |
| 1,3-dioxolan-2-yl | H | H | O | $OCH_2CH_3$ | cyclopropyl | N | |
| 1,3-dioxolan-2-yl | H | H | O | $OCH_2CH_2F$ | cyclopropyl | N | |
| 1,3-dioxolan-2-yl | H | H | O | $OCH_3$ | cyclopropyl | N | |
| 1,3-dioxolan-2-yl | H | H | O | $OCH_3$ | $CH(SCH_3)_2$ | N | |
| 1,3-dioxolan-2-yl | H | H | O | $OCH_3$ | $CH(SCH_3)_2$ | CH | |
| 1,3-dioxolan-2-yl | H | H | O | $OCH_3$ | 1,3-dithiolan-2-yl | CH | |
| 1,3-dioxolan-2-yl | H | H | O | $OCH_3$ | 1,3-dithiolan-2-yl | N | |
| 1,3-dioxolan-2-yl | H | H | O | $OCH_3$ | 1,3-oxathiolan-2-yl | N | |
| 1,3-dioxolan-2-yl | H | $CH_3$ | O | $OCH_3$ | $CH_3$ | CH | |
| 1,3-dioxolan-2-yl | H | $CH_3$ | O | $OCH_3$ | $OCH_3$ | CH | |
| 1,3-dioxolan-2-yl | H | $CH_3$ | O | $CH_3$ | $CH_3$ | CH | |
| 1,3-dioxolan-2-yl | H | $CH_3$ | O | $CH_3$ | $CH_3$ | N | |
| 1,3-dioxolan-2-yl | H | $CH_3$ | O | $CH_3$ | $OCH_3$ | N | |
| 1,3-dioxolan-2-yl | H | $CH_3$ | O | $OCH_3$ | $OCH_3$ | N | |
| 1,3-dioxolan-2-yl | H | $CH_3$ | O | Cl | $OCH_3$ | CH | |
| 1,3-dioxolan-2-yl | H | H | S | $CH_3$ | $OCH_3$ | CH | |
| 1,3-dioxolan-2-yl | H | H | S | $CH_3$ | $CH_3$ | CH | |
| 1,3-dioxolan-2-yl | H | H | S | $OCH_3$ | $CH_3$ | N | |
| 1,3-dioxolan-2-yl | H | H | S | $OCH_3$ | $OCH_3$ | N | |
| 1,3-dithiolan-2-yl | H | H | O | $OCH_3$ | $CH_3$ | CH | |
| 1,3-dithiolan-2-yl | H | H | O | $CH_3$ | $CH_3$ | CH | |
| 1,3-dithiolan-2-yl | H | H | O | Cl | $OCH_3$ | CH | |
| 1,3-dithiolan-2-yl | H | H | O | $OCH_3$ | $OCH_3$ | CH | |
| 1,3-dithiolan-2-yl | H | H | O | $OCH_3$ | $OCH_3$ | N | |
| 1,3-dithiolan-2-yl | H | H | O | $OCH_3$ | $CH_3$ | N | |
| 1,3-dithiolan-2-yl | H | H | O | $OCH_2CF_3$ | $NHCH_3$ | N | |
| 1,3-dithiolan-2-yl | H | H | O | $OCH_2CH_2F$ | $NHCH_3$ | N | |
| —$CH(OCH_3)_2$ | H | H | O | $CH_3$ | $CH_3$ | CH | |
| —$CH(OCH_3)_2$ | H | H | O | $CH_3$ | $CH_3$ | N | |
| —$CH(OCH_3)_2$ | H | H | O | $CH_3$ | $OCH_3$ | N | |
| —$CH(OCH_3)_2$ | H | H | O | $CH_3$ | $OCH_3$ | CH | |
| —$CH(OCH_3)_2$ | H | H | O | $OCH_3$ | $OCH_3$ | CH | |
| —$CH(OCH_3)_2$ | H | H | O | $OCH_3$ | $OCH_3$ | N | |
| —$CH(OCH_3)_2$ | H | H | O | Cl | $OCH_3$ | CH | |
| —$C(CH_3)(OCH_3)_2$ | H | H | O | $CH_3$ | $CH_3$ | CH | |
| —$C(CH_3)(OCH_3)_2$ | H | H | O | $CH_3$ | $CH_3$ | N | |
| —$C(CH_3)(OCH_3)_2$ | H | H | O | $CH_3$ | $OCH_3$ | N | |
| —$C(CH_3)(OCH_3)_2$ | H | H | O | $CH_3$ | $OCH_3$ | CH | |
| —$C(CH_3)(OCH_3)_2$ | H | H | O | $OCH_3$ | $OCH_3$ | CH | |
| —$C(CH_3)(OCH_3)_2$ | H | H | O | $OCH_3$ | $OCH_3$ | N | |
| —$C(CH_3)(OCH_3)_2$ | H | H | O | Cl | $OCH_3$ | CH | |
| —$CH(OC_2H_5)_2$ | H | H | O | $CH_3$ | $CH_3$ | CH | |
| —$CH(OC_2H_5)_2$ | H | H | O | $CH_3$ | $CH_3$ | N | |
| —$CH(OC_2H_5)_2$ | H | H | O | $CH_3$ | $OCH_3$ | N | |

TABLE Ia-continued

GENERAL STRUCTURE Ia

| R₁ | R₁₂ | R | W | X | Y | Z | m.p. °C. |
|---|---|---|---|---|---|---|---|
| —CH(OC₂H₅)₂ | H | H | O | CH₃ | OCH₃ | CH | |
| —CH(OC₂H₅)₂ | H | H | O | OCH₃ | OCH₃ | CH | |
| —CH(OC₂H₅)₂ | H | H | O | OCH₃ | OCH₃ | N | |
| —CH(SCH₃)₂ | H | H | O | CH₃ | CH₃ | CH | |
| —CH(SCH₃)₂ | H | H | O | CH₃ | CH₃ | N | |
| —CH(SCH₃)₂ | H | H | O | CH₃ | OCH₃ | N | |
| —CH(SCH₃)₂ | H | H | O | OCH₃ | OCH₃ | CH | |
| —CH(SCH₃)₂ | H | H | O | OCH₃ | OCH₃ | N | |
| 2-methyl-1,3-dioxolan-2-yl | H | H | O | CH₃ | CH₃ | CH | |
| 2-methyl-1,3-dioxolan-2-yl | H | H | O | CH₃ | CH₃ | N | |
| 2-methyl-1,3-dioxolan-2-yl | H | H | O | CH₃ | OCH₃ | N | |
| 2-methyl-1,3-dioxolan-2-yl | H | H | O | CH₃ | OCH₃ | CH | |
| 2-methyl-1,3-dioxolan-2-yl | H | H | O | OCH₃ | OCH₃ | CH | |
| 2-methyl-1,3-dioxolan-2-yl | H | H | O | OCH₃ | OCH₃ | N | |
| 2-methyl-1,3-dioxolan-2-yl | H | H | O | Cl | OCH₃ | CH | |
| 2-methyl-1,3-dioxolan-2-yl | H | H | O | Br | OCH₃ | CH | |
| 4-methyl-1,3-dioxolan-2-yl | H | H | O | OC₂H₅ | NHCH₃ | N | |
| 4-methyl-1,3-dioxolan-2-yl | H | H | O | CH₃ | CH₃ | CH | |
| 4-methyl-1,3-dioxolan-2-yl | H | H | O | CH₃ | CH₃ | N | |
| 4-methyl-1,3-dioxolan-2-yl | H | H | O | CH₃ | OCH₃ | N | |
| 4-methyl-1,3-dioxolan-2-yl | H | H | O | CH₃ | OCH₃ | CH | |
| 4-methyl-1,3-dioxolan-2-yl | H | H | O | OCH₃ | OCH₃ | CH | |
| 4-methyl-1,3-dioxolan-2-yl | H | H | O | OCH₃ | OCH₃ | N | |
| 4-methyl-1,3-dioxolan-2-yl | H | H | O | Cl | OCH₃ | CH | |
| 4-methyl-1,3-dioxolan-2-yl | H | H | O | Br | OCH₃ | CH | |
| 1,3-oxathiolan-2-yl | H | H | O | OC₂H₅ | NHCH₃ | N | |
| 1,3-oxathiolan-2-yl | H | H | O | CH₃ | CH₃ | CH | |
| 1,3-oxathiolan-2-yl | H | H | O | CH₃ | CH₃ | N | |
| 1,3-oxathiolan-2-yl | H | H | O | CH₃ | OCH₃ | N | |
| 1,3-oxathiolan-2-yl | H | H | O | CH₃ | OCH₃ | CH | |
| 1,3-oxathiolan-2-yl | H | H | O | OCH₃ | OCH₃ | CH | |
| 1,3-oxathiolan-2-yl | H | H | O | OCH₃ | OCH₃ | N | |
| 1,3-oxathiolan-2-yl | H | H | O | Cl | OCH₃ | CH | |
| 1,3-oxathiolan-2-yl | H | H | O | OC₂H₅ | NHCH₃ | N | |
| 2-methyl-1,3-dithiolan-2-yl | H | H | O | CH₃ | CH₃ | CH | |
| 2-methyl-1,3-dithiolan-2-yl | H | H | O | CH₃ | CH₃ | N | |
| 2-methyl-1,3-dithiolan-2-yl | H | H | O | CH₃ | OCH₃ | N | |
| 2-methyl-1,3-dithiolan-2-yl | H | H | O | CH₃ | OCH₃ | CH | |
| 2-methyl-1,3-dithiolan-2-yl | H | H | O | OCH₃ | OCH₃ | CH | |
| hexahydro-1,3-dimethyl-pyrimidin-2-yl | H | H | O | OCH₃ | OCH₃ | N | |
| hexahydro-1,3-dimethyl-pyrimidin-2-yl | H | H | O | CH₃ | CH₃ | CH | |
| hexahydro-1,3-dimethyl-pyrimidin-2-yl | H | H | O | CH₃ | CH₃ | N | |
| hexahydro-1,3-dimethyl-pyrimidin-2-yl | H | H | O | CH₃ | OCH₃ | N | |
| hexahydro-1,3-dimethyl-pyrimidin-2-yl | H | H | O | CH₃ | OCH₃ | CH | |
| hexahydro-1,3-dimethyl-pyrimidin-2-yl | H | H | O | OCH₃ | OCH₃ | CH | |
| hexahydro-1,3-dimethyl-pyrimidin-2-yl | H | H | O | OCH₃ | OCH₃ | N | |
| 4,5-dimethyl-1,3-dioxolan-2-yl | H | H | O | CH₃ | CH₃ | CH | |
| 4,5-dimethyl-1,3-dioxolan-2-yl | H | H | O | CH₃ | CH₃ | N | |
| 4,5-dimethyl-1,3- | H | H | O | CH₃ | OCH₃ | N | |

TABLE Ia-continued

GENERAL STRUCTURE Ia

| R₁ | R₁₂ | R | W | X | Y | Z | m.p. °C |
|---|---|---|---|---|---|---|---|
| dioxolan-2-yl | | | | | | | |
| 4,5-dimethyl-1,3-dioxolan-2-yl | H | H | O | CH₃ | OCH₃ | CH | |
| 4,5-dimethyl-1,3-dioxolan-2-yl | H | H | O | OCH₃ | OCH₃ | CH | |
| 4-ethyl-1,3-dioxolan-2-yl | H | H | O | CH₃ | CH₃ | CH | |
| 4-ethyl-1,3-dioxolan-2-yl | H | H | O | CH₃ | CH₃ | N | |
| 4-ethyl-1,3-dioxolan-2-yl | H | H | O | CH₃ | OCH₃ | N | |
| 4-ethyl-1,3-dioxolan-2-yl | H | H | O | CH₃ | OCH₃ | CH | |
| 4-ethyl-1,3-dioxolan-2-yl | H | H | O | OCH₃ | OCH₃ | CH | |
| 1,3-dimethyl-2-imidazolinyl | H | H | O | OCH₃ | OCH₃ | N | |
| 1,3-dimethyl-2-imidazolinyl | H | H | O | CH₃ | CH₃ | CH | |
| 1,3-dimethyl-2-imidazolinyl | H | H | O | CH₃ | CH₃ | N | |
| 1,3-dimethyl-2-imidazolinyl | H | H | O | CH₃ | OCH₃ | N | |
| 1,3-dimethyl-2-imidazolinyl | H | H | O | CH₃ | OCH₃ | CH | |
| 1,3-dimethyl-2-imidazolinyl | H | H | O | OCH₃ | OCH₃ | CH | |
| 1,3-dioxolan-2-yl | CH₃ | H | O | CH₃ | CH₃ | CH | |
| 1,3-dioxolan-2-yl | CH₃ | H | O | OCH₃ | CH₃ | CH | |
| 1,3-dioxolan-2-yl | CH₃ | H | O | OCH₃ | OCH₃ | CH | |
| 1,3-dioxolan-2-yl | CH₃ | H | O | OCH₃ | OCH₃ | N | |
| 1,3-dioxolan-2-yl | CH₃ | H | O | OCH₃ | CH₃ | N | |
| 1,3-dioxolan-2-yl | CH₃ | H | O | CH₃ | CH₃ | N | |
| —C(OCH₃)₃ | H | H | O | OCH₃ | OCH₃ | CH | |
| —C(OCH₃)₃ | H | H | O | CH₃ | OCH₃ | CH | |
| —C(OCH₃)₃ | H | H | O | CH₃ | CH₃ | CH | |
| —C(OCH₃)₃ | H | H | O | Cl | OCH₃ | CH | |
| —C(OCH₃)₃ | H | H | O | Br | OCH₃ | CH | |
| —C(OCH₃)₃ | H | H | O | CH₃ | H | CH | |
| —C(OCH₃)₃ | H | H | O | OCH₃ | H | CH | |
| —C(OCH₃)₃ | H | H | O | OCH₃ | CH₂OC₂H₅ | CH | |
| —C(OCH₃)₃ | H | H | O | OCF₂H | OCH₃ | CH | |
| —C(OCH₃)₃ | H | H | O | OCH₃ | CH(OCH₃)₂ | CH | |
| —C(OCH₃)₃ | H | H | O | CH₃ | OC₂H₅ | CH | |
| —C(OCH₃)₃ | H | H | O | CH₃ | CH₂OCH₃ | CH | |
| —C(OCH₃)₃ | H | H | O | OCH₃ | CH₂OCH₃ | CH | |
| —C(OCH₃)₃ | H | H | O | OCH₃ | C₂H₅ | CH | |
| —C(OCH₃)₃ | H | H | O | Cl | OC₂H₅ | CH | |
| —C(OCH₃)₃ | H | H | O | OCH₂CH₃ | NHCH₃ | N | |
| —C(OCH₃)₃ | H | H | O | OCF₂H | CH₃ | CH | |
| —C(OCH₃)₃ | H | H | O | CF₂H | OCH₃ | CH | |
| —C(OCH₃)₃ | H | H | O | CF₂H | OCH₃ | N | |
| —C(OCH₃)₃ | H | H | O | OCH₃ | cyclopropyl | N | |
| —C(OCH₃)₃ | H | H | O | OCF₂H | OCF₂H | CH | |
| —C(OCH₃)₃ | H | H | O | CH₃ | OCH₃ | N | |
| —C(OCH₃)₃ | H | H | O | OCH₃ | OCH₃ | N | |
| —C(OCH₃)₃ | H | H | O | CH₃ | CH₃ | N | |
| —C(OC₂H₅)₃ | H | H | O | OCH₃ | OCH₃ | CH | |
| —C(OC₂H₅)₃ | H | H | O | CH₃ | OCH₃ | CH | |
| —C(OC₂H₅)₃ | H | H | O | CH₃ | CH₃ | CH | |
| —C(OC₂H₅)₃ | H | H | O | Cl | OCH₃ | CH | |
| —C(OC₂H₅)₃ | H | H | O | Br | OCH₃ | CH | |
| —C(OC₂H₅)₃ | H | H | O | CH₃ | H | CH | |
| —C(OC₂H₅)₃ | H | H | O | OCH₃ | H | CH | |
| —C(OC₂H₅)₃ | H | H | O | OCH₃ | CH₂OC₂H₅ | CH | |
| —C(OC₂H₅)₃ | H | H | O | OCF₂H | OCH₃ | CH | |
| —C(OC₂H₅)₃ | H | H | O | OCH₃ | CH(OCH₃)₂ | CH | |
| —C(OC₂H₅)₃ | H | H | O | CH₃ | OC₂H₅ | CH | |
| —C(OC₂H₅)₃ | H | H | O | CH₃ | CH₂OCH₃ | CH | |
| —C(OC₂H₅)₃ | H | H | O | OCH₃ | CH₂OCH₃ | CH | |
| —C(OC₂H₅)₃ | H | H | O | OCH₃ | C₂H₅ | CH | |
| —C(OC₂H₅)₃ | H | H | O | Cl | OC₂H₅ | CH | |
| —C(OC₂H₅)₃ | H | H | O | OCH₂CH₃ | NHCH₃ | N | |
| —C(OC₂H₅)₃ | H | H | O | OCF₂H | CH₃ | CH | |
| —C(OC₂H₅)₃ | H | H | O | CF₂H | OCH₃ | CH | |
| —C(OC₂H₅)₃ | H | H | O | CF₂H | OCH₃ | N | |
| —C(OC₂H₅)₃ | H | H | O | OCH₃ | cyclopropyl | N | |
| —C(OC₂H₅)₃ | H | H | O | OCF₂H | OCF₂H | CH | |

TABLE Ia-continued

GENERAL STRUCTURE Ia

| R₁ | R₁₂ | R | W | X | Y | Z | m.p. °C. |
|---|---|---|---|---|---|---|---|
| —C(OC₂H₅)₃ | H | H | O | CH₃ | OCH₃ | N | |
| —C(OC₂H₅)₃ | H | H | O | OCH₃ | OCH₃ | N | |
| —C(OC₂H₅)₃ | H | H | O | CH₃ | CH₃ | N | |
| —C(OCH₂CH₂CH₃)₃ | H | H | O | OCH₃ | OCH₃ | CH | |
| —C(OCH₂CH₂CH₃)₃ | H | H | O | CH₃ | OCH₃ | CH | |
| —C(OCH₂CH₂CH₃)₃ | H | H | O | CH₃ | CH₃ | CH | |
| —C(OCH₂CH₂CH₃)₃ | H | H | O | Cl | OCH₃ | CH | |
| —C(OCH₂CH₂CH₃)₃ | H | H | O | CH₃ | OCH₃ | N | |
| —C(OCH₂CH₂CH₃)₃ | H | H | O | OCH₃ | OCH₃ | N | |
| —C(C₂H₅)(OCH₃)₂ | H | H | O | OCH₃ | OCH₃ | CH | |
| —C(C₂H₅)(OCH₃)₂ | H | H | O | CH₃ | OCH₃ | CH | |
| —C(C₂H₅)(OCH₃)₂ | H | H | O | CH₃ | CH₃ | CH | |
| —C(C₂H₅)(OCH₃)₂ | H | H | O | CH₃ | OCH₃ | N | |
| —C(C₂H₅)(OCH₃)₂ | H | H | O | OCH₃ | OCH₃ | N | |
| —C(n-C₃H₇)(OCH₃)₂ | H | H | O | OCH₃ | OCH₃ | CH | |
| 2-ethyl-1,3-dioxolan-2-yl | H | H | O | OCH₃ | OCH₃ | CH | |
| 2-ethyl-1,3-dioxolan-2-yl | H | H | O | CH₃ | OCH₃ | CH | |
| 2-ethyl-1,3-dioxolan-2-yl | H | H | O | CH₃ | OCH₃ | N | |
| 2-propyl-1,3-dioxolan-2-yl | H | H | O | OCH₃ | OCH₃ | CH | |
| 2-propyl-1,3-dioxolan-2-yl | H | H | O | CH₃ | OCH₃ | CH | |
| 2-propyl-1,3-dioxolan-2-yl | H | H | O | CH₃ | OCH₃ | N | |
| 1,3-dioxolan-2-yl | C₂H₅ | H | O | OCH₃ | OCH₃ | CH | |
| 1,3-dioxolan-2-yl | Cl | H | O | OCH₃ | OCH₃ | CH | |

TABLE Ib

GENERAL STRUCTURE Ib

| R₁ | R₁₂ | R | W | X | Y | Z | m.p. ° C. |
|---|---|---|---|---|---|---|---|
| 1,3-dioxolan-2-yl | H | H | O | CH₃ | CH₃ | CH | |
| 1,3-dioxolan-2-yl | H | H | O | CH₃ | OCH₃ | CH | |
| 1,3-dioxolan-2-yl | H | H | O | OCH₃ | OCH₃ | CH | |
| 1,3-dioxolan-2-yl | H | H | O | CH₃ | CH₃ | N | |
| 1,3-dioxolan-2-yl | H | H | O | CH₃ | OCH₃ | N | |
| 1,3-dioxolan-2-yl | H | H | O | OCH₃ | OCH₃ | N | |
| 1,3-dioxolan-2-yl | H | H | O | Cl | OCH₃ | CH | |
| 1,3-dioxolan-2-yl | H | H | O | OCH₂CH₃ | NHCH₃ | N | |
| 1,3-dioxolan-2-yl | H | H | O | OCF₂H | CH₃ | CH | |
| 1,3-dioxolan-2-yl | H | H | O | CF₂H | OCH₃ | CH | |
| 1,3-dioxolan-2-yl | H | H | O | CF₂H | OCH₃ | N | |
| 1,3-dioxolan-2-yl | H | H | O | OCH₂CH₂F | CH₃ | N | |
| 1,3-dioxolan-2-yl | H | H | O | OCH₂CHF₂ | CH₃ | N | |
| 1,3-dioxolan-2-yl | H | H | O | OCH₂CF₃ | CH₃ | N | |
| 1,3-dioxolan-2-yl | H | H | O | CF₃ | CH₃ | CH | |
| 1,3-dioxolan-2-yl | H | H | O | CF₃ | OCH₃ | N | |
| 1,3-dioxolan-2-yl | H | H | O | CH₃ | NHCH₃ | N | |
| 1,3-dioxolan-2-yl | H | H | O | OCH₃ | N(CH₃)₂ | N | |
| 1,3-dioxolan-2-yl | H | H | O | OCH₃ | N(CH₃)OCH₃ | N | |
| 1,3-dioxolan-2-yl | H | H | O | OCH₃ | CH₂OCH₃ | N | |
| 1,3-dioxolan-2-yl | H | H | O | CH₃ | CH₂OCH₃ | CH | |
| 1,3-dioxolan-2-yl | H | H | O | CH₃ | SCH₃ | N | |
| 1,3-dioxolan-2-yl | H | H | O | CH₃ | OCH₂CH=CH₂ | N | |
| 1,3-dioxolan-2-yl | H | H | O | CH₃ | OCH₂C≡CH | N | |
| 1,3-dioxolan-2-yl | H | H | O | CH₃ | CH₂OCH₂CH₃ | N | |
| 1,3-dioxolan-2-yl | H | H | O | CH₃ | CH₂OC₂H₅ | N | |
| 1,3-dioxolan-2-yl | H | H | O | CH₃ | OCH₂CH₂OCH₃ | CH | |
| 1,3-dioxolan-2-yl | H | H | O | CH₃ | OCH₂CH₂OCH₃ | N | |
| 1,3-dioxolan-2-yl | H | H | O | CH₃ | CH₂SCH₃ | N | |
| 1,3-dioxolan-2-yl | H | H | O | CH₃ | CH₂SCH₃ | CH | |
| 1,3-dioxolan-2-yl | H | H | O | CH₃ | CH(OCH₃)₂ | CH | |
| 1,3-dioxolan-2-yl | H | H | O | CH₃ | i-C₃H₇ | CH | |
| 1,3-dioxolan-2-yl | H | H | O | CH₃ | CH(OCH₃)₂ | N | |
| 1,3-dioxolan-2-yl | H | H | O | OCH₃ | 1,3-dioxolan-2-yl | CH | |
| 1,3-dioxolan-2-yl | H | H | O | OCH₃ | 1,3-dioxolan-2-yl | N | |
| 1,3-dioxolan-2-yl | H | H | O | OCH₃ | 4-methyl-1,3-dioxolan-2-yl | N | |
| 1,3-dioxolan-2-yl | H | H | O | OCH₃ | 4-methyl-1,3-dioxolan-2-yl | CH | |
| 1,3-dioxolan-2-yl | H | H | O | OCH₃ | 4-ethyl-1,3-dioxolan-2-yl | CH | |
| 1,3-dioxolan-2-yl | H | H | O | OCH₃ | 1,3-dioxol-2-yl | N | |
| 1,3-dioxolan-2-yl | H | H | O | OCH₃ | 1,3-dioxol-2-yl | CH | |
| 1,3-dioxolan-2-yl | H | H | O | OCH₃ | cyclopropyl | CH | |

TABLE Ib-continued

GENERAL STRUCTURE Ib

| R₁ | R₁₂ | R | W | X | Y | Z | m.p. °C. |
|---|---|---|---|---|---|---|---|
| 1,3-dioxolan-2-yl | H | H | O | OCF₂H | OCF₂H | CH | |
| 1,3-dioxolan-2-yl | H | H | O | Br | OCF₂H | CH | |
| 1,3-dioxolan-2-yl | H | H | O | OCH₃ | cyclopropyl | N | |
| 1,3-dioxolan-2-yl | H | H | O | F | CH₃ | CH | |
| 1,3-dioxolan-2-yl | H | H | O | F | OCH₃ | CH | |
| 1,3-dioxolan-2-yl | H | H | O | Br | OCH₃ | CH | |
| 1,3-dioxolan-2-yl | H | H | O | Br | CH₃ | CH | |
| 1,3-dioxolan-2-yl | H | H | O | I | OCH₃ | CH | |
| 1,3-dioxolan-2-yl | H | H | O | OCH₃ | cyclopropyl | CH | |
| 1,3-dioxolan-2-yl | H | H | O | OCH₂CH₃ | cyclopropyl | N | |
| 1,3-dioxolan-2-yl | H | H | O | OCH₂CH₂F | cyclopropyl | N | |
| 1,3-dioxolan-2-yl | H | H | O | OCH₃ | cyclopropyl | N | |
| 1,3-dioxolan-2-yl | H | H | O | OCH₃ | CH(SCH₃)₂ | N | |
| 1,3-dioxolan-2-yl | H | H | O | OCH₃ | CH(SCH₃)₂ | CH | |
| 1,3-dioxolan-2-yl | H | H | O | OCH₃ | 1,3-dithiolan-2-yl | CH | |
| 1,3-dioxolan-2-yl | H | H | O | OCH₃ | 1,3-dithiolan-2-yl | N | |
| 1,3-dioxolan-2-yl | H | H | O | OCH₃ | 1,3-oxathiolan-2-yl | N | |
| 1,3-dioxolan-2-yl | H | CH₃ | O | OCH₃ | CH₃ | CH | |
| 1,3-dioxolan-2-yl | H | CH₃ | O | OCH₃ | OCH₃ | CH | |
| 1,3-dioxolan-2-yl | H | CH₃ | O | CH₃ | CH₃ | CH | |
| 1,3-dioxolan-2-yl | H | CH₃ | O | CH₃ | CH₃ | N | |
| 1,3-dioxolan-2-yl | H | CH₃ | O | CH₃ | OCH₃ | N | |
| 1,3-dioxolan-2-yl | H | CH₃ | O | OCH₃ | OCH₃ | N | |
| 1,3-dioxolan-2-yl | H | CH₃ | O | Cl | OCH₃ | N | |
| 1,3-dioxolan-2-yl | H | H | S | CH₃ | OCH₃ | CH | |
| 1,3-dioxolan-2-yl | H | H | S | CH₃ | CH₃ | CH | |
| 1,3-dioxolan-2-yl | H | H | S | OCH₃ | CH₃ | N | |
| 1,3-dioxolan-2-yl | H | H | S | OCH₃ | OCH₃ | N | |
| 1,3-dithiolan-2-yl | H | H | O | OCH₃ | CH₃ | CH | |
| 1,3-dithiolan-2-yl | H | H | O | CH₃ | CH₃ | CH | |
| 1,3-dithiolan-2-yl | H | H | O | Cl | OCH₃ | CH | |
| 1,3-dithiolan-2-yl | H | H | O | OCH₃ | OCH₃ | CH | |
| 1,3-dithiolan-2-yl | H | H | O | OCH₃ | OCH₃ | N | |
| 1,3-dithiolan-2-yl | H | H | O | OCH₃ | CH₃ | N | |
| 1,3-dithiolan-2-yl | H | H | O | OCH₂CF₃ | NHCH₃ | N | |
| 1,3-dithiolan-2-yl | H | H | O | OCH₂CH₂F | NHCH₃ | N | |
| —CH(OCH₃)₂ | H | H | O | CH₃ | CH₃ | CH | |
| —CH(OCH₃)₂ | H | H | O | CH₃ | CH₃ | N | |
| —CH(OCH₃)₂ | H | H | O | CH₃ | OCH₃ | N | |
| —CH(OCH₃)₂ | H | H | O | CH₃ | OCH₃ | CH | |
| —CH(OCH₃)₂ | H | H | O | OCH₃ | OCH₃ | CH | |
| —CH(OCH₃)₂ | H | H | O | OCH₃ | OCH₃ | N | |
| —CH(OCH₃)₂ | H | H | O | Cl | OCH₃ | CH | |
| —C(CH₃)(OCH₃)₂ | H | H | O | CH₃ | CH₃ | CH | |
| —C(CH₃)(OCH₃)₂ | H | H | O | CH₃ | CH₃ | N | |
| —C(CH₃)(OCH₃)₂ | H | H | O | CH₃ | OCH₃ | N | |
| —C(CH₃)(OCH₃)₂ | H | H | O | CH₃ | OCH₃ | CH | |
| —C(CH₃)(OCH₃)₂ | H | H | O | OCH₃ | OCH₃ | CH | |
| —C(CH₃)(OCH₃)₂ | H | H | O | OCH₃ | OCH₃ | N | |
| —C(CH₃)(OCH₃)₂ | H | H | O | Cl | OCH₃ | CH | |
| —CH(OC₂H₅)₂ | H | H | O | CH₃ | CH₃ | CH | |
| —CH(OC₂H₅)₂ | H | H | O | CH₃ | CH₃ | N | |
| —CH(OC₂H₅)₂ | H | H | O | CH₃ | OCH₃ | N | |
| —CH(OC₂H₅)₂ | H | H | O | CH₃ | OCH₃ | CH | |
| —CH(OC₂H₅)₂ | H | H | O | OCH₃ | OCH₃ | CH | |
| —CH(OC₂H₅)₂ | H | H | O | OCH₃ | OCH₃ | N | |
| —CH(SCH₃)₂ | H | H | O | CH₃ | CH₃ | CH | |
| —CH(SCH₃)₂ | H | H | O | CH₃ | CH₃ | N | |
| —CH(SCH₃)₂ | H | H | O | CH₃ | OCH₃ | N | |
| —CH(SCH₃)₂ | H | H | O | OCH₃ | OCH₃ | CH | |
| —CH(SCH₃)₂ | H | H | O | OCH₃ | OCH₃ | N | |
| 2-methyl-1,3-dioxolan-2-yl | H | H | O | CH₃ | CH₃ | CH | |
| 2-methyl-1,3-dioxolan-2-yl | H | H | O | CH₃ | CH₃ | N | |
| 2-methyl-1,3-dioxolan-2-yl | H | H | O | CH₃ | OCH₃ | N | |
| 2-methyl-1,3-dioxolan-2-yl | H | H | O | CH₃ | OCH₃ | CH | |
| 2-methyl-1,3-dioxolan-2-yl | H | H | O | OCH₃ | OCH₃ | CH | |
| 2-methyl-1,3-dioxolan-2-yl | H | H | O | OCH₃ | OCH₃ | N | |
| 2-methyl-1,3-dioxolan-2-yl | H | H | O | Cl | OCH₃ | CH | |
| 2-methyl-1,3-dioxolan-2-yl | H | H | O | Br | OCH₃ | CH | |
| 4-methyl-1,3-dioxolan-2-yl | H | H | O | OC₂H₅ | NHCH₃ | N | |
| 4-methyl-1,3- | H | H | O | CH₃ | CH₃ | CH | |

TABLE Ib-continued

GENERAL STRUCTURE Ib

| R₁ | R₁₂ | R | W | X | Y | Z | m.p. °C. |
|---|---|---|---|---|---|---|---|
| dioxolan-2-yl | | | | | | | |
| 4-methyl-1,3-dioxolan-2-yl | H | H | O | CH₃ | CH₃ | N | |
| 4-methyl-1,3-dioxolan-2-yl | H | H | O | CH₃ | OCH₃ | N | |
| 4-methyl-1,3-dioxolan-2-yl | H | H | O | CH₃ | OCH₃ | CH | |
| 4-methyl-1,3-dioxolan-2-yl | H | H | O | OCH₃ | OCH₃ | CH | |
| 4-methyl-1,3-dioxolan-2-yl | H | H | O | OCH₃ | OCH₃ | N | |
| 4-methyl-1,3-dioxolan-2-yl | H | H | O | Cl | OCH₃ | CH | |
| 4-methyl-1,3-dioxolan-2-yl | H | H | O | Br | OCH₃ | CH | |
| 1,3-oxathiolan-2-yl | H | H | O | OC₂H₅ | NHCH₃ | N | |
| 1,3-oxathiolan-2-yl | H | H | O | CH₃ | CH₃ | CH | |
| 1,3-oxathiolan-2-yl | H | H | O | CH₃ | CH₃ | N | |
| 1,3-oxathiolan-2-yl | H | H | O | CH₃ | OCH₃ | N | |
| 1,3-oxathiolan-2-yl | H | H | O | CH₃ | OCH₃ | CH | |
| 1,3-oxathiolan-2-yl | H | H | O | OCH₃ | OCH₃ | CH | |
| 1,3-oxathiolan-2-yl | H | H | O | OCH₃ | OCH₃ | N | |
| 1,3-oxathiolan-2-yl | H | H | O | Cl | OCH₃ | CH | |
| 1,3-oxathiolan-2-yl | H | H | O | OC₂H₅ | NHCH₃ | N | |
| 2-methyl-1,3-dithiolan-2-yl | H | H | O | CH₃ | CH₃ | CH | |
| 2-methyl-1,3-dithiolan-2-yl | H 3 | H | O | CH₃ | CH₃ | N | |
| 2-methyl-1,3-dithiolan-2-yl | H | H | O | CH₃ | OCH₃ | N | |
| 2-methyl-1,3-dithiolan-2-yl | H | H | O | CH₃ | OCH₃ | CH | |
| 2-methyl-1,3-dithiolan-2-yl | H | H | O | OCH₃ | OCH₃ | CH | |
| hexahydro-1,3-dimethyl-pyrimidin-2-yl | H | H | O | OCH₃ | OCH₃ | N | |
| hexahydro-1,3-dimethyl-pyrimidin-2-yl | H | H | O | CH₃ | CH₃ | CH | |
| hexahydro-1,3-dimethyl-pyrimidin-2-yl | H | H | O | CH₃ | CH₃ | N | |
| hexahydro-1,3-dimethyl-pyrimidin-2-yl | H | H | O | CH₃ | OCH₃ | N | |
| hexahydro-1,3-dimethyl-pyrimidin-2-yl | H | H | O | CH₃ | OCH₃ | CH | |
| hexahydro-1,3-dimethyl-pyrimidin-2-yl | H | H | O | OCH₃ | OCH₃ | CH | |
| hexahydro-1,3-dimethyl-pyrimidin-2-yl | H | H | O | OCH₃ | OCH₃ | N | |
| 4,5-dimethyl-1,3-dioxolan-2-yl | H | H | O | CH₃ | CH₃ | CH | |
| 4,5-dimethyl-1,3-dixolan-2-yl | H | H | O | CH₃ | CH₃ | N | |
| 4,5-dimethyl-1,3-dioxolan-2-yl | H | H | O | CH₃ | OCH₃ | N | |
| 4,5-dimethyl-1,3-dioxolan-2-yl | H | H | O | CH₃ | OCH₃ | CH | |
| 4,5-dimethyl-1,3-dioxolan-2-yl | H | H | O | OCH₃ | OCH₃ | CH | |
| 4-ethyl-1,3-dioxolan-2-yl | H | H | O | CH₃ | CH₃ | CH | |
| 4-ethyl-1,3-dioxolan-2-yl | H | H | O | CH₃ | CH₃ | N | |
| 4-ethyl-1,3-dioxolan-2-yl | H | H | O | CH₃ | OCH₃ | N | |
| 4-ethyl-1,3-dioxolan-2-yl | H | H | O | CH₃ | OCH₃ | CH | |
| 4-ethyl-1,3-dioxolan-2-yl | H | H | O | OCH₃ | OCH₃ | CH | |
| 1,3-dimethyl-2-imidazolinyl | H | H | O | OCH₃ | OCH₃ | N | |
| 1,3-dimethyl-2-imidazolinyl | H | H | O | CH₃ | CH₃ | CH | |
| 1,3-dimethyl-2-imidazolinyl | H | H | O | CH₃ | CH₃ | N | |
| 1,3-dimethyl-2-imidazolinyl | H | H | O | CH₃ | OCH₃ | N | |
| 1,3-dimethyl-2-imidazolinyl | H | H | O | CH₃ | OCH₃ | CH | |
| 1,3-dimethyl-2-imidazolinyl | H | H | O | OCH₃ | OCH₃ | CH | |

TABLE Ib-continued

GENERAL STRUCTURE Ib

| R₁ | R₁₂ | R | W | X | Y | Z | m.p. °C. |
|---|---|---|---|---|---|---|---|
| 1,3-dioxolan-2-yl | CH₃ | H | O | CH₃ | CH₃ | CH | |
| 1,3-dioxolan-2-yl | CH₃ | H | O | OCH₃ | CH₃ | CH | |
| 1,3-dioxolan-2-yl | CH₃ | H | O | OCH₃ | OCH₃ | CH | |
| 1,3-dioxolan-2-yl | CH₃ | H | O | OCH₃ | OCH₃ | N | |
| 1,3-dioxolan-2-yl | CH₃ | H | O | OCH₃ | CH₃ | N | |
| 1,3-dioxolan-2-yl | CH₃ | H | O | CH₃ | CH₃ | N | |
| —C(OCH₃)₃ | H | H | O | OCH₃ | OCH₃ | CH | |
| —C(OCH₃)₃ | H | H | O | CH₃ | OCH₃ | CH | |
| —C(OCH₃)₃ | H | H | O | CH₃ | CH₃ | CH | |
| —C(OCH₃)₃ | H | H | O | Cl | OCH₃ | CH | |
| —C(OCH₃)₃ | H | H | O | Br | OCH₃ | CH | |
| —C(OCH₃)₃ | H | H | O | CH₃ | H | CH | |
| —C(OCH₃)₃ | H | H | O | OCH₃ | H | CH | |
| —C(OCH₃)₃ | H | H | O | OCH₃ | CH₂OC₂H₅ | CH | |
| —C(OCH₃)₃ | H | H | O | OCF₂H | OCH₃ | CH | |
| —C(OCH₃)₃ | H | H | O | OCH₃ | CH(OCH₃)₂ | CH | |
| —C(OCH₃)₃ | H | H | O | CH₃ | OC₂H₅ | CH | |
| —C(OCH₃)₃ | H | H | O | CH₃ | CH₂OCH₃ | CH | |
| —C(OCH₃)₃ | H | H | O | OCH₃ | CH₂OCH₃ | CH | |
| —C(OCH₃)₃ | H | H | O | OCH₃ | C₂H₅ | CH | |
| —C(OCH₃)₃ | H | H | O | Cl | OC₂H₅ | CH | |
| —C(OCH₃)₃ | H | H | O | OCH₂CH₃ | NHCH₃ | N | |
| —C(OCH₃)₃ | H | H | O | OCF₂H | CH₃ | CH | |
| —C(OCH₃)₃ | H | H | O | CF₂H | OCH₃ | CH | |
| —C(OCH₃)₃ | H | H | O | CF₂H | OCH₃ | N | |
| —C(OCH₃)₃ | H | H | O | OCH₃ | cyclopropyl | N | |
| —C(OCH₃)₃ | H | H | O | OCF₂H | OCF₂H | CH | |
| —C(OCH₃)₃ | H | H | O | CH₃ | OCH₃ | N | |
| —C(OCH₃)₃ | H | H | O | OCH₃ | OCH₃ | N | |
| —C(OCH₃)₃ | H | H | O | CH₃ | CH₃ | N | |
| —C(OC₂H₅)₃ | H | H | O | OCH₃ | OCH₃ | CH | |
| —C(OC₂H₅)₃ | H | H | O | CH₃ | OCH₃ | CH | |
| —C(OC₂H₅)₃ | H | H | O | CH₃ | CH₃ | CH | |
| —C(OC₂H₅)₃ | H | H | O | Cl | OCH₃ | CH | |
| —C(OC₂H₅)₃ | H | H | O | Br | OCH₃ | CH | |
| —C(OC₂H₅)₃ | H | H | O | CH₃ | H | CH | |
| —C(OC₂H₅)₃ | H | H | O | OCH₃ | H | CH | |
| —C(OC₂H₅)₃ | H | H | O | OCH₃ | CH₂OC₂H₅ | CH | |
| —C(OC₂H₅)₃ | H | H | O | OCF₂H | OCH₃ | CH | |
| —C(OC₂H₅)₃ | H | H | O | OCH₃ | CH(OCH₃)₂ | CH | |
| —C(OC₂H₅)₃ | H | H | O | CH₃ | OC₂H₅ | CH | |
| —C(OC₂H₅)₃ | H | H | O | CH₃ | CH₂OCH₃ | CH | |
| —C(OC₂H₅)₃ | H | H | O | OCH₃ | CH₂OCH₃ | CH | |
| —C(OC₂H₅)₃ | H | H | O | OCH₃ | C₂H₅ | CH | |
| —C(OC₂H₅)₃ | H | H | O | Cl | OC₂H₅ | CH | |
| —C(OC₂H₅)₃ | H | H | O | OCH₂CH₃ | NHCH₃ | N | |
| —C(OC₂H₅)₃ | H | H | O | OCF₂H | CH₃ | CH | |
| —C(OC₂H₅)₃ | H | H | O | CF₂H | OCH₃ | CH | |
| —C(OC₂H₅)₃ | H | H | O | CF₂H | OCH₃ | N | |
| —C(OC₂H₅)₃ | H | H | O | OCH₃ | cyclopropyl | N | |
| —C(OC₂H₅)₃ | H | H | O | OCF₂H | OCF₂H | CH | |
| —C(OC₂H₅)₃ | H | H | O | CH₃ | OCH₃ | N | |
| —C(OC₂H₅)₃ | H | H | O | OCH₃ | OCH₃ | N | |
| —C(OC₂H₅)₃ | H | H | O | CH₃ | CH₃ | N | |
| —C(OCH₂CH₂CH₃)₃ | H | H | O | OCH₃ | OCH₃ | CH | |
| —C(OCH₂CH₂CH₃)₃ | H | H | O | CH₃ | OCH₃ | CH | |
| —C(OCH₂CH₂CH₃)₃ | H | H | O | CH₃ | CH₃ | CH | |
| —C(OCH₂CH₂CH₃)₃ | H | H | O | Cl | OCH₃ | CH | |
| —C(OCH₂CH₂CH₃)₃ | H | H | O | CH₃ | OCH₃ | N | |
| —C(OCH₂CH₂CH₃)₃ | H | H | O | OCH₃ | OCH₃ | N | |
| —C(C₂H₅)(OCH₃)₂ | H | H | O | OCH₃ | OCH₃ | CH | |
| —C(C₂H₅)(OCH₃)₂ | H | H | O | CH₃ | OCH₃ | CH | |
| —C(C₂H₅)(OCH₃)₂ | H | H | O | CH₃ | CH₃ | CH | |
| —C(C₂H₅)(OCH₃)₂ | H | H | O | CH₃ | OCH₃ | N | |
| —C(C₂H₅)(OCH₃)₂ | H | H | O | OCH₃ | OCH₃ | N | |
| —C(n-C₃H₇)(OCH₃)₂ | H | H | O | OCH₃ | OCH₃ | CH | |
| 2-ethyl-1,3-dioxolan-2-yl | H | H | O | OCH₃ | OCH₃ | CH | |
| 2-ethyl-1,3-dioxolan-2-yl | H | H | O | CH₃ | OCH₃ | CH | |
| 2-ethyl-1,3-dioxolan-2-yl | H | H | O | CH₃ | OCH₃ | N | |
| 2-propyl-1,3-dioxolan-2-yl | H | H | O | OCH₃ | OCH₃ | CH | |
| 2-propyl-1,3-dioxolan-2-yl | H | H | O | CH₃ | OCH₃ | CH | |
| 2-propyl-1,3- | H | H | O | CH₃ | OCH₃ | N | |

TABLE Ib-continued

GENERAL STRUCTURE Ib

| R₁ | R₁₂ | R | W | X | Y | Z | m.p. °C. |
|---|---|---|---|---|---|---|---|
| dioxolan-2-yl | | | | | | | |

TABLE Ic

GENERAL STRUCTURE Ic

| R₁ | R₁₂ | R | W | X | Y | Z | m.p. °C. |
|---|---|---|---|---|---|---|---|
| 1,3-dioxolan-2-yl | H | H | O | CH₃ | CH₃ | CH | |
| 1,3-dioxolan-2-yl | H | H | O | OCH₃ | CH₃ | CH | |
| 1,3-dioxolan-2-yl | H | H | O | OCH₃ | OCH₃ | CH | |
| 1,3-dioxolan-2-yl | H | H | O | Cl | OCH₃ | CH | |
| 1,3-dioxolan-2-yl | H | H | O | OCH₃ | OCH₃ | N | |
| 1,3-dioxolan-2-yl | H | H | O | CH₃ | OCH₃ | N | |
| 1,3-dioxolan-2-yl | H | H | O | OCF₂H | OCH₃ | CH | |
| 1,3-dioxolan-2-yl | H | H | O | OCH₂CH₂F | NHCH₃ | N | |
| 1,3-dioxolan-2-yl | H | H | O | OCH₂CH₂F | OC₂H₅ | N | |
| 1,3-dioxolan-2-yl | H | H | O | OCH₂CHF₂ | OCH₃ | N | |
| 1,3-dioxolan-2-yl | H | H | O | OCH₂CF₃ | NHCH₃ | N | |
| 1,3-dioxolan-2-yl | H | H | O | OCH₂CF₃ | N(CH₃)₂ | N | |
| 1,3-dioxolan-2-yl | H | H | O | OCH₂CF₃ | OCH₃ | N | |
| 1,3-dioxolan-2-yl | H | H | O | CF₃ | OCH₃ | CH | |
| 1,3-dioxolan-2-yl | H | H | O | I | OCH₃ | CH | |
| 1,3-dioxolan-2-yl | H | H | O | Br | OCH₃ | CH | |
| 1,3-dioxolan-2-yl | H | H | O | F | OCH₃ | CH | |
| 1,3-dioxolan-2-yl | H | H | O | CH₃ | OC₂H₅ | N | |
| 1,3-dioxolan-2-yl | H | H | O | CH₃ | CH₂OCH₃ | CH | |
| 1,3-dioxolan-2-yl | H | H | O | CH₃ | CH₂SCH₃ | CH | |
| 1,3-dioxolan-2-yl | H | H | O | OCF₂H | OCF₂H | CH | |
| 1,3-dioxolan-2-yl | H | H | O | OCH₃ | NHCH₃ | CH | |
| 1,3-dioxolan-2-yl | H | H | O | OCH₃ | N(OCH₃)CH₃ | N | |
| 1,3-dioxolan-2-yl | H | H | O | OCH₃ | C₂H₅ | N | |
| 1,3-dioxolan-2-yl | H | H | O | CH₃ | OCH₂CH₂OCH₃ | CH | |
| 1,3-dioxolan-2-yl | H | H | O | OCH₃ | cyclopropyl | N | |
| 1,3-dioxolan-2-yl | H | H | O | OCH₃ | SCF₂H | CH | |
| 1,3-dioxolan-2-yl | H | H | O | OCH₃ | CH(OCH₃)₂ | CH | |
| 1,3-dioxolan-2-yl | H | H | O | OCH₃ | 1,3-dioxolan-2-yl | CH | |
| 1,3-dioxolan-2-yl | H | H | O | CH₃ | OCH₂C≡CH | N | |
| 1,3-dioxolan-2-yl | H | H | O | CH₃ | OCH₂CH=CH₂ | CH | |
| 1,3-dioxolan-2-yl | H | H | O | OCH₃ | CH₂OC₂H₅ | N | |
| 1,3-dioxolan-2-yl | 4-CH₃ | H | O | OCH₃ | CH₃ | N | |
| 1,3-dioxolan-2-yl | 4-C₂H₅ | H | O | OCH₃ | CH₃ | CH | |
| 1,3-dioxolan-2-yl | 4-Cl | H | O | OCH₃ | CH₃ | CH | |
| 1,3-dioxolan-2-yl | H | CH₃ | O | CH₃ | CH₃ | CH | |
| 1,3-dioxolan-2-yl | H | H | S | CH₃ | CH₃ | CH | |
| 1,3-dithiolan-2-yl | H | H | O | CH₃ | CH₃ | CH | |
| 1,3-dithiolan-2-yl | H | H | O | OCH₃ | CH₃ | CH | |
| 1,3-dithiolan-2-yl | H | H | O | OCH₃ | OCH₃ | CH | |
| 1,3-dithiolan-2-yl | H | H | O | Cl | OCH₃ | CH | |
| 1,3-dithiolan-2-yl | H | H | O | OCH₃ | OCH₃ | N | |
| 1,3-dithiolan-2-yl | H | H | O | OCH₃ | CH₃ | N | |
| CH(OCH₃)₂ | H | H | O | CH₃ | CH₃ | CH | |
| CH(OCH₃)₂ | H | H | O | OCH₃ | CH₃ | CH | |
| CH(OCH₃)₂ | H | H | O | OCH₃ | OCH₃ | CH | |
| CH(OCH₃)₂ | H | H | O | Cl | OCH₃ | CH | |
| CH(OCH₃)₂ | H | H | O | OCH₃ | OCH₃ | N | |
| CH(OCH₃)₂ | H | H | O | OCH₃ | CH₃ | N | |
| CH(OC₂H₅)₂ | H | H | O | CH₃ | CH₃ | CH | |
| CH(OC₂H₅)₂ | H | H | O | OCH₃ | CH₃ | CH | |
| CH(OC₂H₅)₂ | H | H | O | OCH₃ | OCH₃ | CH | |
| CH(OC₂H₅)₂ | H | H | O | Cl | OCH₃ | CH | |
| CH(OC₂H₅)₂ | H | H | O | OCH₃ | OCH₃ | N | |
| CH(OC₂H₅)₂ | H | H | O | OCH₃ | CH₃ | N | |
| CH(SCH₃)₂ | H | H | O | CH₃ | CH₃ | CH | |
| CH(SCH₃)₂ | H | H | O | OCH₃ | CH₃ | CH | |
| CH(SCH₃)₂ | H | H | O | OCH₃ | OCH₃ | CH | |
| CH(SCH₃)₂ | H | H | O | Cl | OCH₃ | CH | |
| CH(SCH₃)₂ | H | H | O | OCH₃ | OCH₃ | N | |
| CH(SCH₃)₂ | H | H | O | OCH₃ | CH₃ | N | |
| C(CH₃)(OCH₃)₂ | H | H | O | CH₃ | OCH₃ | CH | |
| C(CH₃)(OCH₃)₂ | H | H | O | CH₃ | OCH₃ | N | |
| C(CH₃)(SCH₃)₂ | H | H | O | CH₃ | OCH₃ | CH | |
| C(CH₃)(SCH₃)₂ | H | H | O | CH₃ | OCH₃ | N | |
| 2-methyl-1,3-dioxolan-2-yl | H | H | O | CH₃ | OCH₃ | CH | |
| 2-methyl-1,3-dioxolan-2-yl | H | H | O | CH₃ | OCH₃ | N | |
| 4-methyl-1,3-dioxolan-2-yl | H | H | O | CH₃ | OCH₃ | CH | |
| 4-methyl-1,3- | H | H | O | CH₃ | OCH₃ | N | |

TABLE Ic-continued

GENERAL STRUCTURE Ic

| R₁ | R₁₂ | R | W | X | Y | Z | m.p. °C. |
|---|---|---|---|---|---|---|---|
| dioxolan-2-yl | | | | | | | |
| 1,3-oxathiolan-2-yl | H | H | O | CH₃ | OCH₃ | CH | |
| 1,3-oxathiolan-2-yl | H | H | O | CH₃ | OCH₃ | N | |
| 2-methyl-1,3-dithiolan-2-yl | H | H | O | CH₃ | OCH₃ | CH | |
| 2-methyl-1,3-dithiolan-2-yl | H | H | O | CH₃ | OCH₃ | N | |
| hexahydro-1,3-dimethyl-pyrimidin-2-yl | H | H | O | CH₃ | OCH₃ | CH | |
| hexahydro-1,3-dimethyl-pyrimidin-2-yl | H | H | O | CH₃ | OCH₃ | N | |
| 4,5-dimethyl-1,3-dioxolan-2-yl | H | H | O | CH₃ | OCH₃ | CH | |
| 4,5-dimethyl-1,3-dioxolan-2-yl | H | H | O | CH₃ | OCH₃ | N | |
| 4-ethyl-1,3-dioxolan-2-yl | H | H | O | CH₃ | OCH₃ | CH | |
| 4-ethyl-1,3-dioxolan-2-yl | H | H | O | CH₃ | OCH₃ | N | |
| 1,3-dimethyl-2-imidazolidinyl | H | H | O | CH₃ | OCH₃ | CH | |
| 1,3-dimethyl-2-imidazolidinyl | H | H | O | CH₃ | OCH₃ | N | |
| —C(OCH₃)₃ | H | H | O | OCH₃ | OCH₃ | CH | |
| —C(OCH₃)₃ | H | H | O | CH₃ | OCH₃ | CH | |
| —C(OCH₃)₃ | H | H | O | CH₃ | CH₃ | CH | |
| —C(OCH₃)₃ | H | H | O | Cl | OCH₃ | CH | |
| —C(OCH₃)₃ | H | H | O | CH₃ | OCH₃ | N | |
| —C(OCH₃)₃ | H | H | O | OCH₃ | OCH₃ | N | |
| —C(OC₂H₅)₃ | H | H | O | OCH₃ | OCH₃ | CH | |
| —C(OC₂H₅)₃ | H | H | O | CH₃ | OCH₃ | CH | |
| —C(OC₂H₅)₃ | H | H | O | CH₃ | CH₃ | CH | |
| —C(OC₂H₅)₃ | H | H | O | Cl | OCH₃ | CH | |
| —C(OC₂H₅)₃ | H | H | O | CH₃ | OCH₃ | N | |
| —C(OC₂H₅)₃ | H | H | O | OCH₃ | OCH₃ | N | |
| —C(OCH₂CH₂CH₃)₃ | H | H | O | OCH₃ | OCH₃ | CH | |
| —C(OCH₂CH₂CH₃)₃ | H | H | O | CH₃ | OCH₃ | CH | |
| —C(OCH₂CH₂CH₃)₃ | H | H | O | CH₃ | CH₃ | CH | |
| —C(OCH₂CH₂CH₃)₃ | H | H | O | Cl | OCH₃ | CH | |
| —C(OCH₂CH₂CH₃)₃ | H | H | O | CH₃ | OCH₃ | N | |
| —C(OCH₂CH₂CH₃)₃ | H | H | O | OCH₃ | OCH₃ | N | |

TABLE Id

GENERAL STRUCTURE Id

| R₁ | R₁₂ | R | W | X | Y | Z | m.p. °C. |
|---|---|---|---|---|---|---|---|
| 1,3-dioxolan-2-yl | H | H | O | CH₃ | CH₃ | CH | |
| 1,3-dioxolan-2-yl | H | H | O | OCH₃ | CH₃ | CH | |
| 1,3-dioxolan-2-yl | H | H | O | OCH₃ | OCH₃ | CH | |
| 1,3-dioxolan-2-yl | H | H | O | Cl | OCH₃ | CH | |
| 1,3-dioxolan-2-yl | H | H | O | OCH₃ | OCH₃ | N | |
| 1,3-dioxolan-2-yl | H | H | O | CH₃ | OCH₃ | N | |
| 1,3-dioxolan-2-yl | H | H | O | OCF₂H | OCH₃ | CH | |
| 1,3-dioxolan-2-yl | H | H | O | OCH₂CH₂F | NHCH₃ | N | |
| 1,3-dioxolan-2-yl | H | H | O | OCH₂CH₂F | OC₂H₅ | N | |
| 1,3-dioxolan-2-yl | H | H | O | OCH₂CHF₂ | OCH₃ | N | |
| 1,3-dioxolan-2-yl | H | H | O | OCH₂CF₃ | NHCH₃ | N | |
| 1,3-dioxolan-2-yl | H | H | O | OCH₂CF₃ | N(CH₃)₂ | N | |
| 1,3-dioxolan-2-yl | H | H | O | OCH₂CF₃ | OCH₃ | N | |
| 1,3-dioxolan-2-yl | H | H | O | CF₃ | OCH₃ | CH | |
| 1,3-dioxolan-2-yl | H | H | O | I | OCH₃ | CH | |
| 1,3-dioxolan-2-yl | H | H | O | Br | OCH₃ | CH | |
| 1,3-dioxolan-2-yl | H | H | O | F | OCH₃ | CH | |
| 1,3-dioxolan-2-yl | H | H | O | CH₃ | OC₂H₅ | N | |
| 1,3-dioxolan-2-yl | H | H | O | CH₃ | CH₂OCH₃ | CH | |
| 1,3-dioxolan-2-yl | H | H | O | CH₃ | CH₂SCH₃ | CH | |
| 1,3-dioxolan-2-yl | H | H | O | OCF₂H | OCF₂H | CH | |
| 1,3-dioxolan-2-yl | H | H | O | OCH₃ | NHCH₃ | CH | |
| 1,3-dioxolan-2-yl | H | H | O | OCH₃ | N(OCH₃)CH₃ | N | |
| 1,3-dioxolan-2-yl | H | H | O | OCH₃ | C₂H₅ | N | |
| 1,3-dioxolan-2-yl | H | H | O | CH₃ | OCH₂CH₂OCH₃ | CH | |
| 1,3-dioxolan-2-yl | H | H | O | OCH₃ | cyclopropyl | N | |
| 1,3-dioxolan-2-yl | H | H | O | OCH₃ | SCF₂H | CH | |
| 1,3-dioxolan-2-yl | H | H | O | OCH₃ | CH(OCH₃)₂ | CH | |
| 1,3-dioxolan-2-yl | H | H | O | OCH₃ | 1,3-dioxolan-2-yl | CH | |
| 1,3-dioxolan-2-yl | H | H | O | CH₃ | OCH₂C≡CH | CH | |
| 1,3-dioxolan-2-yl | H | H | O | CH₃ | OCH₂CH=CH₂ | CH | |
| 1,3-dioxolan-2-yl | H | H | O | OCH₃ | CH₂OC₂H₅ | N | |

TABLE Id-continued

| | | | | GENERAL STRUCTURE Id | | | |
|---|---|---|---|---|---|---|---|
| $R_1$ | $R_{12}$ | R | W | X | Y | Z | m.p. °C. |
| 1,3-dioxolan-2-yl | $CH_3$ | H | O | $OCH_3$ | $CH_3$ | N | |
| 1,3-dioxolan-2-yl | $C_2H_5$ | H | O | $OCH_3$ | $CH_3$ | CH | |
| 1,3-dioxolan-2-yl | Cl | H | O | $OCH_3$ | $CH_3$ | CH | |
| 1,3-dioxolan-2-yl | H | $CH_3$ | O | $CH_3$ | $CH_3$ | CH | |
| 1,3-dioxolan-2-yl | H | H | S | $CH_3$ | $CH_3$ | CH | |
| 1,3-dithiolan-2-yl | H | H | O | $CH_3$ | $CH_3$ | CH | |
| 1,3-dithiolan-2-yl | H | H | O | $OCH_3$ | $CH_3$ | CH | |
| 1,3-dithiolan-2-yl | H | H | O | $OCH_3$ | $OCH_3$ | CH | |
| 1,3-dithiolan-2-yl | H | H | O | Cl | $OCH_3$ | CH | |
| 1,3-dithiolan-2-yl | H | H | O | $OCH_3$ | $OCH_3$ | N | |
| 1,3-dithiolan-2-yl | H | H | O | $OCH_3$ | $CH_3$ | N | |
| $CH(OCH_3)_2$ | H | H | O | $CH_3$ | $CH_3$ | CH | |
| $CH(OCH_3)_2$ | H | H | O | $OCH_3$ | $CH_3$ | CH | |
| $CH(OCH_3)_2$ | H | H | O | $OCH_3$ | $OCH_3$ | CH | |
| $CH(OCH_3)_2$ | H | H | O | Cl | $OCH_3$ | CH | |
| $CH(OCH_3)_2$ | H | H | O | $OCH_3$ | $OCH_3$ | N | |
| $CH(OCH_3)_2$ | H | H | O | $OCH_3$ | $CH_3$ | N | |
| $CH(OC_2H_5)_2$ | H | H | O | $CH_3$ | $CH_3$ | CH | |
| $CH(OC_2H_5)_2$ | H | H | O | $OCH_3$ | $CH_3$ | CH | |
| $CH(OC_2H_5)_2$ | H | H | O | $OCH_3$ | $OCH_3$ | CH | |
| $CH(OC_2H_5)_2$ | H | H | O | Cl | $OCH_3$ | CH | |
| $CH(OC_2H_5)_2$ | H | H | O | $OCH_3$ | $OCH_3$ | N | |
| $CH(OC_2H_5)_2$ | H | H | O | $OCH_3$ | $CH_3$ | N | |
| $CH(SCH_3)_2$ | H | H | O | $CH_3$ | $CH_3$ | CH | |
| $CH(SCH_3)_2$ | H | H | O | $OCH_3$ | $CH_3$ | CH | |
| $CH(SCH_3)_2$ | H | H | O | $OCH_3$ | $OCH_3$ | CH | |
| $CH(SCH_3)_2$ | H | H | O | Cl | $OCH_3$ | CH | |
| $CH(SCH_3)_2$ | H | H | O | $OCH_3$ | $OCH_3$ | N | |
| $CH(SCH_3)_2$ | H | H | O | $OCH_3$ | $CH_3$ | N | |
| $C(CH_3)(OCH_3)_2$ | H | H | O | $CH_3$ | $OCH_3$ | CH | |
| $C(CH_3)(OCH_3)_2$ | H | H | O | $CH_3$ | $i-C_3H_7$ | CH | |
| $C(CH_3)(OCH_3)_2$ | H | H | O | $CH_3$ | $OCH_3$ | N | |
| $C(CH_3)(SCH_3)_2$ | H | H | O | $CH_3$ | $OCH_3$ | CH | |
| $C(CH_3)(SCH_3)_2$ | H | H | O | $CH_3$ | $OCH_3$ | N | |
| 2-methyl-1,3-dioxolan-2-yl | H | H | O | $CH_3$ | $OCH_3$ | CH | |
| 2-methyl-1,3-dioxolan-2-yl | H | H | O | $CH_3$ | $OCH_3$ | N | |
| 4-methyl-1,3-dioxolan-2-yl | H | H | O | $CH_3$ | $OCH_3$ | CH | |
| 4-methyl-1,3-dioxolan-2-yl | H | H | O | $CH_3$ | $OCH_3$ | N | |
| 1,3-oxathiolan-2-yl | H | H | O | $CH_3$ | $OCH_3$ | CH | |
| 1,3-oxathiolan-2-yl | H | H | O | $CH_3$ | $OCH_3$ | N | |
| 2-methyl-1,3-dithiolan-2-yl | H | H | O | $CH_3$ | $OCH_3$ | CH | |
| 2-methyl-1,3-dithiolan-2-yl | H | H | O | $CH_3$ | $OCH_3$ | N | |
| hexahydro-1,3-dimethyl-pyrimidin-2-yl | H | H | O | $CH_3$ | $OCH_3$ | CH | |
| hexahydro-1,3-dimethyl-pyrimidin-2-yl | H | H | O | $CH_2$ | $OCH_3$ | N | |
| 4,5-dimethyl-1,3-dioxolan-2-yl | H | H | O | $CH_3$ | $OCH_3$ | CH | |
| 4,5-dimethyl-1,3-dioxolan-2-yl | H | H | O | $CH_3$ | $OCH_3$ | N | |
| 4-ethyl-1,3-dioxolan-2-yl | H | H | O | $CH_3$ | $OCH_3$ | CH | |
| 4-ethyl-1,3-dioxolan-2-yl | H | H | O | $CH_3$ | $OCH_3$ | N | |
| 1,3-dimethyl-2-imidazolidinyl | H | H | O | $CH_3$ | $OCH_3$ | CH | |
| 1,3-dimethyl-2-imidazolidinyl | H | H | O | $CH_3$ | $OCH_3$ | N | |
| —$C(OCH_3)_3$ | H | H | O | $OCH_3$ | $OCH_3$ | CH | |
| —$C(OCH_3)_3$ | H | H | O | $CH_3$ | $OCH_3$ | CH | |
| —$C(OCH_3)_3$ | H | H | O | $CH_3$ | $CH_3$ | CH | |
| —$C(OCH_3)_3$ | H | H | O | Cl | $OCH_3$ | CH | |
| —$C(OCH_3)_3$ | H | H | O | $CH_3$ | $OCH_3$ | N | |
| —$C(OCH_3)_3$ | H | H | O | $OCH_3$ | $OCH_3$ | N | |
| —$C(OC_2H_5)_3$ | H | H | O | $OCH_3$ | $OCH_3$ | CH | |
| —$C(OC_2H_5)_3$ | H | H | O | $CH_3$ | $OCH_3$ | CH | |
| —$C(OC_2H_5)_3$ | H | H | O | $CH_3$ | $CH_3$ | CH | |
| —$C(OC_2H_5)_3$ | H | H | O | Cl | $OCH_3$ | CH | |
| —$C(OC_2H_5)_3$ | H | H | O | $CH_3$ | $OCH_3$ | N | |
| —$C(OC_2H_5)_3$ | H | H | O | $OCH_3$ | $OCH_3$ | N | |
| —$C(OCH_2CH_2CH_3)_3$ | H | H | O | $OCH_3$ | $OCH_3$ | CH | |
| —$C(OCH_2CH_2CH_3)_3$ | H | H | O | $CH_3$ | $OCH_3$ | CH | |
| —$C(OCH_2CH_2CH_3)_3$ | H | H | O | $CH_3$ | $CH_3$ | CH | |
| —$C(OCH_2CH_2CH_3)_3$ | H | H | O | Cl | $OCH_3$ | CH | |

TABLE Id-continued

GENERAL STRUCTURE Id

| $R_1$ | $R_{12}$ | R | W | X | Y | Z | m.p. °C. |
|---|---|---|---|---|---|---|---|
| —C(OCH$_2$CH$_2$CH$_3$)$_3$ | H | H | O | CH$_3$ | OCH$_3$ | N | |
| —C(OCH$_2$CH$_2$CH$_3$)$_3$ | H | H | O | OCH$_3$ | OCH$_3$ | N | |

TABLE Ie

GENERAL STRUCTURE Ie

| $R_1$ | $R_{12}$ | R | W | K | Y | Z | m.p. °C. |
|---|---|---|---|---|---|---|---|
| 1,3-dioxolan-2-yl | H | H | O | CH$_3$ | CH$_3$ | CH | |
| 1,3-dioxolan-2-yl | H | H | O | OCH$_3$ | CH$_3$ | CH | |
| 1,3-dioxolan-2-yl | H | H | O | OCH$_3$ | OCH$_3$ | CH | |
| 1,3-dioxolan-2-yl | H | H | O | Cl | OCH$_3$ | CH | |
| 1,3-dioxolan-2-yl | H | H | O | OCH$_3$ | OCH$_3$ | N | |
| 1,3-dioxolan-2-yl | H | H | O | CH$_3$ | OCH$_3$ | N | |
| 1,3-dioxolan-2-yl | H | H | O | OCF$_2$H | OCH$_3$ | CH | |
| 1,3-dioxolan-2-yl | H | H | O | OCH$_2$CH$_2$F | NHCH$_3$ | N | |
| 1,3-dioxolan-2-yl | H | H | O | OCH$_2$CH$_2$F | OC$_2$H$_5$ | N | |
| 1,3-dioxolan-2-yl | H | H | O | OCH$_2$CHF$_2$ | OCH$_3$ | N | |
| 1,3-dioxolan-2-yl | H | H | O | OCH$_2$CF$_3$ | NHCH$_3$ | N | |
| 1,3-dioxolan-2-yl | H | H | O | OCH$_2$CF$_3$ | N(CH$_3$)$_2$ | N | |
| 1,3-dioxolan-2-yl | H | H | O | OCH$_2$CF$_3$ | OCH$_3$ | N | |
| 1,3-dioxolan-2-yl | H | H | O | CF$_3$ | OCH$_3$ | CH | |
| 1,3-dioxolan-2-yl | H | H | O | I | OCH$_3$ | CH | |
| 1,3-dioxolan-2-yl | H | H | O | Br | OCH$_3$ | CH | |
| 1,3-dioxolan-2-yl | H | H | O | F | OCH$_3$ | CH | |
| 1,3-dioxolan-2-yl | H | H | O | CH$_3$ | OC$_2$H$_5$ | N | |
| 1,3-dioxolan-2-yl | H | H | O | CH$_3$ | CH$_2$OCH$_3$ | CH | |
| 1,3-dioxolan-2-yl | H | H | O | CH$_3$ | CH$_2$SCH$_3$ | CH | |
| 1,3-dioxolan-2-yl | H | H | O | OCF$_2$H | OCF$_2$H | CH | |
| 1,3-dioxolan-2-yl | H | H | O | OCH$_3$ | NHCH$_3$ | CH | |
| 1,3-dioxolan-2-yl | H | H | O | OCH$_3$ | N(OCH$_3$)CH$_3$ | N | |
| 1,3-dioxolan-2-yl | H | H | O | OCH$_3$ | C$_2$H$_5$ | N | |
| 1,3-dioxolan-2-yl | H | H | O | CH$_3$ | OCH$_2$CH$_2$OCH$_3$ | CH | |
| 1,3-dioxolan-2-yl | H | H | O | OCH$_3$ | cyclopropyl | N | |
| 1,3-dioxolan-2-yl | H | H | O | OCH$_3$ | SCF$_2$H | CH | |
| 1,3-dioxolan-2-yl | H | H | O | OCH$_3$ | CH(OCH$_3$)$_2$ | CH | |
| 1,3-dioxolan-2-yl | H | H | O | OCH$_3$ | 1,3-dioxolan-2-yl | CH | |
| 1,3-dioxolan-2-yl | H | H | O | CH$_3$ | OCH$_2$≡CH | N | |
| 1,3-dioxolan-2-yl | H | H | O | CH$_3$ | OCH$_2$CH=CH$_2$ | CH | |
| 1,3-dioxolan-2-yl | H | H | O | OCH$_3$ | CH$_2$OC$_2$H$_5$ | N | |
| 1,3-dioxolan-2-yl | CH$_3$ | H | O | OCH$_3$ | CH$_3$ | N | |
| 1,3-dioxolan-2-yl | C$_2$H$_5$ | H | O | OCH$_3$ | CH$_3$ | CH | |
| 1,3-dioxolan-2-yl | Cl | H | O | OCH$_3$ | CH$_3$ | CH | |
| 1,3-dioxolan-2-yl | H | CH$_3$ | O | CH$_3$ | CH$_3$ | CH | |
| 1,3-dioxolan-2-yl | H | H | S | CH$_3$ | CH$_3$ | CH | |
| 1,3-dithiolan-2-yl | H | H | O | CH$_3$ | CH$_3$ | CH | |
| 1,3-dithiolan-2-yl | H | H | O | OCH$_3$ | CH$_3$ | CH | |
| 1,3-dithiolan-2-yl | H | H | O | Cl | OCH$_3$ | CH | |
| 1,3-dithiolan-2-yl | H | H | O | OCH$_3$ | OCH$_3$ | N | |
| 1,3-dithiolan-2-yl | H | H | O | OCH$_3$ | CH$_3$ | N | |
| CH(OCH$_3$)$_2$ | H | H | O | CH$_3$ | CH$_3$ | CH | |
| CH(OCH$_3$)$_2$ | H | H | O | CH$_3$ OCH$_3$ | | CH | |
| CH(OCH$_3$)$_2$ | H | H | O | OCH$_3$ | OCH$_3$ | CH | |
| CH(OCH$_3$)$_2$ | H | H | O | Cl | OCH$_3$ | CH | |
| CH(OCH$_3$)$_2$ | H | H | O | OCH$_3$ | OCH$_3$ | N | |
| CH(OCH$_3$)$_2$ | H | H | O | OCH$_3$ | CH$_3$ | N | |
| CH(OC$_2$H$_5$)$_2$ | H | H | O | CH$_3$ | CH$_3$ | CH | |
| CH(OC$_2$H$_5$)$_2$ | H | H | O | OCH$_3$ | CH$_3$ | CH | |
| CH(OC$_2$H$_5$)$_2$ | H | H | O | OCH$_3$ | OCH$_3$ | CH | |
| CH(OC$_2$H$_5$)$_2$ | H | H | O | Cl | OCH$_3$ | CH | |
| CH(OC$_2$H$_5$)$_2$ | H | H | O | OCH$_3$ | OCH$_3$ | N | |
| CH(OC$_2$H$_5$)$_2$ | H | H | O | OCH$_3$ | CH$_3$ | N | |
| CH(SCH$_3$)$_2$ | H | H | O | CH$_3$ | CH$_3$ | CH | |
| CH(SCH$_3$)$_2$ | H | H | O | OCH$_3$ | CH$_3$ | CH | |
| CH(SCH$_3$)$_2$ | H | H | O | OCH$_3$ | OCH$_3$ | CH | |
| CH(SCH$_3$)$_2$ | H | H | O | Cl | OCH$_3$ | CH | |
| CH(SCH$_3$)$_2$ | H | H | O | OCH$_3$ | OCH$_3$ | N | |
| CH(SCH$_3$)$_2$ | H | H | O | OCH$_3$ | CH$_3$ | N | |
| C(CH$_3$)(OCH$_3$)$_2$ | H | H | O | CH$_3$ | OCH$_3$ | CH | |
| C(CH$_3$)(OCH$_3$)$_2$ | H | H | O | CH$_3$ | OCH$_3$ | N | |
| C(CH$_3$)(SCH$_3$)$_2$ | H | H | O | CH$_3$ | OCH$_3$ | CH | |
| C(CH$_3$)(SCH$_3$)$_2$ | H | H | O | CH$_3$ | OCH$_3$ | N | |
| 2-methyl-1,3-dioxolan-2-yl | H | H | O | CH$_3$ | OCH$_3$ | CH | |
| 2-methyl-1,3-dioxolan-2-yl | H | H | O | CH$_3$ | OCH$_3$ | N | |
| 4-methyl-1,3- | H | H | O | CH$_3$ | OCH$_3$ | CH | |

TABLE Ie-continued

| | | | GENERAL STRUCTURE Ie | | | | |
|---|---|---|---|---|---|---|---|
| R₁ | R₁₂ | R | W | K | Y | Z | m.p. °C. |
| dioxolan-2-yl | | | | | | | |
| 4-methyl-1,3-dioxolan-2-yl | H | H | O | CH₃ | OCH₃ | N | |
| 1,3-oxathiolan-2-yl | H | H | O | CH₃ | OCH₃ | CH | |
| 1,3-oxathiolan-2-yl | H | H | O | CH₃ | OCH₃ | N | |
| 2-methyl-1,3-dithiolan-2-yl | H | H | O | CH₃ | OCH₃ | CH | |
| 2-methyl-1,3-dithiolan-2-yl | H | H | O | CH₃ | OCH₃ | N | |
| hexahydro-1,3-dimethyl-pyrimidin-2-yl | H | H | O | CH₃ | OCH₃ | CH | |
| hexahydro-1,3-dimethyl-pyrimidin-2-yl | H | H | O | CH₃ | OCH₃ | N | |
| 4,5-dimethyl-1,3-dioxolan-2-yl | H | H | O | CH₃ | OCH₃ | CH | |
| 4,5-dimethyl-1,3-dioxolan-2-yl | H | H | O | CH₃ | OCH₃ | N | |
| 4-ethyl-1,3-dioxolan-2-yl | H | H | O | CH₃ | OCH₃ | CH | |
| 4-ethyl-1,3-dioxolan-2-yl | H | H | O | CH₃ | OCH₃ | N | |
| 1,3-dimethyl-2-imidazolidinyl | H | H | O | CH₃ | OCH₃ | CH | |
| 1,3-dimethyl-2-imidazolidinyl | H | H | O | CH₃ | OCH₃ | N | |
| —C(OCH₃)₃ | H | H | O | OCH₃ | OCH₃ | CH | |
| —C(OCH₃)₃ | H | H | O | CH₃ | OCH₃ | CH | |
| —C(OCH₃)₃ | H | H | O | CH₃ | CH₃ | CH | |
| —C(OCH₃)₃ | H | H | O | Cl | OCH₃ | CH | |
| —C(OCH₃)₃ | H | H | O | CH₃ | OCH₃ | N | |
| —C(OCH₃)₃ | H | H | O | OCH₃ | OCH₃ | N | |
| —C(OC₂H₅)₃ | H | H | O | OCH₃ | OCH₃ | CH | |
| —C(OC₂H₅)₃ | H | H | O | CH₃ | OCH₃ | CH | |
| —C(OC₂H₅)₃ | H | H | O | CH₃ | CH₃ | CH | |
| —C(OC₂H₇)₃ | H | H | O | Cl | OCH₃ | CH | |
| —C(OC₂H₅)₃ | H | H | O | CH₃ | OCH₃ | N | |
| —C(OC₂H₅)₃ | H | H | O | OCH₃ | OCH₃ | N | |
| —C(OCH₂CH₂CH₃)₂ | H | H | O | OCH₃ | OCH₃ | CH | |
| —C(OCH₂CH₂CH₃)₂ | H | H | O | CH₃ | OCH₃ | CH | |
| —C(OCH₂CH₂CH₃)₂ | H | H | O | CH₃ | CH₃ | CH | |
| —C(OCH₂CH₂CH₃)₂ | H | H | O | Cl | OCH₃ | CH | |
| —C(OCH₂CH₂CH₃)₂ | H | H | O | CH₃ | OCH₃ | N | |
| —C(OCH₂CH₂CH₃)₂ | H | H | O | OCH₃ | OCH₃ | N | |

TABLE II

| | | | General structure II | | | | |
|---|---|---|---|---|---|---|---|
| R₁ | R₁₁ | R | W | X | Y | Z | m.p. °C. |
| 1,3-dioxolan-2-yl | CH₃ | H | O | CH₃ | CH₃ | CH | |
| 1,3-dioxolan-2-yl | CH₃ | H | O | CH₃ | OCH₃ | CH | |
| 1,3-dioxolan-2-yl | CH₃ | H | O | OCH₃ | OCH₃ | CH | |
| 1,3-dioxolan-2-yl | CH₃ | H | O | Cl | OCH₃ | CH | |
| 1,3-dioxolan-2-yl | CH₃ | H | O | CH₃ | OCH₃ | N | |
| 1,3-dioxolan-2-yl | CH₃ | H | O | OCH₃ | OCH₃ | N | |
| 1,3-dioxolan-2-yl | CH₃ | H | O | OCH₂CH₂F | NHCH₃ | N | |
| 1,3-dioxolan-2-yl | CH₃ | H | O | OCH₂CF₃ | NHCH₃ | N | |
| 1,3-dioxolan-2-yl | CH₃ | H | O | OCH₃ | CH₂OCH₃ | CH | |
| 1,3-dioxolan-2-yl | CH₃ | H | O | OCH₃ | cyclopropyl | CH | |
| 1,3-dioxolan-2-yl | C₃H₇ | H | O | OCH₃ | CH₃ | CH | |
| 1,3-dioxolan-2-yl | CH₃ | H | S | CH₃ | CH₃ | CH | |
| 1,3-dioxolan-2-yl | CH₃ | CH₃ | O | CH₃ | CH₃ | CH | |
| CH(OCH₃)₂ | CH₃ | H | O | OCH₃ | CH₃ | CH | |
| CH(OCH₃)₂ | CH₃ | H | O | OCH₃ | CH₃ | N | |
| CH(OCH₃)₂ | CH₃ | H | O | CH₃ | CH₃ | CH | |
| CH(OCH₃)₂ | CH₃ | H | O | Cl | OCH₃ | CH | |
| 1,3-dithiolan-2-yl | CH₃ | H | O | OCH₃ | CH₃ | CH | |
| 1,3-dithiolan-2-yl | CH₃ | H | O | CH₃ | CH₃ | N | |
| 1,3-dithiolan-2-yl | CH₃ | H | O | CH₃ | CH₃ | CH | |
| 1,3-dithiolan-2-yl | CH₃ | H | O | Cl | OCH₃ | CH | |
| —C(OCH₃)₃ | CH₃ | H | O | OCH₃ | OCH₃ | CH | |
| —C(OCH₃)₃ | CH₃ | H | O | CH₃ | OCH₃ | CH | |
| —C(OCH₃)₃ | CH₃ | H | O | CH₃ | CH₃ | CH | |
| —C(OCH₃)₃ | CH₃ | H | O | Cl | OCH₃ | CH | |
| —C(OCH₃)₃ | CH₃ | H | O | CH₃ | OCH₃ | N | |
| —C(OCH₃)₃ | CH₃ | H | O | OCH₃ | OCH₃ | N | |
| —C(OC₂H₅)₃ | CH₃ | H | O | OCH₃ | OCH₃ | CH | |
| —C(OC₂H₅)₃ | CH₃ | H | O | CH₃ | OCH₃ | CH | |

TABLE II-continued

General structure II

| R₁ | R₁₁ | R | W | X | Y | Z | m.p. °C. |
|---|---|---|---|---|---|---|---|
| —C(OC₂H₅)₃ | CH₃ | H | O | CH₃ | CH₃ | CH | |
| —C(OC₂H₅)₃ | CH₃ | H | O | Cl | OCH₃ | CH | |
| —C(OC₂H₅)₃ | CH₃ | H | O | CH₃ | OCH₃ | N | |
| —C(OC₂H₅)₃ | CH₃ | H | O | OCH₃ | OCH₃ | N | |

TABLE IIa

General structure IIa

| R₁ | R₁₁ | R | W | X | Y | Z | m.p. °C. |
|---|---|---|---|---|---|---|---|
| 1,3-dioxolan-2-yl | CH₃ | H | O | CH₃ | CH₃ | CH | |
| 1,3-dioxolan-2-yl | CH₃ | H | O | CH₃ | OCH₃ | CH | |
| 1,3-dioxolan-2-yl | CH₃ | H | O | OCH₃ | OCH₃ | CH | |
| 1,3-dioxolan-2-yl | CH₃ | H | O | Cl | OCH₃ | CH | |
| 1,3-dioxolan-2-yl | CH₃ | H | O | CH₃ | OCH₃ | N | |
| 1,3-dioxolan-2-yl | CH₃ | H | O | OCH₃ | OCH₃ | N | |
| 1,3-dioxolan-2-yl | CH₃ | H | O | OCH₂CH₂F | NHCH₃ | N | |
| 1,3-dioxolan-2-yl | CH₃ | H | O | OCH₂CF₃ | NHCH₃ | N | |
| 1,3-dioxolan-2-yl | CH₃ | H | O | OCH₃ | CH₂OCH₃ | CH | |
| 1,3-dioxolan-2-yl | CH₃ | H | O | OCH₃ | cyclo-propyl | CH | |
| 1,3-dioxolan-2-yl | C₃H₇ | H | O | OCH₃ | CH₃ | CH | |
| 1,3-dioxolan-2-yl | CH₃ | H | S | CH₃ | CH₃ | CH | |
| 1,3-dioxolan-2-yl | CH₃ | CH₃ | O | CH₃ | CH₃ | CH | |
| CH(OCH₃)₂ | CH₃ | H | O | OCH₃ | CH₃ | CH | |
| CH(OCH₃)₂ | CH₃ | H | O | OCH₃ | CH₃ | N | |
| CH(OCH₃)₂ | CH₃ | H | O | CH₃ | CH₃ | CH | |
| CH(OCH₃)₂ | CH | H | O | Cl | OCH₃ | CH | |
| 1,3-dithiolan-2-yl | CH₃ | H | O | OCH₃ | CH₃ | CH | |
| 1,3-dithiolan-2-yl | CH₃ | H | O | OCH₃ | CH₃ | N | |
| 1,3-dithiolan-2-yl | CH₃ | H | O | CH₃ | CH₃ | CH | |
| 1,3-dithiolan-2-yl | CH₃ | H | O | Cl | OCH₃ | CH | |
| —C(OCH₃)₃ | CH₃ | H | O | OCH₃ | OCH₃ | CH | |
| —C(OCH₃)₃ | CH₃ | H | O | OCH₃ | CH₃ | CH | |
| —C(OCH₃)₃ | CH₃ | H | O | CH₃ | CH₃ | CH | |
| —C(OCH₃)₃ | CH₃ | H | O | Cl | OCH₃ | CH | |
| —C(OCH₃)₃ | CH₃ | H | O | CH₃ | OCH₃ | N | |
| —C(OCH₃)₃ | CH₃ | H | O | OCH₃ | OCH₃ | N | |
| —C(OCH₃)₃ | CH₃ | H | O | OCH₃ | OCH₃ | CH | |
| —C(OCH₃)₃ | CH₃ | H | O | CH₃ | OCH₃ | CH | |
| —C(OC₂H₅)₃ | CH₃ | H | O | CH₃ | CH | | |
| —C(OC₂H₅)₃ | CH₃ | H | O | CH₃ | OCH₃ | CH | |
| —C(OC₂H₅)₃ | CH₃ | H | O | CH₃ | CH₃ | CH | |
| —C(OC₂H₅)₃ | CH₃ | H | O | Cl | OCH₃ | CH | |
| —C(OC₂H₅)₃ | CH₃ | H | O | CH₃ | OCH₃ | N | |
| —C(OC₂H₅)₃ | CH₃ | H | O | OCH₃ | OCH₃ | N | |

TABLE IIb

General Structure IIb

| R₁ | R₁₁ | R | W | X | Y | Z | m.p. °C. |
|---|---|---|---|---|---|---|---|
| 1,3-dioxolan-2-yl | CH₃ | H | O | CH₃ | CH₃ | CH | |
| 1,3-dioxolan-2-yl | CH₃ | H | O | CH₃ | OCH₃ | CH | |
| 1,3-dioxolan-2-yl | CH₃ | H | O | OCH₃ | OCH₃ | CH | |
| 1,3-dioxolan-2-yl | CH₃ | H | O | Cl | OCH₃ | CH | |
| 1,3-dioxolan-2-yl | CH₃ | H | O | CH₃ | OCH₃ | N | |
| 1,3-dioxolan-2-yl | CH₃ | H | O | OCH₃ | OCH₃ | N | |
| 1,3-dioxolan-2-yl | CH₃ | H | O | OCH₂CH₂F | NHCH₃ | N | |
| 1,3-dioxolan-2-yl | CH₃ | H | O | OCH₂CF₃ | NHCH₃ | N | |
| 1,3-dioxolan-2-yl | CH₃ | H | O | OCH₃ | CH₂OCH₃ | CH | |
| 1,3-dioxolan-2-yl | CH₃ | H | O | OCH₃ | cyclo-propyl | CH | |
| 1,3-dioxolan-2-yl | C₃H₇ | H | O | OCH₃ | CH₃ | CH | |
| 1,3-dioxolan-2-yl | CH₃ | H | S | CH₃ | CH₃ | CH | |
| 1,3-dioxolan-2-yl | CH₃ | CH₃ | O | CH₃ | CH₃ | CH | |
| CH(OCH₃)₂ | CH₃ | H | O | OCH₃ | CH₃ | CH | |
| CH(OCH₃)₂ | CH₃ | H | O | OCH₃ | CH₃ | N | |
| CH(OCH₃)₂ | CH₃ | H | O | CH₃ | CH₃ | CH | |
| CH(OCH₃)₂ | CH₃ | H | O | Cl | OCH₃ | CH | |
| 1,3-dithiolan-2-yl | CH₃ | H | O | OCH₃ | CH₃ | CH | |
| 1,3-dithiolan-2-yl | CH₃ | H | O | OCH₃ | CH₃ | N | |
| 1,3-dithiolan-2-yl | CH₃ | H | O | CH₃ | CH₃ | CH | |
| 1,3-dithiolan-2-yl | CH₃ | H | O | Cl | OCH₃ | CH | |
| —C(OCH₃)₃ | CH₃ | H | O | OCH₃ | OCH₃ | CH | |
| —C(OCH₃)₃ | CH₃ | H | O | CH₃ | OCH₃ | CH | |
| —C(OCH₃)₃ | CH₃ | H | O | CH₃ | CH₃ | CH | |
| —C(OCH₃)₃ | CH₃ | H | O | Cl | OCH₃ | CH | |

TABLE IIb-continued

General Structure IIb

| R₁ | R₁₁ | R | W | X | Y | Z | m.p. °C. |
|---|---|---|---|---|---|---|---|
| —C(OCH₃)₃ | CH₃ | H | O | CH₃ | OCH₃ | N | |
| —C(OCH₃)₃ | CH₃ | H | O | OCH₃ | OCH₃ | N | |
| —C(OC₂H₅)₃ | CH₃ | H | O | OCH₃ | OCH₃ | CH | |
| —C(OC₂H₅)₃ | CH₃ | H | O | CH₃ | OCH₃ | CH | |
| —C(OC₂H₅)₃ | CH₃ | H | O | CH₃ | CH₃ | CH | |
| —C(OC₂H₅)₃ | CH₃ | H | O | Cl | OCH₃ | CH | |
| —C(OC₂H₅)₃ | CH₃ | H | O | CH₃ | OCH₃ | N | |
| —C(OC₂H₅)₃ | CH₃ | H | O | OCH₃ | OCH₃ | N | |

TABLE IIc

General Structure IIc

| R₁ | R₁₁ | R | W | X | Y | Z | m.p. °C. |
|---|---|---|---|---|---|---|---|
| 1,3-dioxolan-2-yl | CH₃ | H | O | CH₃ | CH₃ | CH | |
| 1,3-dioxolan-2-yl | CH₃ | H | O | CH₃ | OCH₃ | CH | |
| 1,3-dioxolan-2-yl | CH₃ | H | O | OCH₃ | OCH₃ | CH | |
| 1,3-dioxolan-2-yl | CH₃ | H | O | Cl | OCH₃ | CH | |
| 1,3-dioxolan-2-yl | CH₃ | H | O | CH₃ | OCH₃ | N | |
| 1,3-dioxolan-2-yl | CH₃ | H | O | OCH₃ | OCH₃ | N | |
| 1,3-dioxolan-2-yl | CH₃ | H | O | OCH₂CH₂F | NHCH₃ | N | |
| 1,3-dioxolan-2-yl | CH₃ | H | O | OCH₂CF₃ | NHCH₃ | N | |
| 1,3-dioxolan-2-yl | CH₃ | H | O | OCH₃ | CH₂OCH₃ | CH | |
| 1,3-dioxolan-2-yl | CH₃ | H | O | OCH₃ | cyclopropyl | CH | |
| 1,3-dioxolan-2-yl | C₃H₇ | H | O | OCH₃ | CH₃ | CH | |
| 1,3-dioxolan-2-yl | CH₃ | H | S | CH₃ | CH₃ | CH | |
| 1,3-dioxolan-2-yl | CH₃ | CH₃ | O | CH₃ | CH₃ | CH | |
| CH(OCH₃)₂ | CH₃ | H | O | OCH₃ | CH₃ | CH | |
| CH(OCH₃)₂ | CH₃ | H | O | OCH₃ | CH₃ | N | |
| CH(OCH₃)₂ | CH₃ | H | O | CH₃ | CH₃ | CH | |
| CH(OCH₃)₂ | CH₃ | H | O | Cl | OCH₃ | CH | |
| 1,3-dithiolan-2-yl | CH₃ | H | O | OCH₃ | CH₃ | CH | |
| 1,3-dithiolan-2-yl | CH₃ | H | O | OCH₃ | CH₃ | N | |
| 1,3-dithiolan-2-yl | CH₃ | H | O | CH₃ | CH₃ | CH | |
| 1,3-dithiolan-2-yl | CH₃ | H | O | Cl | OCH₃ | CH | |
| —C(OCH₃)₃ | CH₃ | H | O | OCH₃ | OCH₃ | CH | |
| —C(OCH₃)₃ | CH₃ | H | O | CH₃ | OCH₃ | CH | |
| —C(OCH₃)₃ | CH₃ | H | O | CH₃ | CH₃ | CH | |
| —C(OCH₃)₃ | CH₃ | H | O | Cl | OCH₃ | CH | |
| —C(OCH₃)₃ | CH₃ | H | O | CH₃ | OCH₃ | N | |
| —C(OCH₃)₃ | CH₃ | H | O | OCH₃ | OCH₃ | N | |
| —C(OC₂H₅)₃ | CH₃ | H | O | OCH₃ | OCH₃ | CH | |
| —C(OC₂H₅)₃ | CH₃ | H | O | CH₃ | OCH₃ | CH | |
| —C(OC₂H₅)₃ | CH₃ | H | O | CH₃ | CH₃ | CH | |
| —C(OC₂H₅)₃ | CH₃ | H | O | Cl | OCH₃ | CH | |
| —C(OC₂H₅)₃ | CH₃ | H | O | CH₃ | OCH₃ | N | |
| —C(OC₂H₅)₃ | CH₃ | H | O | OCH₃ | OCH₃ | N | |

TABLE III

General Structure III

| R₁ | R | W | X | Y | Z | m.p. °C. |
|---|---|---|---|---|---|---|
| 1,3-dioxolan-2-yl | H | O | CH₃ | CH₃ | CH | |
| 1,3-dioxolan-2-yl | H | O | CH₃ | OCH₃ | CH | |
| 1,3-dioxolan-2-yl | H | O | OCH₃ | OCH₃ | CH | |
| 1,3-dioxolan-2-yl | H | O | Cl | OCH₃ | CH | |
| 1,3-dioxolan-2-yl | H | O | CH₃ | OCH₃ | N | |
| 1,3-dioxolan-2-yl | H | O | OCH₃ | OCH₃ | N | |
| 1,3-dioxolan-2-yl | H | O | OCH₂CH₂F | NHCH₃ | N | |
| 1,3-dioxolan-2-yl | H | O | OCH₂CH₃ | NHCH₃ | N | |
| 1,3-dioxolan-2-yl | H | O | OCH₃ | CH₂OCH₃ | CH | |
| 1,3-dioxolan-2-yl | H | O | OCH₃ | cyclopropyl | CH | |
| 1,3-dioxolan-2-yl | H | O | OCH₃ | CH₃ | CH | |
| 1,3-dioxolan-2-yl | H | S | CH₃ | CH₃ | CH | |
| 1,3-dioxolan-2-yl | CH₃ | O | CH₃ | CH₃ | CH | |
| CH(OCH₃)₂ | H | O | OCH₃ | CH₃ | CH | |
| CH(OCH₃)₂ | H | O | OCH₃ | CH₃ | N | |
| CH(OCH₃)₂ | H | O | CH₃ | CH₃ | CH | |
| CH(OCH₃)₂ | H | O | Cl | OCH₃ | CH | |
| 1,3-dithiolan-2-yl | H | O | OCH₃ | CH₃ | CH | |
| 1,3-dithiolan-2-yl | H | O | OCH₃ | CH₃ | N | |
| 1,3-dithiolan-2-yl | H | O | CH₃ | CH₃ | CH | |
| 1,3-dithiolan-2-yl | H | O | Cl | OCH₃ | CH | |
| —C(OCH₃)₃ | H | O | OCH₃ | OCH₃ | CH | |
| —C(OCH₃)₃ | H | O | CH₃ | OCH₃ | CH | |

TABLE III-continued

General Structure III

| R₁ | R | W | X | Y | Z | m.p. °C. |
|---|---|---|---|---|---|---|
| —C(OCH₃)₃ | H | O | CH₃ | CH₃ | CH | |
| —C(OCH₃)₃ | H | O | Cl | OCH₃ | CH | |
| —C(OCH₃)₃ | H | O | CH₃ | OCH₃ | N | |
| —C(OCH₃)₃ | H | O | OCH₃ | OCH₃ | N | |
| —C(OC₂H₅)₃ | H | O | OCH₃ | OCH₃ | CH | |
| —C(OC₂H₅)₃ | H | O | CH₃ | OCH₃ | CH | |
| —C(OC₂H₅)₃ | H | O | CH₃ | CH₃ | CH | |
| —C(OC₂H₅)₃ | H | O | Cl | OCH₃ | CH | |
| —C(OC₂H₅)₃ | H | O | CH₃ | OCH₃ | N | |
| —C(OC₂H₅)₃ | H | O | OCH₃ | OCH₃ | N | |

TABLE IIIa

General Structure IIIa

| R₁ | R | W | X | Y | Z | m.p. °C. |
|---|---|---|---|---|---|---|
| 1,3-dioxolan-2-yl | H | O | CH₃ | CH₃ | CH | |
| 1,3-dioxolan-2-yl | H | O | CH₃ | OCH₃ | CH | |
| 1,3-dioxolan-2-yl | H | O | OCH₃ | OCH₃ | CH | |
| 1,3-dioxolan-2-yl | H | O | Cl | OCH₃ | CH | |
| 1,3-dioxolan-2-yl | H | O | CH₃ | OCH₃ | N | |
| 1,3-dioxolan-2-yl | H | O | OCH₃ | OCH₃ | N | |
| 1,3-dioxolan-2-yl | H | O | OCH₂CH₂F | NHCH₃ | N | |
| 1,3-dioxolan-2-yl | H | O | OCH₂CF₃ | NHCH₃ | N | |
| 1,3-dioxolsn-2-yl | H | O | OCH₃ | CH₂OCH₃ | CH | |
| 1,3-dioxolan-2-yl | H | O | OCH₃ | cyclopropyl | CH | |
| 1,3-dioxolan-2-yl | H | S | CH₃ | CH₃ | CH | |
| 1,3-dioxolan-2-yl | CH₃ | O | CH₃ | CH₃ | CH | |
| CH(OCH₃)₂ | H | O | OCH₃ | CH₃ | CH | |
| CH(OCH₃)₂ | H | O | OCH₃ | CH₃ | N | |
| CH(OCH₃)₂ | H | O | CH₃ | CH₃ | CH | |
| CH(OCH₃)₂ | H | O | Cl | OCH₃ | CH | |
| 1,3-dithiolan-2-yl | H | O | OCH₃ | CH₃ | CH | |
| 1,3-dithiolan-2-yl | H | O | OCH₃ | CH₃ | N | |
| 1,3-dithiolan-2-yl | H | O | CH₃ | CH₃ | CH | |
| 1,3-dithiolan-2-yl | H | O | Cl | OCH₃ | CH | |
| —C(OCH₃)₃ | H | O | OCH₃ | OCH₃ | CH | |
| —C(OCH₃)₃ | H | O | CH₃ | OCH₃ | CH | |
| —C(OCH₃)₃ | H | O | CH₃ | CH₃ | CH | |
| —C(OCH₃)₃ | H | O | Cl | OCH₃ | CH | |
| —C(OCH₃)₃ | H | O | CH₃ | OCH₃ | N | |
| —C(OCH₃)₃ | H | O | OCH₃ | OCH₃ | N | |
| —C(OC₂H₅)₃ | H | O | OCH₃ | OCH₃ | CH | |
| —C(OC₂H₅)₃ | H | O | CH₃ | OCH₃ | CH | |
| —C(OC₂H₅)₃ | H | O | CH₃ | CH₃ | CH | |
| —C(OC₂H₅)₃ | H | O | Cl | OCH₃ | CH | |
| —C(OC₂H₅)₃ | H | O | CH₃ | OCH₃ | N | |
| —C(OC₂H₅)₃ | H | O | OCH₃ | OCH₃ | N | |

TABLE IIIb

General structure IIIb

| R₁ | R | W | X | Y | Z | m.p. °C. |
|---|---|---|---|---|---|---|
| 1,3-dioxolan-2-yl | H | O | CH₃ | CH₃ | CH | |
| 1,3-dioxolan-2-yl | H | O | CH₃ | OCH₃ | CH | |
| 1,3-dioxolan-2-yl | H | O | OCH₃ | OCH₃ | CH | |
| 1,3-dioxolan-2-yl | H | O | Cl | OCH₃ | CH | |
| 1,3-dioxolan-2-yl | H | O | CH₃ | OCH₃ | N | |
| 1,3-dioxolan-2-yl | H | O | OCH₃ | OCH₃ | N | |
| 1,3-dioxolan-2-yl | H | O | OCH₂CH₂F | NHCH₃ | N | |
| 1,3-dioxolan-2-yl | H | O | OCH₂CF₃ | NHCH₃ | N | |
| 1,3-dioxolan-2-yl | H | O | OCH₃ | CH₂OCH₃ | CH | |
| 1,3-dioxolan-2-yl | H | O | OCH₃ | cyclopropyl | CH | |
| 1,3-dioxolan-2-yl | H | O | OCH₃ | CH₃ | CH | |
| 1,3-dioxolan-2-yl | H | S | CH₃ | CH₃ | CH | |
| 1,3-dioxolan-2-yl | CH₃ | O | CH₃ | CH₃ | CH | |
| CH(OCH₃)₂ | H | O | OCH₃ | CH₃ | CH | |
| CH(OCH₃)₂ | H | O | OCH₃ | CH₃ | N | |
| CH(OCH₃)₂ | H | O | CH₃ | CH₃ | CH | |
| CH(OCH₃)₂ | H | O | Cl | OCH₃ | CH | |
| 1,3-dithiolan-2-yl | H | O | OCH₃ | CH₃ | CH | |
| 1,3-dithiolan-2-yl | H | O | OCH₃ | CH₃ | N | |
| 1,3-dithiolan-2-yl | H | O | CH₃ | CH₃ | CH | |
| 1,3-dithiolan-2-yl | H | O | Cl | OCH₃ | CH | |

TABLE IIIb-continued

General structure IIIb

| R1 | R | W | X | Y | Z | m.p. °C. |
|---|---|---|---|---|---|---|
| —C(OCH3)3 | H | O | OCH3 | OCH3 | CH | |
| —C(OCH3)3 | H | O | CH3 | OCH3 | CH | |
| —C(OCH3)3 | H | O | CH3 | CH3 | CH | |
| —C(OCH3)3 | H | O | Cl | OCH3 | CH | |
| —C(OCH3)3 | H | O | CH3 | OCH3 | N | |
| —C(OCH3)3 | H | O | OCH3 | OCH3 | N | |
| —C(OC2H5)3 | H | O | OCH3 | OCH3 | CH | |
| —C(OC2H5)3 | H | O | CH3 | OCH3 | CH | |
| —C(OC2H5)3 | H | O | CH3 | CH3 | CH | |
| —C(OC2H5)3 | H | O | Cl | OCH3 | CH | |
| —C(OC2H5)3 | H | O | CH3 | OCH3 | N | |
| —C(OC2H5)3 | H | O | OCH3 | OCH3 | N | |

TABLE IV

General Structure IV

| R1 | R2 | R | W | W1 | A | X1 | Y1 | Y2 | m.p. °C. |
|---|---|---|---|---|---|---|---|---|---|
| 1,3-dioxolan-2-yl | H | H | O | S | A-2 | CH3 | O | — | |
| 1,3-dioxolan-2-yl | H | H | O | S | A-2 | OCH3 | O | — | |
| 1,3-dioxolan-2-yl | H | H | O | S | A-2 | OCF2H | O | — | |
| 1,3-dioxolan-2-yl | H | H | O | S | A-2 | CH3 | CH2 | — | |
| 1,3-dioxolan-2-yl | H | H | O | S | A-2 | OCH3 | CH2 | — | |
| 1,3-dioxolan-2-yl | H | H | O | S | A-2 | OC2H5 | CH2 | — | |
| 1,3-dioxolan-2-yl | H | H | O | O | A-2 | CH3 | O | — | |
| 1,3-dioxolan-2-yl | H | H | O | O | A-2 | OCH3 | O | — | |
| 1,3-dioxolan-2-yl | H | H | O | O | A-2 | OCH3 | CH2 | — | |
| 1,3-dithiolan-2-yl | H | H | O | S | A-2 | CH3 | O | — | |
| 1,3-dithiolan-2-yl | H | H | O | S | A-2 | OCH3 | CH2 | — | |
| 1,3-dithiolan-2-yl | H | H | O | O | A-2 | CH3 | O | — | |
| 1,3-dithiolan-2-yl | H | H | O | O | A-2 | OCH3 | CH2 | — | |
| CH(OCH3)2 | H | H | O | S | A-2 | CH3 | O | — | |
| CH(OCH3)2 | H | H | O | O | A-2 | CH3 | O | — | |
| 1,3-dioxolan-2-yl | H | H | O | S | A-3 | CH3 | — | — | |
| 1,3-dioxolan-2-yl | H | H | O | O | A-3 | OCH3 | — | — | |
| 1,3-dioxolan-2-yl | H | H | O | O | A-3 | OCF2H | — | — | |
| 1,3-dioxolan-2-yl | H | H | O | S | A-4 | OCH3 | — | CH3 | |
| 1,3-dioxolan-2-yl | H | H | O | S | A-4 | CH3 | — | CH3 | |
| 1,3-dioxolan-2-yl | H | H | O | S | A-4 | OC2H5 | — | H | |
| 1,3-dioxolan-2-yl | H | H | O | O | A-4 | CH3 | — | CH3 | |
| 1,3-dioxolan-2-yl | H | H | O | O | A-4 | OCF2H | — | CH3 | |
| 1,3-dithiolan-2-yl | H | H | O | S | A-3 | CH3 | — | — | |
| 1,3-dithiolan-2-yl | H | H | O | S | A-4 | CH3 | — | CH3 | |
| CH(OCH3)2 | H | H | O | S | A-3 | OCH3 | — | — | |
| CH(OCH3)2 | H | H | O | S | A-4 | OCH3 | — | CH3 | |
| C(OCH3)3 | H | H | O | S | A-2 | CH3 | O | — | |
| C(OCH3)3 | H | H | O | S | A-2 | OCH3 | O | — | |
| C(OCH3)3 | H | H | O | S | A-2 | OCF2H | O | — | |
| C(OCH3)3 | H | H | O | S | A-2 | CH3 | CH2 | — | |
| C(OCH3)3 | H | H | O | S | A-2 | OCH3 | CH2 | — | |
| C(OCH3)3 | H | H | O | S | A-2 | OC2H5 | CH2 | — | |
| C(OCH3)3 | H | H | O | O | A-3 | CH3 | — | — | |
| C(OCH3)3 | H | H | O | O | A-3 | OCH3 | — | — | |
| C(OCH3)3 | H | H | O | O | A-3 | OCF2H | — | — | |
| C(OCH3)3 | H | H | O | O | A-4 | OCH3 | — | CH3 | |
| C(OCH3)3 | H | H | O | O | A-4 | CH3 | — | CH3 | |
| C(OCH3)3 | H | H | O | O | A-4 | OC2H5 | — | H | |
| C(OCH3)3 | H | H | O | O | A-4 | OCF2H | — | CH3 | |
| C(OCH3)3 | H | H | O | O | A-2 | CH3 | O | — | |
| C(OC2H5)3 | H | H | O | O | A-2 | CH3 | O | — | |
| C(OC2H5)3 | H | H | O | S | A-2 | CH3 | O | — | |

| | | | | | | X2 | Y3 | | |
|---|---|---|---|---|---|---|---|---|---|
| C(OCH3)3 | H | H | O | S | A-5 | CH3 | OCH3 | | |
| C(OCH3)3 | H | H | O | S | A-5 | CH3 | OC2H5 | | |
| C(OCH3)3 | H | H | O | S | A-5 | CH3 | SCH3 | | |
| C(OCH3)3 | H | H | O | S | A-5 | CH3 | SC2H5 | | |
| C(OCH3)3 | H | H | O | S | A-5 | CH3 | CH3 | | |
| C(OCH3)3 | H | H | O | S | A-5 | CH3 | C2H5 | | |
| C(OCH3)3 | H | H | O | S | A-5 | CH3 | OCF2H | | |
| C(OCH3)3 | H | H | O | S | A-5 | CH3 | SCF2H | | |
| C(OCH3)3 | H | H | O | S | A-5 | C2H5 | OCH3 | | |
| C(OCH3)3 | H | H | O | S | A-5 | CH2CF3 | OCH3 | | |
| C(OCH3)3 | H | H | O | O | A-5 | CH3 | OCH3 | | |

| | | | | | | X2 | Y3 | — | |
|---|---|---|---|---|---|---|---|---|---|
| 1,3-dioxolan-2-yl | H | H | O | S | A-5 | CH3 | OCH3 | — | |
| 1,3-dioxolan-2-yl | H | H | O | S | A-5 | CH3 | OC2H5 | — | |

TABLE IV-continued

General Structure IV

| R₁ | R₂ | R | W | W₁ | A | X₁ | Y₁ | Y₂ | m.p. °C. |
|---|---|---|---|---|---|---|---|---|---|
| 1,3-dioxolan-2-yl | H | H | O | S | A-5 | CH₃ | SCH₃ | — | |
| 1,3-dioxolan-2-yl | H | H | O | S | A-5 | CH₃ | SC₂H₅ | — | |
| 1,3-dioxolan-2-yl | H | H | O | S | A-5 | CH₃ | OCF₂H | — | |
| 1,3-dioxolan-2-yl | H | H | O | S | A-5 | CH₃ | SCF₂H | — | |
| CH(OCH₃)₂ | H | H | O | S | A-5 | CH₃ | OCH₃ | — | |
| CH(OCH₃)₂ | H | H | O | S | A-5 | CH₃ | OC₂H₅ | — | |
| CH(OCH₃)₂ | H | H | O | S | A-5 | CH₃ | SCH₃ | — | |
| CH(OCH₃)₂ | H | H | O | S | A-5 | CH₃ | SC₂H₅ | — | |
| CH(OCH₃)₂ | H | H | O | S | A-5 | CH₃ | OCF₂H | — | |
| CH(OCH₃)₂ | H | H | O | S | A-5 | CH₃ | SCF₂H | — | |
| CH(OCH₃)₂ | H | H | O | O | A-5 | CH₃ | OCH₃ | — | |

| | | | | | | X₃ | | | |
|---|---|---|---|---|---|---|---|---|---|
| C(OCH₃)₃ | H | H | O | S | A-6 | CH₃ | — | — | |
| C(OCH₃)₃ | H | H | O | S | A-6 | OCH₃ | — | — | |
| 1,3-dioxolan-2-yl | H | H | O | S | A-6 | CH₃ | — | — | |
| 1,3-dioxolan-2-yl | H | H | O | S | A-6 | OCH₃ | — | — | |
| CH(OCH₃)₂ | H | H | O | S | A-6 | CH₃ | — | — | |
| CH(OCH₃)₂ | H | H | O | S | A-6 | OCH₃ | — | — | |
| CH(OCH₃)₂ | H | H | O | O | A-6 | CH₃ | — | — | |

| | | | | | | X₄ | Y₄ | Z | |
|---|---|---|---|---|---|---|---|---|---|
| CH(OCH₃)₂ | H | H | O | S | A-7 | CH₃ | CH₃ | CH | |
| CH(OCH₃)₂ | H | H | O | S | A-7 | OCH₃ | OCH₃ | CH | |
| 1,3-dioxolan-2-yl | H | H | O | S | A-7 | CH₃ | CH₃ | CH | |
| 1,3-dioxolan-2-yl | H | H | O | S | A-7 | OCH₃ | OCH₃ | CH | |
| C(OCH₃)₃ | H | H | O | S | A-7 | CH₃ | CH₃ | CH | |
| C(OCH₃)₃ | H | H | O | S | A-7 | CH₃ | CH₃ | N | |
| C(OCH₃)₃ | H | H | O | S | A-7 | OCH₃ | CH₃ | CH | |
| C(OCH₃)₃ | H | H | O | S | A-7 | OCH₃ | CH₃ | N | |
| C(OCH₃)₃ | H | H | O | S | A-7 | OCH₃ | OCH₃ | N | |
| C(OCH₃)₃ | H | H | O | S | A-7 | Cl | CH₃ | CH | |
| C(OCH₃)₃ | H | H | O | S | A-7 | OCH₃ | Cl | CH | |
| C(OCH₃)₃ | H | H | O | S | A-7 | OC₂H₅ | CH₃ | CH | |
| C(OCH₃)₃ | H | H | O | S | A-7 | CH₂OCH₃ | CH₃ | N | |
| C(OCH₃)₃ | H | H | O | S | A-7 | CH₂OCH₃ | OCH₃ | CH | |
| C(OCH₃)₃ | H | H | O | S | A-7 | OC₂H₅ | OC₂H₅ | N | |
| C(OCH₃)₃ | H | H | O | O | A-7 | CH₃ | CH₃ | CH | |

TABLE IVa

General Structure IVa

| R₁ | R₁₂ | R | W | W₁ | A | X₁ | Y₁ | Y₂ | m.p. °C. |
|---|---|---|---|---|---|---|---|---|---|
| 1,3-dioxolan-2-yl | H | H | O | S | A-2 | CH₃ | O | — | |
| 1,3-dioxolan-2-yl | H | H | O | S | A-2 | OCH₃ | O | — | |
| 1,3-dioxolan-2-yl | H | H | O | S | A-2 | OCF₂H | O | — | |
| 1,3-dioxolan-2-yl | H | H | O | S | A-2 | CH₃ | CH₂ | — | |
| 1,3-dioxolan-2-yl | H | H | O | S | A-2 | OCH₃ | CH₂ | — | |
| 1,3-dioxolan-2-yl | H | H | O | S | A-2 | OC₂H₅ | CH₂ | — | |
| 1,3-dioxolan-2-yl | H | H | O | O | A-2 | CH₃ | O | — | |
| 1,3-dioxolan-2-yl | H | H | O | O | A-2 | OCH₃ | O | — | |
| 1,3-dioxolan-2-yl | H | H | O | O | A-2 | OCH₃ | CH₂ | — | |
| 1,3-dithiolan-2-yl | H | H | O | S | A-2 | CH₃ | O | — | |
| 1,3-dithiolan-2-yl | H | H | O | S | A-2 | OCH₃ | CH | — | |
| 1,3-dithiolan-2-yl | H | H | O | O | A-2 | CH₃ | O | — | |
| 1,3-dithiolan-2-yl | H | H | O | O | A-2 | OCH₃ | CH | — | |
| CH(OCH₃)₂ | H | H | O | S | A-2 | CH₃ | O | — | |
| CH(OCH₃)₂ | H | H | O | O | A-2 | CH₃ | O | — | |
| 1,3-dioxolan-2-yl | H | H | O | S | A-3 | CH₃ | — | — | |
| 1,3-dioxolan-2-yl | H | H | O | S | A-3 | OCH₃ | — | — | |
| 1,3-dioxolan-2-yl | H | H | O | O | A-3 | OCF₂H | — | — | |
| 1,3-dioxolan-2-yl | H | H | O | S | A-4 | OCH₃ | — | CH₃ | |
| 1,3-dioxolan-2-yl | H | H | O | S | A-4 | CH₃ | — | CH₃ | |
| 1,3-dioxolan-2-yl | H | H | O | S | A-4 | OC₂H₅ | — | H | |
| 1,3-dioxolan-2-yl | H | H | O | O | A-4 | CH₃ | — | CH₃ | |
| 1,3-dioxolan-2-yl | H | H | O | O | A-4 | OCF₂H | — | CH₃ | |
| 1,3-dithiolan-2-yl | H | H | O | S | A-3 | CH₃ | — | — | |
| 1,3-dithiolan-2-yl | H | H | O | S | A-4 | CH₃ | — | CH₃ | |
| CH(OCH₃)₂ | H | H | O | S | A-3 | OCH₃ | — | — | |

TABLE IVa-continued

General Structure IVa

| | | | | | | | | |
|---|---|---|---|---|---|---|---|---|
| CH(OCH$_3$)$_2$ | H | H | O | S | A-4 | OCH$_3$ | — | CH$_3$ |
| C(OCH$_3$)$_3$ | H | H | O | S | A-2 | CH$_3$ | O | — |
| C(OCH$_3$)$_3$ | H | H | O | S | A-2 | OCH$_3$ | O | — |
| C(OCH$_3$)$_3$ | H | H | O | S | A-2 | OCF$_2$H | O | — |
| C(OCH$_3$)$_3$ | H | H | O | S | A-2 | CH$_3$ | CH$_2$ | — |
| C(OCH$_3$)$_3$ | H | H | O | S | A-2 | OCH$_3$ | CH$_2$ | — |
| C(OCH$_3$)$_2$ | H | H | O | S | A-2 | OC$_2$H$_5$ | CH$_2$ | — |
| C(OCH$_3$)$_3$ | H | H | O | O | A-3 | CH$_3$ | — | — |
| C(OCH$_3$)$_3$ | H | H | O | O | A-3 | OCH$_3$ | — | — |
| C(OCH$_3$)$_3$ | H | H | O | O | A-3 | OCF$_2$H | — | — |
| C(OCH$_3$)$_3$ | H | H | O | O | A-4 | OCH$_3$ | — | CH$_3$ |
| C(OCH$_3$)$_3$ | H | H | O | O | A-4 | CH$_3$ | — | CH$_3$ |
| C(OCH$_3$)$_3$ | H | H | O | O | A-4 | OC$_2$H$_5$ | — | H |
| C(OCH$_3$)$_3$ | H | H | O | O | A-4 | OCF$_2$H | — | CH$_3$ |
| C(OCH$_3$)$_3$ | H | H | O | O | A-2 | CH$_3$ | O | — |
| C(OC$_2$H$_5$)$_3$ | H | H | O | O | A-2 | CH$_3$ | O | — |
| C(OC$_2$H$_5$)$_3$ | H | H | O | S | A-2 | CH$_3$ | O | — |

| | | | | | | X$_2$ | Y$_3$ | |
|---|---|---|---|---|---|---|---|---|
| C(OCH$_3$)$_3$ | H | H | O | S | A-5 | CH$_3$ | OCH$_3$ | |
| C(OCH$_3$)$_3$ | H | H | O | S | A-5 | CH$_3$ | OC$_2$H$_5$ | |
| C(OCH$_3$)$_3$ | H | H | O | S | A-5 | CH$_3$ | SCH$_3$ | |
| C(OCH$_3$)$_3$ | H | H | O | S | A-5 | CH$_3$ | SC$_2$H$_5$ | |
| C(OCH$_3$)$_3$ | H | H | O | S | A-5 | CH$_3$ | CH$_3$ | |
| C(OCH$_3$)$_3$ | H | H | O | S | A-5 | CH$_3$ | C$_2$H$_5$ | |
| C(OCH$_3$)$_3$ | H | H | O | S | A-5 | CH$_3$ | OCF$_2$H | |
| C(OCH$_3$)$_3$ | H | H | O | S | A-5 | CH$_3$ | SCF$_2$H | |
| C(OCH$_3$)$_3$ | H | H | O | S | A-5 | C$_2$H$_5$ | OCH$_3$ | |
| C(OCH$_3$)$_3$ | H | H | O | S | A-5 | CH$_2$CF$_3$ | OCH$_3$ | |
| C(OCH$_3$)$_3$ | H | H | O | O | A-5 | CH$_3$ | OCH$_3$ | |
| 1,3-dioxolan-2-yl | H | H | O | S | A-5 | CH$_3$ | OCH$_3$ | — |
| 1,3-dioxolan-2-yl | H | H | O | S | A-5 | CH$_3$ | OC$_2$H$_5$ | — |
| 1,3-dioxolan-2-yl | H | H | O | S | A-5 | CH$_3$ | SCH$_3$ | — |
| 1,3-dioxolan-2-yl | H | H | O | S | A-5 | CH$_3$ | SC$_2$H$_5$ | — |
| 1,3-dioxolan-2-yl | H | H | O | S | A-5 | CH$_3$ | OCF$_2$H | — |
| 1,3-dioxolan-2-yl | H | H | O | S | A-5 | CH$_3$ | SCF$_2$H | — |
| CH(OCH$_3$)$_2$ | H | H | O | S | A-5 | CH$_3$ | OCH$_3$ | — |
| CH(OCH$_3$)$_2$ | H | H | O | S | A-5 | CH$_3$ | OC$_2$H$_5$ | — |
| CH(OCH$_3$)$_2$ | H | H | O | S | A-5 | CH$_3$ | SCH$_3$ | — |
| CH(OCH$_3$)$_2$ | H | H | O | S | A-5 | CH$_3$ | SC$_2$H$_5$ | — |
| CH(OCH$_3$)$_2$ | H | H | O | S | A-5 | CH$_3$ | OCF$_2$H | — |
| CH(OCH$_3$)$_2$ | H | H | O | S | A-5 | CH$_3$ | SCF$_2$H | — |
| CH(OCH$_3$)$_2$ | H | H | O | O | A-5 | CH$_3$ | OCH$_3$ | — |

| | | | | | | X$_3$ | | |
|---|---|---|---|---|---|---|---|---|
| C(OCH$_3$)$_3$ | H | H | O | S | A-6 | CH$_3$ | — | — |
| C(OCH$_3$)$_3$ | H | H | O | S | A-6 | OCH$_3$ | — | — |
| 1,3-dioxolan-2-yl | H | H | O | S | A-6 | CH$_3$ | — | — |
| 1,3-dioxolan-2-yl | H | H | O | S | A-6 | OCH$_3$ | — | — |
| CH(OCH$_3$)$_2$ | H | H | O | S | A-6 | CH$_3$ | — | — |
| CH(OCH$_3$)$_2$ | H | H | O | S | A-6 | OCH$_3$ | — | — |
| CH(OCH$_3$)$_2$ | H | H | O | O | A-6 | CH$_3$ | — | — |

| | | | | | | X$_4$ | Y$_4$ | Z |
|---|---|---|---|---|---|---|---|---|
| CH(OCH$_3$)$_2$ | H | H | O | S | A-7 | CH$_3$ | CH$_3$ | CH |
| CH(OCH$_3$)$_2$ | H | H | O | S | A-7 | OCH$_3$ | OCH$_3$ | CH |
| 1,3-dioxolan-2-yl | H | H | O | S | A-7 | CH$_3$ | CH$_3$ | CH |
| 1,3-dioxolan-2-yl | H | H | O | S | A-7 | OCH$_3$ | OCH$_3$ | CH |
| C(OCH$_3$)$_3$ | H | H | O | S | A-7 | CH$_3$ | CH$_3$ | CH |
| C(OCH$_3$)$_3$ | H | H | O | S | A-7 | CH$_3$ | CH$_3$ | N |
| C(OCH$_3$)$_3$ | H | H | O | S | A-7 | OCH$_3$ | CH$_3$ | CH |
| C(OCH$_3$)$_3$ | H | H | O | S | A-7 | OCH$_3$ | CH$_3$ | N |
| C(OCH$_3$)$_3$ | H | H | O | S | A-7 | OCH$_3$ | OCH$_3$ | N |
| C(OCH$_3$)$_3$ | H | H | O | S | A-7 | Cl | CH$_3$ | CH |
| C(OCH$_3$)$_3$ | H | H | O | S | A-7 | OCH$_3$ | Cl | CH |
| C(OCH$_3$)$_3$ | H | H | O | S | A-7 | OC$_2$H$_5$ | CH$_3$ | CH |
| C(OCH$_3$)$_3$ | H | H | O | S | A-7 | CH$_2$OCH$_3$ | CH$_3$ | N |
| C(OCH$_3$)$_3$ | H | H | O | S | A-7 | CH$_2$OCH$_3$ | OCH$_3$ | CH |
| C(OCH$_3$)$_3$ | H | H | O | S | A-7 | OC$_2$H$_5$ | OC$_2$H$_5$ | N |
| C(OCH$_3$)$_3$ | H | H | O | O | A-7 | CH$_3$ | CH$_3$ | CH |

TABLE IVb

General Structure IVb

| R₁ | R₁₂ | R | W | W₁ | A | X₁ | Y₁ | Y₂ | m.p. °C. |
|---|---|---|---|---|---|---|---|---|---|
| 1,3-dioxolan-2-yl | H | H | O | S | A-2 | $CH_3$ | O | — | |
| 1,3-dioxolan-2-yl | H | H | O | S | A-2 | $OCH_3$ | O | — | |
| 1,3-dioxolan-2-yl | H | H | O | S | A-2 | $OCF_2H$ | O | — | |
| 1,3-dioxolan-2-yl | H | H | O | S | A-2 | $CH_3$ | $CH_2$ | — | |
| 1,3-dioxolan-2-yl | H | H | O | S | A-2 | $OCH_3$ | $CH_2$ | — | |
| 1,3-dioxolan-2-yl | H | H | O | S | A-2 | $OC_2H_5$ | $CH_2$ | — | |
| 1,3-dioxolan-2-yl | H | H | O | O | A-2 | $CH_3$ | O | — | |
| 1,3-dioxolan-2-yl | H | H | O | O | A-2 | $OCH_3$ | O | — | |
| 1,3-dioxolan-2-yl | H | H | O | O | A-2 | $OCH_3$ | $CH_2$ | — | |
| 1,3-dithiolan-2-yl | H | H | O | S | A-2 | $CH_3$ | O | — | |
| 1,3-dithiolan-2-yl | H | H | O | S | A-2 | $OCH_3$ | CH | — | |
| 1,3-dithiolan-2-yl | H | H | O | O | A-2 | $CH_3$ | O | — | |
| 1,3-dithiolan-2-yl | H | H | O | O | A-2 | $OCH_3$ | CH | — | |
| $CH(OCH_3)_2$ | H | H | O | S | A-2 | $CH_3$ | O | — | |
| $CH(OCH_3)_2$ | H | H | O | O | A-2 | $CH_3$ | O | — | |
| 1,3-dioxolan-2-yl | H | H | O | S | A-3 | $CH_3$ | — | — | |
| 1,3-dioxolan-2-yl | H | H | O | S | A-3 | $OCH_3$ | — | — | |
| 1,3-dioxolan-2-yl | H | H | O | O | A-3 | $OCF_2H$ | — | — | |
| 1,3-dioxolan-2-yl | H | H | O | S | A-4 | $OCH_3$ | — | $CH_3$ | |
| 1,3-dioxolan-2-yl | H | H | O | S | A-4 | $CH_3$ | — | $CH_3$ | |
| 1,3-dioxolan-2-yl | H | H | O | S | A-4 | $OC_2H_5$ | — | H | |
| 1,3-dioxolan-2-yl | H | H | O | O | A-4 | $CH_3$ | — | $CH_3$ | |
| 1,3-dioxolan-2-yl | H | H | O | O | A-4 | $OCF_2H$ | — | $CH_3$ | |
| 1,3-dithiolan-2-yl | H | H | O | S | A-3 | $CH_3$ | — | — | |
| 1,3-dithiolan-2-yl | H | H | O | S | A-4 | $CH_3$ | — | $CH_3$ | |
| $CH(OCH_3)_2$ | H | H | O | S | A-3 | $OCH_3$ | — | — | |
| $CH(OCH_3)_2$ | H | H | O | S | A-4 | $OCH_3$ | — | $CH_3$ | |
| $C(OCH_3)_3$ | H | H | O | S | A-2 | $CH_3$ | O | — | |
| $C(OCH_3)_3$ | H | H | O | S | A-2 | $OCH_3$ | O | — | |
| $C(OCH_3)_3$ | H | H | O | S | A-2 | $OCF_2H$ | O | — | |
| $C(OCH_3)_3$ | H | H | O | S | A-2 | $CH_3$ | $CH_2$ | — | |
| $C(OCH_3)_3$ | H | H | O | S | A-2 | $OCH_3$ | $CH_2$ | — | |
| $C(OCH_3)_3$ | H | H | O | S | A-2 | $OC_2H_5$ | $CH_2$ | — | |
| $C(OCH_3)_3$ | H | H | O | O | A-3 | $CH_3$ | — | — | |
| $C(OCH_3)_3$ | H | H | O | O | A-3 | $OCH_3$ | — | — | |
| $C(OCH_3)_3$ | H | H | O | O | A-3 | $OCF_2H$ | — | — | |
| $C(OCH_3)_3$ | H | H | O | O | A-4 | $OCH_3$ | — | $CH_3$ | |
| $C(OCH_3)_3$ | H | H | O | O | A-4 | $CH_3$ | — | $CH_3$ | |
| $C(OCH_3)_3$ | H | H | O | O | A-4 | $OC_2H_5$ | — | H | |
| $C(OCH_3)_3$ | H | H | O | O | A-4 | $OCF_2H$ | — | $CH_3$ | |
| $C(OCH_3)_3$ | H | H | O | O | A-2 | $CH_3$ | O | — | |
| $C(OC_2H_5)_3$ | H | H | O | O | A-2 | $CH_3$ | O | — | |
| $C(OC_2H_5)_3$ | H | H | O | S | A-2 | $CH_3$ | O | — | |
| | | | | | | X₂ | Y₃ | | |
| $C(OCH_3)_3$ | H | H | O | S | A-5 | $CH_3$ | $OCH_3$ | | |
| $C(OCH_3)_3$ | H | H | O | S | A-5 | $CH_3$ | $OC_2H_5$ | | |
| $C(OCH_3)_3$ | H | H | O | S | A-5 | $CH_3$ | $SCH_3$ | | |
| $C(OCH_3)_3$ | H | H | O | S | A-5 | $CH_3$ | $SC_2H_5$ | | |
| $C(OCH_3)_3$ | H | H | O | S | A-5 | $CH_3$ | $CH_3$ | | |
| $C(OCH_3)_3$ | H | H | O | S | A-5 | $CH_3$ | $C_2H_5$ | | |
| $C(OCH_3)_3$ | H | H | O | S | A-5 | $CH_3$ | $OCF_2H$ | | |
| $C(OCH_3)_3$ | H | H | O | S | A-5 | $CH_3$ | $SCF_2H$ | | |
| $C(OCH_3)_3$ | H | H | O | S | A-5 | $C_2H_5$ | $OCH_3$ | | |
| $C(OCH_3)_3$ | H | H | O | S | A-5 | $CH_2CF_3$ | $OCH_3$ | | |
| $C(OCH_3)_3$ | H | H | O | O | A-5 | $CH_3$ | $OCH_3$ | | |
| 1,3-dioxolan-2-yl | H | H | O | S | A-5 | $CH_3$ | $OCH_3$ | — | |
| 1,3-dioxolan-2-yl | H | H | O | S | A-5 | $CH_3$ | $OC_2H_5$ | — | |
| 1,3-dioxolan-2-yl | H | H | O | S | A-5 | $CH_3$ | $SCH_3$ | — | |
| 1,3-dioxolan-2-yl | H | H | O | S | A-5 | $CH_3$ | $SC_2H_5$ | — | |
| 1,3-dioxolan-2-yl | H | H | O | S | A-5 | $CH_3$ | $OCF_2H$ | — | |
| 1,3-dioxolan-2-yl | H | H | O | S | A-5 | $CH_3$ | $SCF_2H$ | — | |
| $CH(OCH_3)_2$ | H | H | O | S | A-5 | $CH_3$ | $OCH_3$ | — | |
| $CH(OCH_3)_2$ | H | H | O | S | A-5 | $CH_3$ | $OC_2H_5$ | — | |
| $CH(OCH_3)_2$ | H | H | O | S | A-5 | $CH_3$ | $SCH_3$ | — | |
| $CH(OCH_3)_2$ | H | H | O | S | A-5 | $CH_3$ | $SC_2H_5$ | — | |
| $CH(OCH_3)_2$ | H | H | O | S | A-5 | $CH_3$ | $OCF_2H$ | — | |
| $CH(OCH_3)_2$ | H | H | O | S | A-5 | $CH_3$ | $SCF_2H$ | — | |
| $CH(OCH_3)_2$ | H | H | O | O | A-5 | $CH_3$ | $OCH_3$ | — | |
| | | | | | | X₃ | | | |
| $C(OCH_3)_3$ | H | H | O | S | A-6 | $CH_3$ | — | — | |
| $C(OCH_3)_3$ | H | H | O | S | A-6 | $OCH_3$ | — | — | |
| 1,3-dioxolan-2-yl | H | H | O | S | A-6 | $CH_3$ | — | — | |

TABLE IVb-continued

General Structure IVb

| | | | | | | | | |
|---|---|---|---|---|---|---|---|---|
| 1,3-dioxolan-2-yl | H | H | O | S | A-6 | OCH$_3$ | — | — |
| CH(OCH$_3$)$_2$ | H | H | O | S | A-6 | CH$_3$ | — | — |
| CH(OCH$_3$)$_2$ | H | H | O | S | A-6 | OCH$_3$ | — | — |
| CH(OCH$_3$)$_2$ | H | H | O | O | A-6 | CH$_3$ | — | — |
| | | | | | | X$_4$ | Y$_4$ | Z |
| CH(OCH$_3$)$_2$ | H | H | O | S | A-7 | CH$_3$ | CH$_3$ | CH |
| CH(OCH$_3$)$_2$ | H | H | O | S | A-7 | OCH$_3$ | OCH$_3$ | CH |
| 1,3-dioxolan-2-yl | H | H | O | S | A-7 | CH$_3$ | CH$_3$ | CH |
| 1,3-dioxolan-2-yl | H | H | O | S | A-7 | OCH$_3$ | OCH$_3$ | CH |
| C(OCH$_3$)$_3$ | H | H | O | S | A-7 | CH$_3$ | CH$_3$ | CH |
| C(OCH$_3$)$_3$ | H | H | O | S | A-7 | CH$_3$ | CH$_3$ | N |
| C(OCH$_3$)$_3$ | H | H | O | S | A-7 | OCH$_3$ | CH$_3$ | CH |
| C(OCH$_3$)$_3$ | H | H | O | S | A-7 | OCH$_3$ | CH$_3$ | N |
| C(OCH$_3$)$_3$ | H | H | O | S | A-7 | OCH$_3$ | OCH$_3$ | N |
| C(OCH$_3$)$_3$ | H | H | O | S | A-7 | Cl | CH$_3$ | CH |
| C(OCH$_3$)$_3$ | H | H | O | S | A-7 | OCH$_3$ | Cl | CH |
| C(OCH$_3$)$_3$ | H | H | O | S | A-7 | OC$_2$H$_5$ | CH$_3$ | CH |
| C(OCH$_3$)$_3$ | H | H | O | S | A-7 | CH$_2$OCH$_3$ | CH$_3$ | N |
| C(OCH$_3$)$_3$ | H | H | O | S | A-7 | CH$_2$OCH$_3$ | OCH$_3$ | CH |
| C(OCH$_3$)$_3$ | H | H | O | S | A-7 | OC$_2$H$_5$ | OC$_2$H$_5$ | N |
| C(OCH$_3$)$_3$ | H | H | O | O | A-7 | CH$_3$ | CH$_3$ | CH |

TABLE V

General Structure V

| R$_1$ | R$_{11}$ | R | W | A | X$_1$ | Y$_1$ | Y$_2$ | m.p. °C. |
|---|---|---|---|---|---|---|---|---|
| 1,3-dioxolan-2-yl | CH$_3$ | H | O | A-2 | CH$_3$ | O | — | |
| 1,3-dioxolan-2-yl | CH$_3$ | H | O | A-2 | OCF$_2$H | O | — | |
| 1,3-dioxolan-2-yl | CH$_3$ | H | O | A-2 | OCH$_3$ | O | — | |
| 1,3-dioxolan-2-yl | CH$_3$ | H | O | A-2 | CH$_3$ | CH$_2$ | — | |
| 1,3-dioxolan-2-yl | CH$_3$ | H | O | A-2 | OCH$_3$ | CH$_2$ | — | |
| 1,3-dioxolan-2-yl | CH$_3$ | H | O | A-2 | OC$_2$H$_5$ | CH$_2$ | — | |
| 1,3-dithiolan-2-yl | CH$_3$ | H | O | A-2 | CH$_3$ | O | — | |
| 1,3-dithiolan-2-yl | CH$_3$ | H | O | A-2 | OCH$_3$ | CH$_2$ | — | |
| 1,3-dioxolan-2-yl | CH$_3$ | H | O | A-3 | CH$_3$ | — | — | |
| 1,3-dioxolan-2-yl | CH$_3$ | H | O | A-3 | OCH$_3$ | — | — | |
| 1,3-dioxolan-2-yl | CH$_3$ | H | O | A-4 | CH$_3$ | — | CH$_3$ | |
| 1,3-dioxolan-2-yl | CH$_3$ | H | O | A-4 | OCH$_3$ | — | H | |
| 1,3-dioxolan-2-yl | CH$_3$ | H | O | A-4 | OCF$_2$H | — | CH$_3$ | |

| R$_1$ | R$_{11}$ | R$_{12}$ | R | W | A$_1$ | X$_1$ | Y$_2$ | Y | m.p. °C. |
|---|---|---|---|---|---|---|---|---|---|
| C(OCH$_3$)$_3$ | CH$_3$ | H | H | O | A-2 | CH$_3$ | O | — | |
| C(OCH$_3$)$_3$ | CH$_3$ | H | H | O | A-3 | CH$_3$ | — | — | |
| C(OCH$_3$)$_3$ | CH$_3$ | H | H | O | A-4 | CH$_3$ | — | CH$_3$ | |
| | | | | | | X$_2$ | Y$_2$ | | |
| C(OCH$_3$)$_3$ | CH$_3$ | H | H | O | A-5 | CH$_3$ | — | OCH$_3$ | |
| 1,3-dioxolan-2-yl | CH$_3$ | H | H | O | A-5 | CH$_3$ | SCH$_3$ | — | |
| | | | | | | X$_3$ | | | |
| C(CH$_3$)(OCH$_3$)$_2$ | CH$_3$ | H | H | O | A-6 | CH$_3$ | — | — | |
| C(OCH$_3$)$_3$ | CH$_3$ | H | H | O | A-6 | OCH$_3$ | — | — | |
| | | | | | | X$_4$ | Y$_4$ | Z | |
| 1,3-dioxolan-2-yl | CH$_3$ | H | H | O | A-7 | CH$_3$ | CH$_3$ | CH | |
| C(OCH$_3$)$_3$ | CH$_3$ | H | H | O | A-7 | OCH$_3$ | OCH$_3$ | CH | |

TABLE va

General Structure Va

| R$_1$ | R$_{11}$ | R | W | A | X$_1$ | Y$_1$ | Y$_2$ | m.p. °C. |
|---|---|---|---|---|---|---|---|---|
| 1,3-dioxolan-2-yl | CH$_3$ | H | O | A-2 | CH$_3$ | O | — | |
| 1,3-dioxolan-2-yl | CH$_3$ | H | O | A-2 | OCF$_2$H | O | — | |
| 1,3-dioxolan-2-yl | CH$_3$ | H | O | A-2 | OCH$_3$ | O | — | |
| 1,3-dioxolan-2-yl | CH$_3$ | H | O | A-2 | CH$_3$ | CH$_2$ | — | |
| 1,3-dioxolan-2-yl | CH$_3$ | H | O | A-2 | OCH$_3$ | CH$_2$ | — | |
| 1,3-dioxolan-2-yl | CH$_3$ | H | O | A-2 | OC$_2$H$_5$ | CH$_2$ | — | |
| 1,3-dithiolan-2-yl | CH$_3$ | H | O | A-2 | CH$_3$ | O | — | |
| 1,3-dithiolan-2-yl | CH$_3$ | H | O | A-2 | OCH$_3$ | CH$_2$ | — | |
| 1,3-dioxolan-2-yl | CH$_3$ | H | O | A-3 | CH$_3$ | — | — | |
| 1,3-dioxolan-2-yl | CH$_3$ | H | O | A-3 | OCH$_3$ | — | — | |
| 1,3-dioxolan-2-yl | CH$_3$ | H | O | A-4 | CH$_3$ | — | CH$_3$ | |

TABLE Va-continued

General Structure Va

| R₁ | R₁₁ | R | W | A | X₁ | Y₁ | Y₂ | m.p. °C |
|---|---|---|---|---|---|---|---|---|
| 1,3-dioxolan-2-yl | CH₃ | H | O | A-4 | OCH₃ | — | H | |
| 1,3-dioxolan-2-yl | CH₃ | H | O | A-4 | OCF₂H | — | CH₃ | |
| C(OCH₃)₃ | CH₃ | H | O | A-2 | CH₃ | O | — | |
| C(OCH₃)₃ | CH₃ | H | O | A-3 | CH₃ | — | — | |
| C(OCH₃)₃ | CH₃ | H | O | A-4 | CH₃ | — | CH₃ | |

| | | | | | X₂ | Y₂ | | |
|---|---|---|---|---|---|---|---|---|
| C(OCH₃)₃ | CH₃ | H | O | A-5 | CH₃ | OCH₃ | | |
| 1,3-dioxolan-2-yl | CH₃ | H | O | A-5 | CH₃ | SCH₃ | | |

| | | | | | X₃ | | | |
|---|---|---|---|---|---|---|---|---|
| C(CH₃)(OCH₃)₂ | CH₃ | H | O | A-6 | CH₃ | | | |
| C(OCH₃)₃ | CH₃ | H | O | A-6 | OCH₃ | | | |

| | | | | | X₄ | Y₄ | Z | |
|---|---|---|---|---|---|---|---|---|
| 1,3-dioxolan-2-yl | CH₃ | H | O | A-7 | CH₃ | CH₃ | CH | |
| C(OCH₃)₃ | CH₃ | H | O | A-7 | OCH₃ | OCH₃ | CH | |

TABLE Vb

General Structure Vb

| R₁ | R₁₁ | R | W | A | X₁ | Y₁ | Y₂ | m.p. °C |
|---|---|---|---|---|---|---|---|---|
| 1,3-dioxolan-2-yl | CH₃ | H | O | A-2 | CH₃ | O | — | |
| 1,3-dioxolan-2-yl | CH₃ | H | O | A-2 | OCF₂H | O | — | |
| 1,3-dioxolan-2-yl | CH₃ | H | O | A-2 | OCH₃ | O | — | |
| 1,3-dioxolan-2-yl | CH₃ | H | O | A-2 | CH₃ | CH₃ | — | |
| 1,3-dioxolan-2-yl | CH₃ | H | O | A-2 | OCH₃ | CH₂ | — | |
| 1,3-dioxolan-2-yl | CH₃ | H | O | A-2 | OC₂H₅ | CH₂ | — | |
| 1,3-dithiolan-2-yl | CH₃ | H | O | A-2 | CH₃ | O | — | |
| 1,3-dithiolan-2-yl | CH₃ | H | O | A-2 | OCH₃ | CH₂ | — | |
| 1,3-dioxolan-2-yl | CH₃ | H | O | A-3 | CH₃ | — | — | |
| 1,3-dioxolan-2-yl | CH₃ | H | O | A-3 | OCH₃ | — | — | |
| 1,3-dioxolan-2-yl | CH₃ | H | O | A-4 | CH₃ | — | CH₃ | |
| 1,3-dioxolan-2-yl | CH₃ | H | O | A-4 | OCH₃ | — | H | |
| 1,3-dioxolan-2-yl | CH₃ | H | O | A-4 | OCF₂H | CH₃ | | |
| C(OCH₃)₃ | CH₃ | H | O | A-2 | CH₃ | O | — | |
| C(OCH₃)₃ | CH₃ | H | O | A-3 | CH₃ | — | — | |
| C(OCH₃)₃ | CH₃ | H | O | A-4 | CH₃ | — | CH₃ | |

| | | | | | X₂ | Y₃ | | |
|---|---|---|---|---|---|---|---|---|
| C(OCH₃)₃ | CH₃ | H | O | A-5 | CH₃ | OCH₃ | | |
| 1,3-dioxolan-2-yl | CH₃ | H | O | A-5 | CH₃ | SCH₃ | | |

| | | | | | X₃ | | | |
|---|---|---|---|---|---|---|---|---|
| C(CH₃)(OCH₃)₂ | CH₃ | H | O | A-6 | CH₃ | — | — | |
| C(OCH₃)₃ | CH₃ | H | O | A-6 | OCH₃ | — | — | |

| | | | | | X₄ | Y₄ | Z | |
|---|---|---|---|---|---|---|---|---|
| 1,3-dioxolan-2-yl | CH₃ | H | O | A-7 | CH₃ | CH₃ | CH | |
| C(OCH₃)₃ | CH₃ | H | O | A-7 | OCH₃ | OCH₃ | CH | |

TABLE Vc

General Structure Vc

| R₁ | R₁₁ | R | W | A | X₁ | Y₁ | Y₂ | m.p. °C |
|---|---|---|---|---|---|---|---|---|
| 1,3-dioxolan-2-yl | CH₃ | H | O | A-2 | CH₃ | O | — | |
| 1,3-dioxolan-2-yl | CH₃ | H | O | A-2 | OCF₂H | O | — | |
| 1,3-dioxolan-2-yl | CH₃ | H | O | A-2 | OCH₃ | O | — | |
| 1,3-dioxolan-2-yl | CH₃ | H | O | A-2 | CH₃ | CH₂ | — | |
| 1,3-dioxolan-2-yl | CH₃ | H | O | A-2 | OCH₃ | CH₂ | — | |
| 1,3-dioxolan-2-yl | CH₃ | H | O | A-2 | OC₂H₅ | CH₂ | — | |
| 1,3-dithiolan-2-yl | CH₃ | H | O | A-2 | CH₃ | O | — | |
| 1,3-dithiolan-2-yl | CH₃ | H | O | A-2 | OCH₃ | CH₂ | — | |
| 1,3-dioxolan-2-yl | CH₃ | H | O | A-3 | CH₃ | — | — | |
| 1,3-dioxolan-2-yl | CH₃ | H | O | A-3 | OCH₃ | — | — | |
| 1,3-dioxolan-2-yl | CH₃ | H | O | A-4 | CH₃ | — | CH₃ | |
| 1,3-dioxolan-2-yl | CH₃ | H | O | A-4 | OCH₃ | — | H | |
| 1,3-dioxolan-2-yl | CH₃ | H | O | A-4 | OCF₂H | — | CH₃ | |
| C(OCH₃)₃ | CH₃ | H | O | A-2 | CH₃ | O | — | |
| C(OCH₃)₃ | CH₃ | H | O | A-3 | CH₃ | — | — | |
| C(OCH₃)₃ | CH₃ | H | O | A-4 | CH₃ | — | CH₃ | |

TABLE Vc-continued

General Structure Vc

| R₁ | R | W | A | X₂ | Y₃ | | |
|---|---|---|---|---|---|---|---|
| C(OCH₃)₃ | CH₃ | H | O | A-5 | CH₃ | OCH₃ | |
| 1,3-dioxolan-2-yl | CH₃ | H | O | A-5 | CH₃ | SCH₃ | |

| R₁ | R | W | A | X₃ | | | |
|---|---|---|---|---|---|---|---|
| C(CH₃)(OCH₃)₂ | CH₃ | H | O | A-6 | CH₃ | — | — |
| C(OCH₃)₃ | CH₃ | H | O | A-6 | OCH₃ | — | — |

| R₁ | R | W | A | X₄ | Y₄ | Z | |
|---|---|---|---|---|---|---|---|
| 1,3-dioxolan-2-yl | CH₃ | H | O | A-7 | CH₃ | CH₃ | CH |
| C(OCH₃)₃ | CH₃ | H | O | A-7 | OCH₃ | OCH₃ | CH |

TABLE VI

General Structure VI

| R₁ | R | W | A | X₁ | Y₁ | Y₂ | m.p. °C. |
|---|---|---|---|---|---|---|---|
| 1,3-dioxolan-2-yl | H | O | A-2 | CH₃ | O | — | |
| 1,3-dioxolan-2-yl | H | O | A-2 | OCF₂H | O | — | |
| 1,3-dioxolan-2-yl | H | O | A-2 | OCH₃ | O | — | |
| 1,3-dioxolan-2-yl | H | O | A-2 | CH₃ | CH₂ | — | |
| 1,3-dioxolan-2-yl | H | O | A-2 | OCH₃ | CH₂ | — | |
| 1,3-dioxolan-2-yl | H | O | A-2 | OC₂H₅ | CH₂ | — | |
| 1,3-dithiolan-2-yl | H | O | A-2 | CH₃ | O | — | |
| 1,3-dithiolan-2-yl | H | O | A-2 | OCH₃ | CH₂ | — | |
| 1,3-dioxolan-2-yl | H | O | A-3 | CH₃ | — | — | |
| 1,3-dioxolan-2-yl | H | O | A-3 | OCH₃ | — | — | |
| 1,3-dioxolan-2-yl | H | O | A-4 | CH₃ | — | CH₃ | |
| 1,3-dioxolan-2-yl | H | O | A-4 | OCH₃ | — | H | |
| 1,3-dioxolan-2-yl | H | O | A-4 | OCF₂H | — | CH₃ | |
| C(OCH₃)₃ | CH₃ | O | A-2 | CH | O₃ | — | |
| C(OCH₃)₃ | CH₃ | O | A-3 | CH₃ | — | — | |
| C(OCH₃)₃ | CH₃ | O | A-4 | CH₃ | — | CH₃ | |

| R₁ | R | W | A | X₂ | Y₃ | | |
|---|---|---|---|---|---|---|---|
| C(OCH₃)₃ | CH₃ | O | A-5 | CH₃ | OCH₃ | | |
| 1,3-dioxolan-2-yl | CH₃ | O | A-5 | CH₃ | SCH₃ | | |

| R₁ | R | W | A | X₃ | | | |
|---|---|---|---|---|---|---|---|
| C(CH₃)(OCH₃)₂ | CH₃ | O | A-6 | CH₃ | — | — | |
| C(OCH₃)₃ | CH₃ | O | A-6 | OCH—₃ | — | | |

| R₁ | R | W | A | X₄ | Y₄ | Z | |
|---|---|---|---|---|---|---|---|
| 1,3-dioxolan-2-yl | CH₃ | O | A-7 | CH | CH₃ | CH₃ | |
| C(OCH₃)₃ | CH₃ | O | A-7 | OCH | OCH₃ | CH₃ | |

TABLE VIa

General Structure VIa

| R₁ | R | W | A | X₁ | Y₁ | Y₂ | m.p. °C. |
|---|---|---|---|---|---|---|---|
| 1,3-dioxolan-2-yl | H | O | A-2 | CH₂ | O | — | |
| 1,3-dioxolan-2-yl | H | O | A-2 | OCF₂H | O | — | |
| 1,3-dioxolan-2-yl | H | O | A-2 | OCH₃ | O | — | |
| 1,3-dioxolan-2-yl | H | O | A-2 | CH₃ | CH₂ | — | |
| 1,3-dioxolan-2-yl | H | O | A-2 | OCH₃ | CH₂ | — | |
| 1,3-dioxolan-2-yl | H | 0 | 2 | OC₂H₅ | CH₂ | — | |
| 1,3-dithiolan-2-yl | H | O | A-2 | CH₃ | O | — | |
| 1,3-dithiolan-2-yl | H | O | A-2 | OCH₃ | CH₂ | — | |
| 1,3-dioxolan-2-yl | H | O | A-3 | CH₃ | — | — | |
| 1,3-dioxolan-2-yl | H | O | A-3 | OCH₃ | — | — | |
| 1,3-dioxolan-2-yl | H | O | A-4 | CH₃ | — | CH₃ | |
| 1,3-dioxolan-2-yl | H | O | A-4 | OCH₃ | — | H | |
| 1,3-dioxolan-2-yl | H | O | A-4 | OCF₂H | — | CH₃ | |
| C(OCH₃)₃ | CH₃ | O | A-2 | CH₃ | O | — | |
| C(OCH₃)₃ | CH₃ | O | A-3 | CH₃ | — | — | |
| C(OCH₃)₃ | CH₃ | O | A-4 | CH₃ | — | CH₃ | |

| R₁ | R | W | A | X₂ | Y₃ | | |
|---|---|---|---|---|---|---|---|
| C(OCH₃)₃ | CH₃ | O | A-5 | CH₃ | OCH₃ | | |
| 1,3-dioxolan-2-yl | CH₃ | O | A-5 | CH₃ | SCH₃ | | |

| X₃ |
|---|

TABLE VIa-continued

General Structure VIa

| | | | | | | |
|---|---|---|---|---|---|---|
| C(CH$_3$)(OCH$_3$)$_2$ | CH$_3$ | O | A-6 | CH$_3$ | — | — |
| C(OCH$_3$)$_3$ | CH$_3$ | O | A-6 | OCH$_3$ | — | — |

| | | | | X$_4$ | Y$_4$ | Z |
|---|---|---|---|---|---|---|
| 1,3-dioxolan-2-yl | CH$_3$ | O | A-7 | CH$_3$ | CH$_3$ | CH |
| C(OCH$_3$)$_3$ | CH$_3$ | O | A-7 | OCH$_3$ | OCH$_3$ | CH |

TABLE VIb

General Structure VIb

| R$_1$ | R | W | A | X$_1$ | Y$_1$ | Y$_2$ | m.p. °C. |
|---|---|---|---|---|---|---|---|
| 1,3-dioxolan-2-yl | H | O | A-2 | CH$_3$ | O | — | |
| 1,3-dioxolan-2-yl | H | O | A-2 | OCF$_2$H | O | — | |
| 1,3-dioxolan-2-yl | H | O | A-2 | OCH$_3$ | O | — | |
| 1,3-dioxolan-2-yl | H | O | A-2 | CH$_3$ | CH$_2$ | — | |
| 1,3-dioxolan-2-yl | H | O | A-2 | OCH$_3$ | CH$_2$ | — | |
| 1,3-dioxolan-2-yl | H | O | A-2 | OC$_2$H$_5$ | CH$_2$ | — | |
| 1,3-dithiolan-2-yl | H | O | A-2 | CH$_3$ | O | — | |
| 1,3-dithiolan-2-yl | H | O | A-2 | OCH$_3$ | CH$_2$ | — | |
| 1,3-dioxolan-2-yl | H | O | A-3 | CH$_3$ | — | — | |
| 1,3-dioxolan-2-yl | H | O | A-3 | OCH$_3$ | — | — | |
| 1,3-dioxolan-2-yl | H | O | A-4 | CH$_3$ | — | CH$_3$ | |
| 1,3-dioxolan-2-yl | H | O | A-4 | OCH$_3$ | — | H | |
| 1,3-dioxolan-2-yl | H | O | A-4 | OCF$_2$H | — | CH$_3$ | |
| C(OCH$_3$)$_3$ | CH$_3$ | O | A-2 | CH$_3$ | O | — | |
| C(OCH$_3$)$_3$ | CH$_3$ | O | A-2 | CH$_3$ | O | — | |
| C(OCH$_3$)$_3$ | CH$_3$ | O | A-3 | CH$_3$ | — | — | |
| C(OCH$_3$)$_3$ | CH$_3$ | O | A-4 | CH$_3$ | — | CH$_3$ | |

| | | | | X$_2$ | Y$_3$ | | |
|---|---|---|---|---|---|---|---|
| C(OCH$_3$)$_3$ | CH$_3$ | O | A-5 | CH$_3$ | OCH$_3$ | | |
| 1,3-dioxolan-2-yl | CH$_3$ | O | A-5 | CH$_3$ | SCH$_3$ | | |

| | | | | X$_3$ | | | |
|---|---|---|---|---|---|---|---|
| C(CH$_3$)(OCH$_3$)$_2$ | CH$_3$ | O | A-6 | CH$_3$ | — | — | |
| C(OCH$_3$)$_3$ | CH$_3$ | O | A-6 | OCH$_3$ | — | — | |

| | | | | X$_4$ | Y$_4$ | Z | |
|---|---|---|---|---|---|---|---|
| 1,3-dioxolan-2-yl | CH$_3$ | O | A-7 | CH$_3$ | CH$_3$ | CH | |
| C(OCH$_3$)$_3$ | CH$_3$ | O | A-7 | OCH$_3$ | OCH$_3$ | CH | |

TABLE VII

General Structure VII

| R$_1$ | R | R$_{14}$ | E | W | X | Y | Z | m.p. °C. |
|---|---|---|---|---|---|---|---|---|
| C(OCH$_3$)$_3$ | H | H | — | O | CH$_3$ | CH$_3$ | CH | |
| C(OCH$_3$)$_3$ | H | H | — | O | CH$_3$ | OCH$_3$ | CH | |
| C(OCH$_3$)$_3$ | H | H | — | O | OCH$_3$ | OCH$_3$ | CH | |
| C(OCH$_3$)$_3$ | H | H | — | O | Cl | OCH$_3$ | CH | |
| C(OCH$_3$)$_3$ | H | H | — | O | Br | OCH$_3$ | CH | |
| C(OCH$_3$)$_3$ | H | H | — | O | CH$_3$ | H | CH | |
| C(OCH$_3$)$_3$ | H | H | — | O | OCH$_3$ | H | CH | |
| C(OCH$_3$)$_3$ | H | H | — | O | OCH$_3$ | CH$_2$OC$_2$H$_5$ | CH | |
| C(OCH$_3$)$_3$ | H | H | — | O | OCF$_2$H | OCH$_3$ | CH | |
| C(OCH$_3$)$_3$ | H | H | — | O | OCH$_3$ | CH(OCH$_3$)$_2$ | CH | |
| C(OCH$_3$)$_3$ | H | H | — | O | CH$_3$ | OC$_2$H$_5$ | CH | |
| C(OCH$_3$)$_3$ | H | H | — | O | CH$_3$ | CH$_2$OCH$_3$ | CH | |
| C(OCH$_3$)$_3$ | H | H | — | O | OCH$_3$ | CH$_2$OCH$_3$ | CH | |
| C(OCH$_3$)$_3$ | H | H | — | O | OCH$_3$ | C$_2$H$_5$ | CH | |
| C(OCH$_3$)$_3$ | H | H | — | O | OC$_2$H$_5$ | OCH$_3$ | CH | |
| C(OCH$_3$)$_3$ | H | H | — | O | OCF$_2$H | OCF$_2$H | CH | |
| C(OCH$_3$)$_3$ | H | H | — | O | CH$_2$F | OCH$_3$ | CH | |
| C(OCH$_3$)$_3$ | H | H | — | O | CH$_2$Cl | OCH$_3$ | CH | |
| C(OCH$_3$)$_3$ | H | H | — | O | CF$_3$ | OCH$_3$ | CH | |
| C(OCH$_3$)$_3$ | H | H | — | O | Cl | OC$_2$H$_5$ | CH | |
| C(OCH$_3$)$_3$ | H | H | — | O | OCH$_2$CH$_2$F | OCH$_3$ | CH | |
| C(OCH$_3$)$_3$ | H | H | — | O | OCH$_2$CF$_3$ | OCH$_3$ | CH | |
| C(OCH$_3$)$_3$ | H | H | — | O | CH$_3$ | OCH$_3$ | N | |
| C(OCH$_3$)$_3$ | H | H | — | O | OCH$_3$ | OCH$_3$ | N | |
| C(OCH$_3$)$_3$ | H | H | — | O | CH$_3$ | CH$_3$ | N | |
| C(OCH$_3$)$_3$ | H | H | — | O | OCH$_3$ | cyclopropyl | N | |
| C(OCH$_3$)$_3$ | H | H | — | O | OC$_2$H$_5$ | NHCH$_3$ | N | |
| C(OCH$_3$)$_3$ | H | H | — | O | OCH$_2$CF$_3$ | OCH$_3$ | N | |

TABLE VII-continued

General Structure VII

| R$_1$ | R | R$_{14}$ | E | W | X | Y | Z | m.p. °C. |
|---|---|---|---|---|---|---|---|---|
| C(OCH$_3$)$_3$ | H | H | — | O | OCH$_2$CH$_2$F | CH$_3$ | N | |
| C(OCH$_3$)$_3$ | H | H | — | O | OCH$_2$CH$_2$F | OCH$_3$ | N | |
| C(OCH$_3$)$_3$ | H | H | — | S | OCH$_3$ | OCH$_3$ | CH | |
| C(OCH$_3$)$_3$ | H | 3-F | — | O | OCH$_3$ | OCH$_3$ | CH | |
| C(OCH$_3$)$_3$ | H | 5-Cl | — | O | OCH$_3$ | OCH$_3$ | CH | |
| C(OCH$_3$)$_3$ | H | 5-CH$_3$ | — | O | OCH$_3$ | OCH$_3$ | CH | |
| C(OCH$_3$)$_3$ | H | 5-C$_2$H$_5$ | — | O | OCH$_3$ | OCH$_3$ | CH | |
| C(OCH$_3$)$_3$ | H | 6-OCH$_3$ | — | O | OCH$_3$ | OCH$_3$ | CH | |
| C(OCH$_3$)$_3$ | H | 6-OC$_2$H$_5$ | — | O | OCH$_3$ | OCH$_3$ | CH | |
| C(OCH$_3$)$_3$ | H | 6-SCH$_3$ | — | O | OCH$_3$ | OCH$_3$ | CH | |
| C(OCH$_3$)$_3$ | H | 6-SC$_2$H$_5$ | — | O | OCH$_3$ | OCH$_3$ | CH | |
| C(OCH$_3$)$_3$ | H | 5-Br | — | O | OCH$_3$ | OCH$_3$ | CH | |
| C(OCH$_3$)$_3$ | H | H | CH$_2$ | O | OCH$_3$ | OCH$_3$ | CH | |
| C(OC$_2$H$_5$)$_3$ | H | H | CH$_2$ | O | CH$_3$ | CH$_3$ | CH | |
| C(OC$_2$H$_5$)$_3$ | H | H | CH$_2$ | O | CH$_3$ | OCH$_3$ | CH | |
| C(OC$_2$H$_5$)$_3$ | H | H | CH$_2$ | O | OCH$_3$ | OCH$_3$ | CH | |
| C(OC$_2$H$_5$)$_3$ | H | H | CH$_2$ | O | Cl | OCH$_3$ | CH | |
| C(OC$_2$H$_5$)$_3$ | H | H | CH$_2$ | O | CH$_3$ | OCH$_3$ | N | |
| C(OC$_2$H$_5$)$_3$ | H | H | CH$_2$ | O | OCH$_3$ | OCH$_3$ | N | |
| C(OCH$_2$CH$_2$CH$_3$)$_3$ | H | H | CH$_2$ | O | OCH$_3$ | OCH$_3$ | CH | |
| C(OCH$_2$CH$_2$CH$_3$)$_3$ | H | H | CH$_2$ | O | CH$_3$ | OCH$_3$ | CH | |
| C(OCH$_2$CH$_2$CH$_3$)$_3$ | H | H | CH$_2$ | O | CH$_3$ | CH$_3$ | CH | |
| C(OCH$_2$CH$_2$CH$_3$)$_3$ | H | H | CH$_2$ | O | Cl | OCH$_3$ | CH | |
| C(OCH$_2$CH$_2$CH$_3$)$_3$ | H | H | CH$_2$ | O | CH$_3$ | OCH$_3$ | N | |
| C(OCH$_2$CH$_2$CH$_3$)$_3$ | H | H | CH$_2$ | O | OCH$_3$ | OCH$_3$ | N | |
| C(OCH$_3$)$_3$ | CH$_3$ | H | CH$_2$ | O | OCH$_3$ | OCH$_3$ | CH | |
| C(OCH$_3$)$_3$ | H | H | CH$_2$ | O | OCH$_2$CHF$_2$ | CH$_3$ | N | |
| C(OCH$_3$)$_3$ | H | H | CH$_2$ | O | CH$_3$ | i-C$_3$H$_7$ | CH | |
| C(OCH$_3$)$_3$ | H | H | — | O | OCH$_3$ | N(OCH$_3$)CH$_3$ | N | |
| C(OCH$_3$)$_3$ | H | H | — | O | CH$_3$ | N(CH$_2$)$_3$ | N | |
| C(OCH$_3$)$_3$ | H | H | — | O | OCH$_3$ | CF$_3$ | CH | |
| C(OCH$_3$)$_3$ | H | H | — | O | CH$_3$ | SCH$_3$ | N | |
| C(OCH$_3$)$_3$ | H | H | — | O | CH$_3$ | OCH$_2$CH=CH$_2$ | N | |
| C(OCH$_3$)$_3$ | H | H | — | O | CH$_3$ | OCH$_2$CH≡CH | N | |
| C(OCH$_3$)$_3$ | H | H | — | O | CH$_3$ | CH$_2$SCH$_3$ | N | |
| C(OCH$_3$)$_3$ | H | H | — | O | OCH$_3$ | SCF$_2$H | CH | |
| C(OCH$_3$)$_3$ | H | H | — | O | OCH$_3$ | 1,3-dioxolan-2-yl | CH | |
| C(OCH$_3$)$_3$ | H | H | — | O | OCH$_3$ | 4-methyl-1,3-dioxolan-2-yl | N | |
| C(OCH$_3$)$_3$ | H | H | — | O | OCH$_3$ | 4-ethyl-1,3-dioxolan-2-yl | CH | |
| C(OCH$_3$)$_3$ | H | H | — | O | OCH$_3$ | 1,3-dithiolan-2-yl | CH | |
| C(OCH$_3$)$_3$ | H | H | — | O | OCH$_3$ | 1,3-oxathiolan-2-yl | N | |
| C(OCH$_3$)(OC$_2$H$_5$)$_2$ | H | H | — | O | OCH$_3$ | OCH$_3$ | CH | |
| C(OC$_2$H$_5$)(OCH$_3$)$_2$ | H | H | — | O | OCH$_3$ | OCH$_3$ | CH | |
| 2-methoxy-1,3-dioxolan-2-yl | H | H | — | O | OCH$_3$ | OCH$_3$ | CH | |
| 2-ethoxy-1,3-dioxolan-2-yl | H | H | — | O | OCH$_3$ | OCH$_3$ | CH | |

TABLE VIIa

General Structure VIIa

| R$_1$ | R | R$_{14}$ | E | W | A | X$_1$ | Y$_1$ | Y$_2$ | m.p. °C. |
|---|---|---|---|---|---|---|---|---|---|
| C(OCH$_3$)$_3$ | H | H | — | O | A-2 | CH$_3$ | O | — | |
| C(OCH$_3$)$_3$ | H | H | — | O | A-2 | OCH$_3$ | O | — | |
| C(OCH$_3$)$_3$ | H | H | — | O | A-2 | OCH$_3$ | CH$_2$ | — | |
| C(OCH$_3$)$_3$ | H | H | — | O | A-2 | OCF$_2$H | O | — | |
| C(OC$_2$H$_5$)$_3$ | H | H | — | O | A-2 | CH$_3$ | O | — | |
| C(OC$_2$H$_5$)$_3$ | H | H | — | O | A-2 | OCH$_3$ | O | — | |
| C(OCH$_2$CH$_2$CH$_3$)$_3$ | H | H | — | O | A-2 | CH$_3$ | O | — | |
| C(OCH$_2$CH$_2$CH$_3$)$_3$ | H | H | — | O | A-2 | OCH$_3$ | O | — | |
| C(OCH$_3$)$_3$ | H | H | — | O | A-3 | CH$_3$ | — | — | |
| C(OCH$_3$)$_3$ | H | H | — | O | A-3 | OCH$_3$ | — | — | |
| C(OCH$_3$)$_3$ | H | H | — | O | A-4 | CH$_3$ | — | CH$_3$ | |
| C(OCH$_3$)$_3$ | H | H | — | O | A-4 | OCH$_3$ | — | CH$_3$ | |
| C(OCH$_3$)$_3$ | H | H | — | O | A-4 | OCH$_3$ | — | H | |

| R$_1$ | R | R$_{14}$ | E | W | A | X$_2$ | Y$_3$ | | |
|---|---|---|---|---|---|---|---|---|---|
| C(OCH$_3$)$_3$ | H | H | — | O | A-5 | CH$_3$ | OCH$_3$ | | |
| C(OCH$_3$)$_3$ | H | H | — | O | A-5 | CH$_3$ | SCH$_3$ | | |
| C(OCH$_3$)$_3$ | H | H | — | O | A-5 | CH$_3$ | CH$_3$ | | |

| R$_1$ | R | R$_{14}$ | E | W | A | X$_3$ | | | |
|---|---|---|---|---|---|---|---|---|---|
| C(OCH$_3$)$_3$ | H | H | — | O | A-6 | CH$_3$ | | | |
| C(OCH$_3$)$_3$ | H | H | — | O | A-6 | OCH$_3$ | | | |

| R$_1$ | R | R$_{14}$ | E | W | A | X$_4$ | Y$_4$ | Z | |
|---|---|---|---|---|---|---|---|---|---|
| C(OCH$_3$)$_3$ | H | H | — | O | A-7 | CH$_3$ | CH$_3$ | CH | |
| C(OCH$_3$)$_3$ | H | H | — | O | A-7 | OCH$_3$ | OCH$_3$ | CH | |

TABLE VIIa-continued

| | | | General Structure VIIa | | | | | | |
|---|---|---|---|---|---|---|---|---|---|
| R₁ | R | R₁₄ | E | W | A | X₁ | Y₁ | Y₂ | m.p. °C. |
| C(OCH₃)₃ | H | H | — | O | A-7 | OCH₃ | OCH₃ | N | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions:

| | Active Ingredient | Weight Percent* | |
|---|---|---|---|
| | | Diluent(s) | Surfactant(s) |
| Wettable Powders | 20–90 | 0–74 | 1–10 |
| Oil Suspensions, Emulsions, Solutions, (including Emulsifiable Concentrates) | 5–50 | 40–95 | 0–15 |
| Aqueous Suspension | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powder and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preferred granular carriers or by agglomeration techniques.

In the following examples, all parts are by weight unless otherwise indicated.

EXAMPLE 5

Wettable Powder

| | |
|---|---|
| 3-(1,3-dioxolan-2-yl)-N—[(4-methoxy-6-methyl-1,3,5-triazin-2-yl)aminocarbonyl]-2-thiophenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 6

Wettable Powder

| | |
|---|---|
| N—[(4,6-dimethoxypyrimidin-2-yl)aminocarbonyl]-3-(1,3-dioxolan-2-yl)-2-thiophenesulfonamide | 50% |
| sodium alkylnaphthalenesulfonate | 2% |
| low viscosity methyl cellulose | 2% |
| diatomaceous earth | 36% |

The ingredients are blended, coarsely hammer-milled and then air-milled to produce particles essentially all below 10 microns in diameter. The product is reblended before packaging.

EXAMPLE 7

High Strength Concentrate

| | |
|---|---|
| 3-(1,3-dioxolan-2-yl)-N—[(4-methoxy-6-methyl-1,3,5-triazin-2-yl)aminocarbonyl]-2-thiophenesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 8

Wettable Powder

| | |
|---|---|
| 3-(1,3-dioxolan-2-yl)-N—[(4-methoxy-6-methyl-1,3,5-triazin-2-yl)aminocarbonyl]-2-thiophenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 9

Oil Suspension

| | |
|---|---|
| N—[(4,6-dimethoxypyrimidin-2-yl)aminocarbonyl]-3-(1,3-dioxolan-2-yl)-2-thiophenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 10

Oil Suspension

| | |
|---|---|
| 3-(1,3-dioxolan-2-yl)-N—[(4-methoxy-6-methyl-1,3,5-triazin-2-yl)aminocarbonyl]-2-thiophenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 11

Aqueous Suspension

| | |
|---|---|
| 3-(1,3-dioxolan-2-yl)-N—[(4-methoxy-6-methyl-1,3,5-triazin-2-yl)aminocarbonyl]-2-thiophenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 12

Solution

| | |
|---|---|
| 3-(1,3-dioxolan-2-yl)-N—[(4-methoxy-6-methyl-1,3,5-triazin-2-yl)aminocarbonyl]-2-thiophenesulfonamide | 30% |
| dimethylformamide | 70% |

The ingredients are combined and stirred to produce a solution, which can be used for low volume applications.

EXAMPLE 13

Dust

| | |
|---|---|
| wettable powder of Example 6 | 10% |
| Pyrophyllite (powder) | 90% |

The wettable powder and the pyrophyllite diluent are thoroughly blended and then packaged. The product is suitable for use a a dust.

EXAMPLE 14

Low Strength Granule

| | |
|---|---|
| 3-(1,3-dioxolan-2-yl)-N—[(4-methoxy-6-methyl-1,3,5-triazin-2-yl)aminocarbonyl]-2-thiophenesulfonamide | 0.1% |
| attapulgite granules (U.S.S. 20–40 mesh) | 99.9% |

The active ingredient is dissolved in the solvent and the solution is sprayed upon dedusted granules in a double cone blender. After spraying of the solution has been completed, the material is warmed to evaporate the solvent. The material is allowed to cool and then packaged.

EXAMPLE 15

Granule

| | |
|---|---|
| Wettable Powder of Example 6 | 5% |
| attapulgite granules (U.S.S. 20–40 mesh: 0.84–0.42 mm) | 95% |

A slurry of wettable powder containing 25% solids is sprayed on the surface of attapulgite granules in a double-cone blender. The granules are dried and packaged.

EXAMPLE 16

Granule

| | |
|---|---|
| N—[](4,6-dimethoxypyrimidin-2-yl)aminocarbonyl]-3-(1,3-dioxolan-2-yl)-2-thiophenesulfonamide | 80% |
| wetting agent | 1% |
| crude ligninsulfonate salt (containing 5–20 of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 17

Extruded Pellet

| | |
|---|---|
| 3-(1,3-dioxolan-2-yl)-N—[(4-methoxy-6-methyl- | |

-continued

| | |
|---|---|
| 1,3,5-triazin-2-yl)aminocarbonyl]-2-thiophene-sulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

Utility

Test results indicate that the compounds of the present invention are active herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.01 to 5.0 kg/ha, the lower rates being suggested for use on lighter soils and/or those having a low organic matter content, for plant growth modification or for situations where only short-term persistence is required.

The compounds of the invention may be used in combination with any other commercial herbicide; examples of which are those of the triazine, triazole, uracil, urea, amide, diphenylether, carbamate and bipyridylium types.

The herbicidal properties of the subject compounds were discovered in a number of greenhouse tests. The test procedures and results follow.

COMPOUNDS

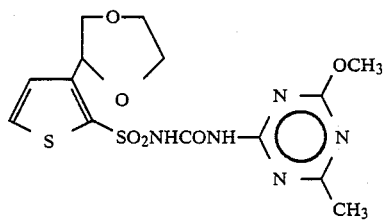

Compound 1

-continued
COMPOUNDS

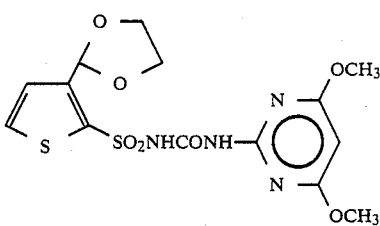

Compound 2

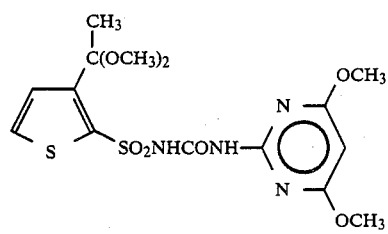

Compound 3

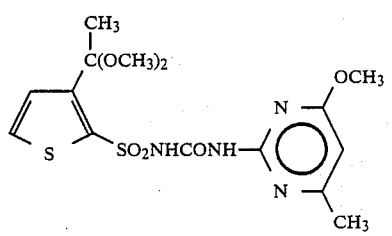

Compound 4

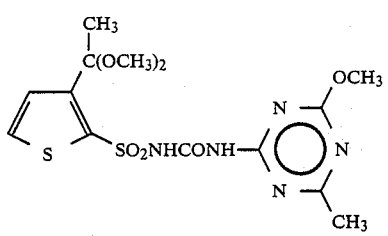

Compound 5

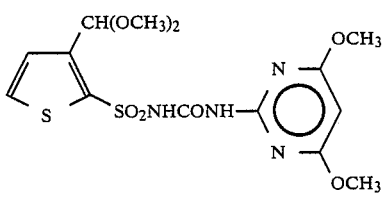

Compound 6

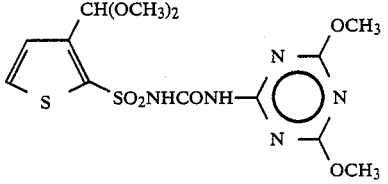

Compound 7

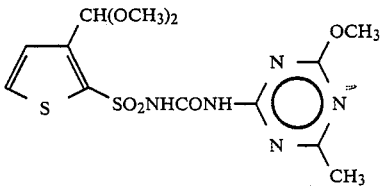

Compound 8

-continued
COMPOUNDS

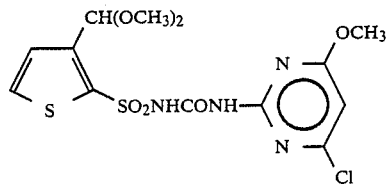

Compound 9

Test A

Seeds of crabgrass (Digitaria sp.), barnyardgrass (Echinochloa crusgalli), wild oats (Avena fatua), sicklepod (Cassia obtusifolia), morningglory (Ipomoea spp.), cocklebur (Xanthium pensylvanicum), sorghum, corn, soybean, sugar beet, cotton, rice, wheat and purple nutsedge (Cyperus rotundus) tubers were planted and treated pre-emergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis or necrosis;
B=burn
D=defoliation
E=emergence inhibition;
G=growth retardation; and
H=formative effects.
U=unusual pigmentation
X=axillary stimulation
S=albinism
6Y=abscised buds or flowers.

TABLE A

| Rate kg/ha | Compound 1<br>0.05 | Compound 2<br>0.05 |
|---|---|---|
| POST-EMERGENCE | | |
| Morningglory | 9C | 10C |
| Cocklebur | 9C | 10C |
| Sicklepod | 2C,5G | 7G |
| Nutsedge | 4G | 10C |
| Crabgrass | 3C,8G | 5C,9G |
| Barnyardgrass | 5C,9H | 9C |
| Wild Oats | 8G | 5C,9G |
| Wheat | 5G | 6C,9G |
| Corn | 2C,9G | 3C,9G |
| Soybean | 9C | 9C |
| Rice | 9C | 9C |
| Sorghum | 9G | 5C,9G |
| Sugar beet | 10C | 9C |
| Cotton | 9C | 9C |
| PRE-EMERGENCE | | |
| Morningglory | 9G | 4C,9G |
| Cocklebur | 8H | 9H |
| Sicklepod | 9G | 9G |
| Nutsedge | 0 | 10E |
| Crabgrass | 2C,5G | 7G |
| Barnyardgrass | 3C,7H | 9H |
| Wild Oats | 6C,9G | 5C,9G |
| Wheat | 5G | 4C,9G |
| Corn | 5C,9H | 9G |
| Soybean | 9H | 9H |
| Rice | 10E | 10E |
| Sorghum | 5C,9H | 6C,9H |

TABLE A-continued

| | | |
|---|---|---|
| Sugar beet | 5C,9G | 9C |
| Cotton | 2C,9G | 9G |

| Rate kg/ha | Compound 3<br>0.05 | Compound 4<br>0.05 |
|---|---|---|
| POST-EMERGENCE | | |
| Morningglory | 10C | 10C |
| Cocklebur | 4C,9H | 9C |
| Velvetleaf | 9C | 9C |
| Nutsedge | 9C | 8C |
| Crabgrass | 7H | 7G |
| Barnyardgrass | 9C | 9C |
| Cheatgrass | 10C | 6C,9G |
| Wild Oats | 2C,5G | 2G |
| Wheat | 2G | 2G |
| Corn | 7U,9C | 10C |
| Soybean | 9C | 9C |
| Rice | 9C | 9C |
| Sorghum | 5C,9H | 2U,8H |
| Sugar beet | 9C | 9C |
| Cotton | 9C | 9C |
| PRE-EMERGENCE | | |
| Morningglory | 9C | 9G |
| Cocklebur | 7H | 8H |
| Velvetleaf | 10C | 9C |
| Nutsedge | 10E | 10E |
| Crabgrass | 2C,7G | 4C,9G |
| Barnyardgrass | 9H | 9H |
| Cheatgrass | 4C,9H | 3C,9H |
| Wild Oats | 8G | 8G |
| Wheat | 2C,8H | 8G |
| Corn | 9H | 4C,9H |
| Soybean | 8H | 9H |
| Rice | 10E | 10E |
| Sorghum | 9H | 3C,9H |
| Sugar beet | 5C,9G | 5C,9G |
| Cotton | 9G | 9G |

| Rate kg/ha | Compound 5<br>0.05 | Compound 6<br>0.05 |
|---|---|---|
| POST-EMERGENCE | | |
| Morningglory | 10C | 10C |
| Cocklebur | 9H | 9C |
| Velvetleaf | 2C,7G | 9C |
| Nutsedge | 4G | 9C |
| Crabgrass | 2G | 2C,6G |
| Barnyardgrass | 9C | 3C,9H |
| Cheatgrass | 0 | 3C,8G |
| Wild Oats | 0 | 0 |
| Wheat | 0 | 0 |
| Corn | 7U,9C | 2C,8H |
| Soybean | 5C,9G | 5C,9G |
| Rice | 4C,8G | 4C,9G |
| Sorghum | 3C,9H | 4C,9H |
| Sugar beet | 9C | 9C |
| Cotton | 5C,9G | 9C |
| PRE-EMERGENCE | | |
| Morningglory | 9G | 9H |
| Cocklebur | 3H | 8H |
| Velvetleaf | 5G | 9G |
| Nutsedge | 3G | 2C,9G |
| Crabgrass | 2G | 0 |
| Barnyardgrass | 3C,7G | 4C,9H |
| Cheatgrass | 6G | 3C,8G |
| Wild Oats | 3G | 5G |
| Wheat | 2G | 4G |
| Corn | 2C,9G | 8G |
| Soybean | 2C,5G | 9H |
| Rice | 3C,8H | 4C,9H |
| Sorghum | 3C,9H | 4C,8H |
| Sugar beet | 5C,9G | 9C |
| Cotton | 2C,8G | 9G |

| Rate kg/ha | Compound 7<br>0.05 | Compound 8<br>0.05 | Compound 9<br>0.05 |
|---|---|---|---|
| POST-EMERGENCE | | | |
| Morningglory | 6C,9G | 9C | 10C |
| Cocklebur | 9C | 10C | 9C |
| Velvetleaf | 6C,9G | 10C | 9C |
| Nutsedge | 6G | 3G | 4C,8G |

TABLE A-continued

| | | | |
|---|---|---|---|
| Crabgrass | 5G | 4G | 0 |
| Barnyardgrass | 4C,9H | 4C,9H | 8H |
| Cheatgrass | 0 | 2C,3H | 0 |
| Wild Oats | 0 | 0 | 0 |
| Wheat | 0 | 0 | 0 |
| Corn | 2C,9G | 5C,9G | 1H |
| Soybean | 5C,9G | 5C,9G | 3H,9G,7X |
| Rice | 7G | 5G | 6G |
| Sorghum | 3C,9H | 5C,9H | 9H |
| Sugar beet | 3C,9G | 9C | 9C |
| Cotton | 9C | 9C | 9C |
| PRE-EMERGENCE | | | |
| Morningglory | 8H | 8G | 8G |
| Cocklebur | 9H | 5G | 7G |
| Velvetleaf | 4C,8G | 3C,8G | 4G |
| Nutsedge | 0 | 3G | 3G |
| Crabgrass | 0 | 0 | 0 |
| Barnyardgrass | 0 | 3C,7H | 4G |
| Cheatgrass | 3G | 0 | 0 |
| Wild Oats | 0 | 0 | 0 |
| Wheat | 0 | 0 | 0 |
| Corn | 2C,8H | 3C,9H | 4G |
| Soybean | 3C,8H | 3C,8H | 5H |
| Rice | 3C,5H | 3C,7G | 0 |
| Sorghum | 3C,9H | 5C,9H | 2C,7G |
| Sugar beet | 5C,9G | 5C,9G | 7G |
| Cotton | 3C,8G | 8G | 8G |

What is claimed is:

1. A compound of the formula $$QSO_2NHCNA \quad \text{I}$$
$$\overset{\overset{W}{\|}}{} \quad \underset{R}{|}$$

wherein

Q is

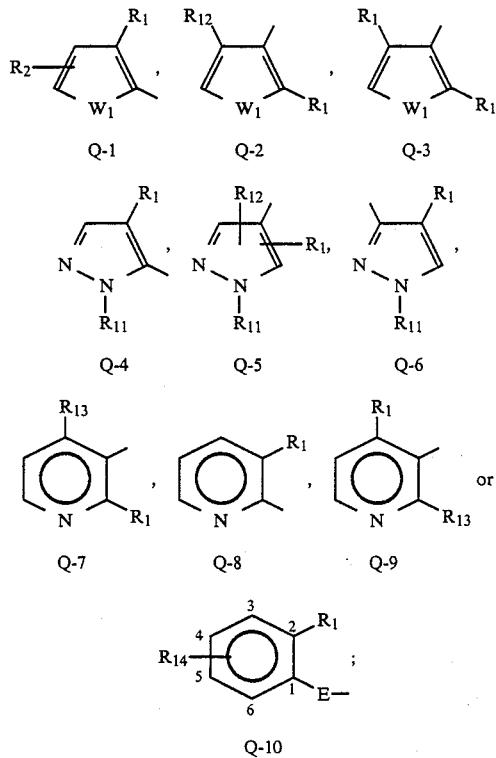

R is H or CH$_3$;

R$_1$ is

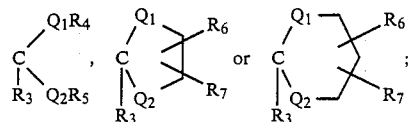

E is CH$_2$ or a single bond;
R$_2$ is H, C$_1$–C$_2$ alkyl or Cl;
R$_3$ is H, C$_1$–C$_3$ alkyl or C$_1$–C$_3$ alkoxy;
R$_4$ and R$_5$ are independently C$_1$–C$_2$ alkyl;
R$_6$ and R$_7$ are independently H or C$_1$–C$_2$ alkyl;
W is O or S;
W$_1$ is O or S;
Q$_1$ and Q$_2$ are independently O, S or NCH$_3$;

A is 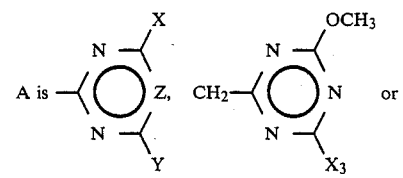

X is H, C$_1$–C$_4$ alkyl, C$_1$–C$_4$ alkoxy, C$_1$–C$_4$ haloalkoxy, C$_1$–C$_4$ haloalkyl, C$_1$–C$_4$ haloalkylthio, C$_1$–C$_4$ alkylthio, C$_2$–C$_5$ alkoxyalkoxy, amino, C$_1$–C$_3$ alkylamino or di(C$_1$–C$_3$)alkylamino;

Y is H, C$_1$–C$_4$ alkyl, C$_1$–C$_4$ alkoxy, C$_1$–C$_4$ haloalkoxy, C$_1$–C$_4$ haloalkylthio, C$_1$–C$_4$ alkylthio, C$_2$–C$_5$ alkoxyalkyl, C$_2$–C$_5$ alkoxyalkoxy, amino, C$_1$–C$_3$ alkylamino, di(C$_1$–C$_3$)alkylamino, C$_3$–C$_4$ alkenyloxy, C$_3$–C$_4$ alkynyloxy, C$_2$–C$_5$ alkylsulfinylalkyl, C$_1$–C$_4$ haloalkyl, C$_2$–C$_5$ alkylsulfonylalkyl, C$_3$–C$_5$ cycloalkyl, C$_2$–C$_4$ alkynyl, C$_2$–C$_5$ alkylthioalkyl, C(O)R$_8$,

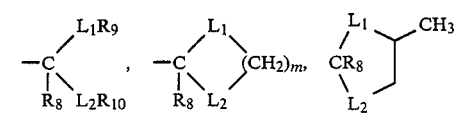

or N(OCH$_3$)CH$_3$;
m is 2 or 3;
L$_1$ and L$_2$ are independently O or S;
R$_8$ is H or CH$_3$;
R$_9$ and R$_{10}$ are independently C$_1$–C$_2$ alkyl;
R$_{11}$ is C$_1$–C$_3$ alkyl;
R$_{12}$ is H, F, Cl, NO$_2$, C$_1$–C$_2$ alkyl, C$_1$–C$_2$ alkoxy, C$_1$–C$_2$ alkylthio, C$_1$–C$_2$ alkylsulfinyl, C$_1$–C$_2$ alkylsulfonyl, di(C$_1$–C$_2$)alkylsulfamoyl or CO$_2$(C$_1$–C$_2$ alkyl);
R$_{13}$ is H, C$_1$–C$_2$ alkyl, C$_1$–C$_2$ alkoxy, Cl, F or NO$_2$;
R$_{14}$ is H, C$_1$–C$_3$ alkyl, C$_1$–C$_3$ alkoxy, C$_1$–C$_3$ haloalkyl, C$_1$–C$_3$ haloalkoxy, Cl, Br, F, NO$_2$, di(C$_1$–C$_3$) alkylsulfamoyl, C$_1$–C$_3$ alkylthio, C$_1$–C$_3$ alkylsulfinyl, C$_1$–C$_3$ alkylsulfonyl, amino, C$_1$–C$_3$ alkylamino, di(C$_1$–C$_3$)alkylamino, CH$_2$OCH$_3$, CH$_2$SCH$_3$ or CH$_2$CN.
Z is N;
X$_3$ is CH$_3$ or OCH$_3$;
and their agriculturally suitable salts; provided that
(a) when R$_3$ is C$_1$–C$_3$ alkoxy, then Q$_1$ and Q$_2$ are oxygen;

(b) when $R_3$ is H or $C_1$-$C_3$ alkyl, then Q is Q-1 through Q-9;
(c) X or Y are other than $OCF_2H$;
(d) when the total number of carbon atoms of X and Y is greater than four, then the combined number of carbons of the substituents on Q is less than or equal to ten;
(e) when W is S, then A is A-1, R is H, and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH_2$, $OCH_2C\equiv CH$, $OCH_2CH_2OCH_3$, $CH(OCH_3)_2$ or

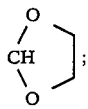

(f) when E is $CH_2$, then $R_{14}$ is H, $CH_3$, $OCH_3$, Cl or $NO_2$ and is not in the 4-position.

2. A compound of claim 1 where $R_3$ is H or $C_1$-$C_3$ alkyl.
3. A compound of claim 1 where $R_3$ is $C_1$-$C_3$ alkoxy.
4. A compound of claim 2 where W is O; R is H; X is $CH_3$, $OCH_3$, $OC_2H_5$, $CH_2F$, $OCH_2CH_2F$, $OCH_2CHF_2$, $OCH_2CF_3$ or $CF_3$; and Y is H, $C_1$-$C_3$ alkyl, $OCH_3$, $OC_2H_5$, $CH_2OCH_3$, $NHCH_3$, $(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$, $CH_2OC_2H_5$,

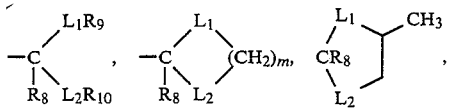

$SCF_2H$, cyclopropyl, $C\equiv CH$ or $C\equiv CCH_3$.

5. A compound of claim 4 where $Q_1$ and $Q_2$ are identical and are O or S, $R_{12}$ is H, $C_1$-$C_2$ alkyl or Cl and $R_{13}$ is H.
6. A compound of claim 5 where A is A-1; Y is $CH_3$, $OCH_3$, $OC_2H_5$, $CH_2OCH_3$, $C_2H_5$, $NHCH_3$, $CH_2OC_2H_5$, $OCH_2CH_2OCH_3$, cyclopropyl, $C\equiv CH$ or $CH(OCH_3)_2$; and X is $CH_3$, $OCH_3$, $OC_2H_5$, or $OCH_2CF_3$.
7. A compound of claim 6 where $Q_1$ and $Q_2$ are O.
8. A compound of claim 6 where $Q_1$ and $Q_2$ are S.
9. A compound of claim 6 where Q is Q-1.
10. A compound of claim 6 where Q is Q-2.
11. A compound of claim 6 where Q is Q-3.
12. A compound of claim 6 where Q is Q-4.
13. A compound of claim 6 where Q is Q-5.
14. A compound of claim 6 where Q is Q-6.
15. A compound of claim 6 where Q is Q-7.
16. A compound of claim 6 where Q is Q-8.
17. A compound of claim 6 where Q is Q-9.
18. A compound of claim 3 where W is O; R is H; X is $CH_3$, $OCH_3$, $OC_2H_5$, $CH_2F$, $OCH_2CH_2F$, $OCH_2CHF_2$, $OCH_2CF_3$ or $CF_3$; and Y is H, $C_1$-$C_3$ alkyl, $OCH_3$, $OC_2H_5$, $CH_2OCH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$, $CH_2OC_2H_5$,

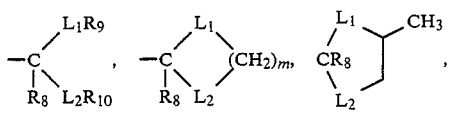

$SCF_2H$, cyclopropyl, $C\equiv CH$ or $C\equiv CCH_3$.

19. A compound of claim 18 where E is a single bond; $R_{12}$ is H, $C_1$-$C_2$ alkyl or Cl; $R_{13}$ is H; and $R_{14}$ is H, F, Cl, Br, $C_1$-$C_2$ alkyl, $C_1$-$C_2$ alkoxy or $C_1$-$C_2$ alkylthio and is not para to the sulfonylurea bridge.
20. A compound of claim 19 where A is A-1; Y is $CH_3$, $OCH_3$, $OC_2H_5$, $CH_2OCH_3$, $C_2H_5$, $NHCH_3$, $CH_2OC_2H_5$, $OCH_2CH_2OCH_3$, cyclopropyl, $C\equiv CH$ or $CH(OCH_3)_2$; and X is $CH_3$, $OCH_3$, $OC_2H_5$, or $OCH_2CF_3$.
21. A compound of claim 20 where Q is Q-1.
22. A compound of claim 20 where Q is Q-2.
23. A compound of claim 20 where Q is Q-3.
24. A compound of claim 20 where Q is Q-4.
25. A compound of claim 20 where Q is Q-5.
26. A compound of claim 20 where Q is Q-6.
27. A compound of claim 20 where Q is Q-7.
28. A compound of claim 20 where Q is Q-8.
29. A compound of claim 20 where Q is Q-9.
30. A compound of claim 20 where Q is Q-10.
31. A compound of claim 1 which is 3-(1,3-dioxolan-2-yl)-N-[(4-methoxy-6-methyl-1,3,5-triazin-2-yl)aminocarbonyl]-2-thiophenesulfonamide.
32. A composition suitable for controlling the growth of undesired vegetation which comprises an effective amount of a compound of claim 1 and at least one of the following: surfactant, solid or liquid inert diluent.
33. A composition suitable for controlling the growth of undesired vegetation which comprises an effective amount of a compound of claim 2 and at least one of the following: surfactant, solid or liquid inert diluent.
34. A composition suitable for controlling the growth of undesired vegetation which comprises an effective amount of a compound of claim 3 and at least one of the following: surfactant, solid or liquid inert diluent.
35. A composition suitable for controlling the growth of undesired vegetation which comprises an effective amount of a compound of claim 4 and at least one of the following: surfactant, solid or liquid inert diluent.
36. A composition suitable for controlling the growth of undesired vegetation which comprises an effective amount of a compound of claim 5 and at least one of the following: surfactant, solid or liquid inert diluent.
37. A composition suitable for controlling the growth of undesired vegetation which comprises an effective amount of a compound of claim 6 and at least one of the following: surfactant, solid or liquid inert diluent.
38. A composition suitable for controlling the growth of undesired vegetation which comprises an effective amount of a compound of claim 18 and at least one of the following: surfactant, solid or liquid inert diluent.
39. A composition suitable for controlling the growth of undesired vegetation which comprises an effective amount of a compound of claim 19 and at least one of the following: surfactant, solid or liquid inert diluent.
40. A composition suitable for controlling the growth of undesired vegetation which comprises an effective amount of a compound of claim 20 and at least one of the following: surfactant, solid or liquid inert diluent.
41. A method for controlling the growth of undesired vegetation which comprises applying to the locus to be protected an effective amount of a compound of claim 1.

42. A method for controlling the growth of undesired vegetation which comprises applying to the locus to be protected an effective amount of a compound of claim 2.

43. A method for controlling the growth of undesired vegetation which comprises applying to the locus to be protected an effective amount of a compound of claim 3.

44. A method for controlling the growth of undesired vegetation which comprises applying to the locus to be protected an effective amount of a compound of claim 4.

45. A method for controlling the growth of undesired vegetation which comprises applying to the locus to be protected an effective amount of a compound of claim 5.

46. A method for controlling the growth of undesired vegetation which comprises applying to the locus to be protected an effective amount of a compound of claim 6.

47. A method for controlling the growth of undesired vegetation which comprises applying to the locus to be protected an effective amount of a compound of claim 18.

48. A method for controlling the growth of undesired vegetation which comprises applying to the locus to be protected an effective amount of a compound of claim 19.

49. A method for controlling the growth of undesired vegetation which comprises applying to the locus to be protected an effective amount of a compound of claim 20.

* * * * *